(12) United States Patent
Hirsch

(10) Patent No.: US 7,507,764 B2
(45) Date of Patent: Mar. 24, 2009

(54) AMPHIPHILIC [5:1]- AND [3:3]-HEXAKISADDUCTS OF FULLERENES

(75) Inventor: Andreas Hirsch, Rathsberg (DE)

(73) Assignee: Tego BioSciences Corporation, Pasadena, CA (US)

( * ) Notice: Subject to any disclaimer, the term of this patent is extended or adjusted under 35 U.S.C. 154(b) by 503 days.

(21) Appl. No.: 10/963,990

(22) Filed: Oct. 13, 2004

(65) Prior Publication Data

US 2005/0143327 A1 Jun. 30, 2005

Related U.S. Application Data

(60) Provisional application No. 60/511,763, filed on Oct. 15, 2003.

(51) Int. Cl.
*A61K 31/235* (2006.01)
*C07D 319/00* (2006.01)
*C07C 69/76* (2006.01)

(52) U.S. Cl. .................. 514/533; 549/274; 977/735; 560/82

(58) Field of Classification Search .............. 514/33, 514/533, 359, 381; 536/18.1; 548/253, 255; 560/82; 549/274; 977/735
See application file for complete search history.

(56) References Cited

U.S. PATENT DOCUMENTS 6,506,928 B1 1/2003 Hirsch .................. 560/80

2003/0180491 A1 9/2003 Hirsch et al. .............. 428/35.7

FOREIGN PATENT DOCUMENTS

WO WO03/068185 8/2003

OTHER PUBLICATIONS

Braun et al., *Eur. J. Org. Chem.*, pp. 1173-1181 (2000).
Braun et al., *Eur. J. Org. Chem.*, pp. 1983-2001 (2004).
Brettreich et al., *Angew. Chem. Intl. Ed.* 39(10):1845-1846 (2000).
Hirsch et al., *Eur. J. Org. Chem.*, pp. 829-848 (2001).
PCT/US2004/034003 International Search Report (Mar. 3, 2005).
Gharbi et al., *ECS Proceedings* (May 14-19, 2000).
Mishra et al., *Drug Deliv.* 7:155-159 (2000).
Guo et al., *Drug Deliv.* 7:113-116 (2000).
Guo et al., *Acc. Chem. Res.* 36:335-341 (2003).
Freund, *Drug. Deliv.* 8:239-244 (2001).
Braun et al., *Carbon* 38:1565-1572 (2000).
Brettreich et al., *Angew. Chem. Int. Ed.* 39(10):1845-1848 (2000).
Maierhofer et al., *Langmuir* 16:8884-8891 (2000).
Maierhofer et al., *J. Phys. Chem. B* 105:3639-3645 (2001).
Lamparth et al., *Angew. Chem. Int. Ed. Engl.* 34(15):1607-1609 (1995).

(Continued)

*Primary Examiner*—Taylor Victor Oh
(74) *Attorney, Agent, or Firm*—Williams, Morgan & Amerson, P.C.

(57) ABSTRACT

Herein are disclosed substituted fullerenes, comprising a fullerene core (Cn), wherein n is an even integer greater than or equal to 60; 3 or 5 dihydrocarbylmalonate ($>C(COOR^1)(COOR^2)$) groups bonded to the fullerene core; and 1 or 3 polar extended malonate groups ($>C(COOR^3)(COOR^4)$) bonded to the fullerene core. The substituted fullerenes can form micelles, and can be used to ameliorate oxidative stress diseases.

2 Claims, 19 Drawing Sheets

OTHER PUBLICATIONS

Lamparth et al., *Tetrahedron* 52:5065-5075 (1996).
Gallani et al., *Langmuir* 18:2908-2913 (2002).
Felder et al., *Helv. Chim. Acta* 85:288-319 (2002).
Felder et al., *Helv. Chim. Acta* 84:1119-1132 (2001).
Nierengarten et al., *J. Am. Chem. Soc.* 123:9743-9748 (2001).
Angelini et al., *Langmuir* 17:6404-6407 (2001).
Nakamaura et al., *Bull. Chem. Soc. Jpn.* 73:1615-1619 (2000).
Jonas et al., *Chem. Eur. J.* 1:243-251 (1995).
Matsumoto et al., *Langmuir* 11:660-665 (1995).
Diederich et al., *Helv. Chim. Acta* 76:2445-2453 (1993).
Cassell et al., *Angew. Chem. Int. Ed.* 38(16):2403-2405 (1999).
Zhou et al., *Science* 291:1944-1947 (Mar. 9, 2001).
Hetzer et al., *Angew. Chem. Int. Ed.* 38(13/14):1962-1965 (1999).
Staab et al., *Ber.* 95:1275-1283 (1962).
Camps et al., *J. Chem. Soc., Perkin Trans.* 1:1595-1596 (1997).
Camps, Ph.D., Dissertation, "Dendrimer-Fullerenes and Lipo-Fullerenes: Synthesis, Properties and Organisation," *Univ. of Erlangen-Nürnberg* (Apr. 1998) (English Summary).
Wegner, *Chimia* 28:475-484 (Sep. 1974) (German with English Abstract).
Wegner, *Z. Naturforschg B* 24:824-832 (Feb. 1969) (German with English Abstract).
Takeda et al., *Makromol. Chem.* 160:349-353 (1972).
Reuther et al., *Chem. Eur. J.* 8(10):2261-2273 (2002).
Buschhaus et al., *Tetrahedron* 59:3899-3915 (2003).
Isaacs et al., *Helv. Chim. Acta* 76:1231-1250 (1993).
Still et al., *J. Org. Chem.* 43:2923-2925 (1978).
Zuckermann et al., *Journal of Medicinal Chemistry* 37:2678-2685 (1994).

42 R = tBu
40 R = H

22 R = NH-Boc
23 R = NH₃⊕

24 R = NH-Boc

25  R = -NH-Boc
29  R = -NH$_3^{\oplus}$

26  R = -NH-Boc
30  R = -NH$_3^{\oplus}$

27 R = -NH-Boc
31 R = -NH₃⊕

28  R = -NH-Boc
32  R = -NH₃⊕

33

34

35

36

45 R = tBu
47 R = H

46 R = tBu
48 R = H

31

AMPHIPHILIC [5:1]- AND [3:3]-HEXAKISADDUCTS OF FULLERENES

The present application claims priority from U.S. Provisional Patent Application Ser. No. 60/511,763, filed on Oct. 15, 2003.

BACKGROUND OF THE INVENTION

The present invention relates generally to the fields of fullerenes and their uses. More particularly, it concerns amphiphilic substituted fullerenes and their use in forming micelles or treating oxidative stress diseases.

Buckminsterfullerenes, also known as fullerenes or, more colloquially, "buckyballs," are cage-like molecules consisting essentially of $sp^2$-hybridized carbons. Fullerenes were first reported by Kroto et al., Nature (1985) 318:162. Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. Common fullerenes include $C_{60}$ and $C_{70}$, although fullerenes comprising up to about 400 carbon atoms are also known.

$C_{60}$ has 30 carbon-carbon double bonds, and has been reported to readily react with oxygen radicals (Krusic et al., Science (1991) 254:1183-1185). Other fullerenes have comparable numbers of carbon-carbon double bonds and would be expected to be about as reactive with oxygen radicals. However, native fullerenes are generally only soluble in apolar organic solvents, such as toluene or benzene. To render fullerenes water-soluble, as well as to impart other properties to fullerene-based molecules, a number of fullerene substituents have been developed.

Methods of substituting fullerenes with various substituents are known in the art. Methods include 1,3-dipolar additions (Sijbesma et al., J. Am. Chem. Soc. (1993) 115:6510-6512; Suzuki, J. Am. Chem. Soc. (1992) 114:7301-7302; Suzuki et al., Science (1991) 254:1186-1188; Prato et al., J. Org. Chem. (1993) 58:5578-5580; Vasella et al., Angew. Chem. Int. Ed. Engl. (1992) 31:1388-1390; Prato et al., J. Am. Chem. Soc. (1993) 115:1148-1150; Maggini et al., Tetrahedron Lett. (1994) 35:2985-2988; Maggini et al., J. Am. Chem. Soc. (1993) 115:9798-9799; and Meier et al., J. Am. Chem. Soc. (1994) 116:7044-7048), Diels-Alder reactions (Iyoda et al., J. Chem. Soc. Chem. Commun. (1994) 1929-1930; Belik et al., Angew. Chem. Int. Ed. Engl. (1993) 32:78-80; Bidell et al., J. Chem. Soc. Chem. Commun. (1994) 1641-1642; and Meidine et al., J. Chem. Soc. Chem. Commun. (1993) 1342-1344), other cycloaddition processes (Saunders et al., Tetrahedron Lett. (1994) 35:3869-3872; Tadeshita et al., J. Chem. Soc. Perkin. Trans. (1994) 1433-1437; Beer et al., Angew. Chem. Int. Ed. Engl. (1994) 33:1087-1088; Kusukawa et al., Organometallics (1994) 13:4186-4188; Averdung et al., Chem. Ber. (1994) 127:787-789; Akasaka et al., J. Am. Chem. Soc. (1994) 116:2627-2628; Wu et al., Tetrahedron Lett. (1994) 35:919-922; and Wilson, J. Org. Chem. (1993) 58:6548-6549); cyclopropanation by addition/elimination (Hirsch et al., Agnew. Chem. Int. Ed. Engl. (1994) 33:437-438 and Bestmann et al., C. Tetra. Lett. (1994) 35:9017-9020); and addition of carbanions/alkyl lithiums/Grignard reagents (Nagashima et al., J. Org. Chem. (1994) 59:1246-1248; Fagan et al., J. Am. Chem. Soc. (1994) 114:9697-9699; Hirsch et al., Agnew. Chem. Int. Ed. Engl. (1992) 31:766-768; and Komatsu et al., J. Org. Chem. (1994) 59:6101-6102); among others. The synthesis of substituted fullerenes is reviewed by Murphy et al., U.S. Pat. No. 6,162,926.

Hirsch, U.S. Pat. No. 6,506,928, is believed to be the first reference reporting dendrimeric fullerene derivatives. Hirsch disclosed the use of dendrimeric fullerene derivatives in fabricating a pharmaceutical intended for use as a neuroprotectant. Gharbi et al., ECS Proceedings, May 14-19, 2000, also reports that a particular dendrimeric fullerene, known as DF-1, is a free radical scavenger.

In recent years, a variety of approaches have been studied and used for drug delivery, DNA transfection, and other medical and biological applications. One such set of approaches involves vesicles or liposomes (the two terms will be used interchangeably herein).

Mishra et al., Drug Deliv. (2000) 7(3):155-159 teaches the loading of erythrocyte ghosts with doxorubicin HCl. So-called reverse biomembrane vesicles were formed by budding of membrane into the ghost interiors (endocytosis) leading to accumulation of small vesicles within each parent ghost. The amount of doxorubicin entrapped in reverse biomembrane vesicles was 0.75 mg/ml of packed vesicles. The in vitro release profile showed 52.86% of drug release in 16 hr.

Guo et al., Drug Deliv. (2000) 7(2):113-116 teaches preparation of flexible lecithin vesicles containing insulin and assessed the effect of these vesicles on the transdermal delivery of insulin. When vesicles were applied onto mice abdominal skin, blood glucose dropped by greater than 50% within 18 hr.

Freund, Drug Deliv. (2001) 8(4):239-244 teaches the encapsulation of therapeutic molecules in a noncationic multilamellar vector comprising phosphatidylcholine, cholesterol, and polyoxyethylene alcohol. Such vectors with entrapped drugs were prepared by shearing a phospholipidic lyotropic lamellar phase.

Amphiphilic derivatized fullerenes have been reported by Hirsch et al., Angew. Chem. Int. Ed. (2000) 39(10):1845-1848. The derivatized fullerenes of Hirsch comprised one dendrimeric group comprising 18 carboxylic acid moieties and five hydrophobic moieties each comprising a pair of lipophilic $C_{12}$ hydrocarbon chains. Freeze-fracture electron micrography of aqueous solutions of the amphiphilic derivatized fullerenes revealed that the amphiphilic derivatized fullerenes formed bilayer vesicles (by which is meant, a vesicle defined by a membrane comprising an external layer of amphiphilic derivatized fullerene molecules substantially all oriented with their hydrophilic groups to the exterior of the vesicle, and an internal layer of amphiphilic derivatized fullerene molecules substantially all oriented with their hydrophilic groups to the interior of the vesicle, wherein the hydrophobic groups of the molecules of the external layer are in close proximity to the hydrophobic groups of the molecules of the internal layer) with diameters from about 100 nm to about 400 nm.

Braun et al., Eur. J. Org. Chem. (2000) 1173-1181, teaches the synthesis of biotinated lipofullerenes.

SUMMARY OF THE INVENTION

In one embodiment, the present invention relates to a substituted fullerene, comprising (i) a fullerene core (Cn), wherein n is an even integer greater than or equal to 60; (ii) 3 or 5 dihydrocarbylmalonate ($>C(COOR^1)(COOR^2)$) groups bonded to the fullerene core; and (iii) 1 or 3 polar extended malonate groups ($>C(COOR^3)(COOR^4)$) bonded to the fullerene core.

In another embodiment, the present invention relates to a composition, comprising the substituted fullerene, described above, and a pharmaceutically-acceptable or comestibly-acceptable carrier.

In an additional embodiment, the present invention relates to a micelle, comprising an outer layer having an inner surface and an outer surface, the outer layer comprising a plurality of substituted fullerenes as described above; wherein the outer surface of the outer layer is defined by an interface between the polar extended malonate groups of the substituted fullerenes and an aqueous solvent.

In yet another embodiment, the present invention relates to a method of ameliorating an oxidative stress disease, comprising administering to a mammal an effective amount of the substituted fullerene, described above.

In still an additional embodiment, the present invention relates to a method of ameliorating damage to tissues for transplantation, ameliorating spoilage of food, inhibiting microbes, or reducing free radical levels in tobacco, comprising contacting the tissues for transplantation, the food, the microbes, or the tobacco with an effective amount of the substituted fullerene, described above.

The substituted fullerenes and compositions comprising them can ameliorate oxidative stress diseases or provide a carrier for drugs or other useful compounds.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
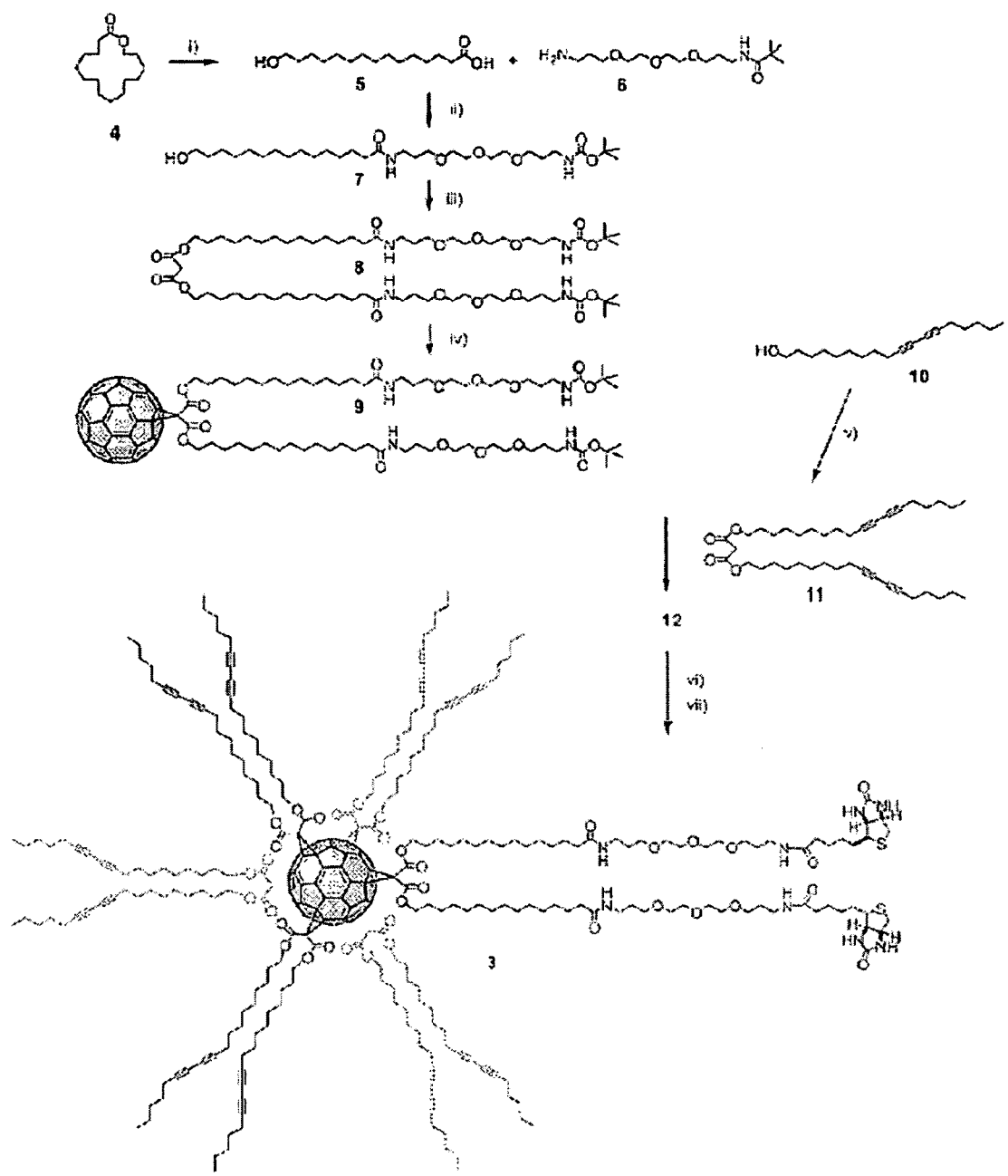
FIG. 1. Synthesis of the biotinated amphiphilic mixed [5:1] hexakisadduct 3 with a $C_{2v}$-symmetrical addition pattern of the $C_{60}$ central core (i: NaOH; ii: CDI; iii: malonic acid, CDI; iv: $C_{60}$, $CBr_4$, DBU, toluene, RT; v: malonyl dichloride, pyridine; vi: TFA, $CH_2Cl_2$; vii: CDI, biotin).

Throughout the present specification and claims, unless specified to the contrary, the word "or" has its inclusive meaning.

In one embodiment, the present invention relates to a substituted fullerene, comprising (i) a fullerene core (Cn), wherein n is an even integer greater than or equal to 60; (ii) 3 or 5 dihydrocarbylmalonate ($>C(COOR^1)(COOR^2)$) groups bonded to the fullerene core; and (iii) 1 or 3 polar extended malonate groups ($>C(COOR^3)(COOR^4)$) bonded to the fullerene core.

Buckminsterfullerenes, also known as fullerenes or, more colloquially, buckyballs, are cage-like molecules consisting essentially of $sp^2$-hybridized carbons and have the general formula ($C_{20+2m}$) (where m is a natural number). Fullerenes are the third form of pure carbon, in addition to diamond and graphite. Typically, fullerenes are arranged in hexagons, pentagons, or both. Most known fullerenes have 12 pentagons and varying numbers of hexagons depending on the size of the molecule. "$C_n$" refers to a fullerene moiety comprising n carbon atoms.

Common fullerenes include $C_{60}$ and $C_{70}$, although fullerenes comprising up to about 400 carbon atoms are also known.

Fullerenes can be produced by any known technique, including, but not limited to, high temperature vaporization of graphite. Fullerenes are available from MER Corporation (Tucson, Ariz.) and Frontier Carbon Corporation, among other sources.

A substituted fullerene is a fullerene having at least one substituent group bonded to at least one carbon of the fullerene core.

The particular substituted fullerenes of the present invention can be made by one or more techniques known in the art, either as stated above or as will be apparent to the ordinary skilled artisan having the benefit of the present disclosure. Such techniques further include, but are not limited to, reacting a fullerene with a macrocyclic group capable of adding desired substituents to the fullerene core, along the lines of Hirsch, U.S. Pat. No. 6,538,153.

In all embodiments, the substituted fullerene comprises a fullerene core (Cn), which can have any number of carbon atoms n, wherein n is an even integer greater than or equal to 60. In one embodiment, the Cn has 60 carbon atoms (and may be represented herein as $C_{60}$). In one embodiment, the Cn has 70 carbon atoms (and may be represented herein as $C_{70}$).

Throughout this description, particular embodiments described herein may be described in terms of a particular acid, amide, ester, or salt conformation, but the skilled artisan will understand an embodiment can change among these and other conformations depending on the pH and other conditions of manufacture, storage, and use. All such conformations are within the scope of the appended claims.

The substituted fullerene comprises 3 or 5 dihydrocarbylmalonate ($>$C(COOR$^1$)(COOR$^2$)) groups bonded to the fullerene core; and 1 or 3 polar extended malonate groups ($>$C(COOR$^3$)(COOR$^4$)) bonded to the fullerene core. The notation "$>$C" indicates the group is bonded to the fullerene core by two single bonds, each of which is between the carbon atom "C" and a carbon atom of the Cn.

In each dihydrocarbylmalonate group, ($>$C(COOR$^1$)(COOR$^2$)), R$^1$ and R$^2$ are independently any moiety comprising only hydrogen and carbon atoms. The moieties can be linear, branched, cyclic, or polycyclic, among others, and can comprise carbon-carbon single bonds, double bonds, triple bonds, or any or all thereof. In one embodiment, R$^1$ and R$^2$ are independently $C_1$-$C_{20}$ alkyl, $C_1$-$C_{20}$ alkenyl, or $C_1$-$C_{20}$ alkynyl. In a further embodiment, R$^1$ and R$^2$ are independently $C_2$-$C_{12}$ alkyl or $C_2$-$C_{12}$ alkenyl. In a particular embodiment, R$^1$ and R$^2$ are both ethyl. In another particular embodiment, R$^1$ and R$^2$ are both dodecyl.

In each polar extended malonate group, ($>$C(COOR$^3$)(COOR$^4$)), R$^3$ and R$^4$ are independently moieties comprising from 1 to about 50 atoms and at least one polar or charged group. A polar group is a group of one or more atoms which has a net dipole moment. A charged group is a group of one or more atoms which has a net charge. A charged group is also a polar group, though the opposite may be, but is not necessarily, true. In one embodiment, R$^3$ and R$^4$ are independently —(CH$_2$)$_a$—R, wherein a is an integer from 1 to 20 and R is a charged or polar group. In a further embodiment, each R independently comprises (i) an ethylene glycol chain and (ii) a charged or polar terminal group selected from biotin, —NH$_2$, —COOH, —CONH$_2$, or a protonated or deprotonated species thereof, wherein the ethylene glycol chain forms part or all of a chain linking the charged or polar terminal group to the —(CH$_2$)$_a$— group. In this embodiment, each R can also comprise other groups in the chain linking the terminal group to the —(CH$_2$)$_a$— group.

In another embodiment, R$^3$ and R$^4$ are independently a heterocyclic moiety or a branched moiety comprising one or more terminal —OH, —NH$_2$, triazole, tetrazole, or sugar groups.

A heterocyclic moiety is a moiety comprising a ring, wherein the atoms forming the ring are of two or more elements. Common heterocyclic moieties include those comprising carbon and nitrogen, among others.

A branched moiety is a moiety comprising at least one carbon atom which is bonded to three or four other carbon atoms, wherein the moiety does not comprise a ring. In a further embodiment, the branched moiety comprising one or more terminal —OH, —NH$_2$, triazole, tetrazole, or sugar groups can be selected from —(CH$_2$)$_a$—C(COH)$_g$(CH$_3$)$_{g-3}$, —(CH$_2$)$_a$—C(CNH$_2$)$_g$(CH$_3$)$_{g-3}$, —(CH$_2$)$_a$—C(C[tetrazol])$_g$(CH$_3$)$_{g-3}$, —(CH$_2$)$_a$—C(C[triazol])$_g$(CH$_3$)$_{g-3}$, —(CH$_2$)$_a$—C(C[hexose])$_g$(CH$_3$)$_{g-3}$, or —(CH$_2$)$_a$—C(C[pentose])$_g$(CH$_3$)$_{g-3}$, wherein g is an integer from 1 to 3, inclusive. In a further embodiment, g is an integer from 2 to 3, inclusive.

The 1 or 3 polar extended malonate groups can lend at least some degree of water solubility to at least some of the substituted fullerenes of the present invention.

Because the substituted fullerenes comprise both polar substituents and apolar substituents, they generally have amphiphilic character and may be referred to herein as amphiphilic fullerenes or amphifullerenes.

In one embodiment, the present invention relates to a composition, comprising:

a substituted fullerene, and a pharmaceutically-acceptable or comestibly-acceptable carrier.

The substituted fullerene can be as described above.

The carrier can be any material or plurality of materials which can form a composition with the substituted fullerene. The particular carrier can be selected by the skilled artisan in view of the intended use of the composition and the properties of the substituted fullerene, among other parameters apparent in light of the present disclosure.

Non-limiting examples of particular carriers and particular compositions follow.

In one embodiment, the carrier is water, and the composition is an aqueous solution comprising water and the substituted fullerene. The composition can further comprise solutes, such as salts, acids, bases, or mixtures thereof, among others. The composition can also comprise a surfactant, an emulsifier, or another compound capable of improving the solubility of the substituted fullerene in water.

In one embodiment, the carrier is a polar organic solvent, and the composition is a polar organic solution comprising the polar organic solvent and the substituted fullerene. Examples of polar organic solvents include, but are not limited to, methanol, ethanol, formate, acrylate, or mixtures thereof, among others. The composition can further comprise solutes, such as salts, among others. The composition can also comprise a surfactant, an emulsifier, or another compound capable of improving the solubility of the substituted fullerene in the polar organic solvent.

In one embodiment, the carrier is an apolar organic solvent, and the composition is an apolar organic solution comprising the apolar organic solvent and the substituted fullerene. "Apolar" has its standard meaning in the chemical arts of describing a molecule that does not have a permanent electric dipole. Examples of apolar organic solvents include, but are not limited to, hexane, cyclohexane, octane, toluene, benzene, or mixtures thereof, among others. The composition can further comprise solutes, such as apolar molecules, among others. The composition can also comprise a surfactant, an emulsifier, or another compound capable of improving the solubility of the substituted fullerene in the apolar organic solvent. In one embodiment, the composition is a water-in-oil emulsion, wherein the substituted fullerene is dissolved in water and water is emulsified into a continuous phase comprising one or more apolar organic solvents.

In one embodiment, the carrier is a mixture of water and other solvents. In one embodiment, the carrier can comprise one or more of dimethicone, water, urea, mineral oil, sodium lactate, polyglyceryl-3 diisostearate, ceresin, glycerin, octyldodecanol, polyglyceryl-2 dipolyhydroxystearate, isopropyl stearate, panthenol, magnesium sulfate, bisabolol, lactic acid, lanolin alcohol, or benzyl alcohol, among others.

In one embodiment, the composition has a creamy consistency suitable for packaging in a squeezable plastic container. In one embodiment, the composition has a lotion consistency suitable for packaging in a squeezable plastic container. In one embodiment, the composition has an ointment-like consistency suitable for packaging in a squeezable plastic container. In one embodiment, the composition has a liquid consistency suitable for packaging in a non-squeezable container. A non-squeezable container can be fabricated from one or more of plastic, glass, metal, ceramic, or other compounds. A non-squeezable container can be fabricated with a flow-type cap or a pump-type dispenser.

In one embodiment, the carrier is a solid or semisolid carrier, and the composition is a solid or semisolid matrix in or over which the substituted fullerene is dispersed. Examples of components of solid carriers include, but are not limited to, sucrose, gelatin, gum arabic, lactose, methylcellulose, cellulose, starch, magnesium stearate, talc, petroleum jelly, or mixtures thereof, among others. The dispersal of the substituted fullerene can be homogeneous (i.e., the distribution of the substituted fullerene can be invariant across all regions of the composition) or heterogeneous (i.e., the distribution of the substituted fullerene can vary at different regions of the composition). The composition can further comprise other materials, such as flavorants, preservatives, or stabilizers, among others.

In one embodiment, the carrier is a gas, and the composition can be a gaseous suspension of the substituted fullerene in the gas, either at ambient pressure or non-ambient pressure. Examples of the gas include, but are not limited to, air, oxygen, nitrogen, or mixtures thereof, among others.

Other carriers will be apparent to the skilled artisan having the benefit of the present disclosure.

In one embodiment, the carrier is a pharmaceutically-acceptable carrier. By "pharmaceutically-acceptable" is meant that the carrier is suitable for use in medicaments intended for administration to a mammal. Parameters which may considered to determine the pharmaceutical acceptability of a carrier can include, but are not limited to, the toxicity of the carrier, the interaction between the substituted fullerene and the carrier, the approval by a regulatory body of the carrier for use in medicaments, or two or more of the foregoing, among others. An example of pharmaceutically-acceptable carrier is an aqueous saline solution. In one embodiment, further components of the composition are pharmaceutically acceptable.

In one embodiment, the carrier is a comestibly-acceptable carrier. By "comestibly-acceptable" is meant that the carrier is suitable for use in food or food packaging wherein the food is intended for feeding to a mammal. Parameters which may considered to determine the comestible acceptability of a carrier can include, but are not limited to, the toxicity of the carrier, the interaction between the substituted fullerene and the carrier, the approval by a regulatory body of the carrier for use in food or food packaging, or two or more of the foregoing, among others. An example of a comestibly-acceptable carrier is starch. In one embodiment, further components of the composition are comestibly acceptable.

In addition to the substituted fullerene and the carrier, and further components described above, the composition can also further comprise other compounds, such as preservatives, adjuvants, excipients, binders, other agents capable of ameliorating one or more diseases, or mixtures thereof, among others. In one embodiment, the other compounds are pharmaceutically acceptable or comestibly acceptable.

The concentration of the substituted fullerene in the composition can vary, depending on the carrier and other parameters apparent to the skilled artisan having the benefit of the present disclosure. The concentration of other components of the composition can also vary along the same lines.

In another embodiment, the present invention relates to a micelle, comprising:

an outer layer having an inner surface and an outer surface, the outer layer comprising a plurality of substituted fullerenes as described above, wherein the outer surface of the outer layer is defined by an interface between the polar extended malonate groups of the substituted fullerene and an aqueous solvent.

A micelle, which may be referred to herein as a vesicle, is a collection of amphiphilic molecules, by which is meant, molecules which include both (a) hydrophilic ("water-loving") regions, typically charged or polar moieties, such as moieties comprising polar headgroups, among others known to one of ordinary skill in the art, and (b) hydrophobic ("water-hating") regions, typically apolar moieties, such as hydrocarbon chains, among others known to one of ordinary skill in the art. In aqueous solution, the micelle is formed when the amphiphilic molecules form a wall, i.e., a closed three-dimensional surface. The wall defines an interior of the micelle and an exterior of the micelle. Typically, the exterior surface of the wall is formed by amphiphilic molecules oriented such that their hydrophilic regions are in contact with water, the solvent in the aqueous solution. The interior surface of the wall may be formed by amphiphilic molecules oriented such that their hydrophilic regions are in contact with water present in the interior of the vesicle, or the interior surface of the wall may be formed by amphiphilic molecules oriented such that their hydrophobic regions are in contact with hydrophobic materials present in the interior of the vesicle.

The amphiphilic molecules in the wall will tend to form layers, and therefore, the wall may comprise one or more layers of amphiphilic molecules. If the wall consists of one layer, it may be referred to as a "unilayer membrane" or "monolayer membrane." If the wall consists of two layers, it may be referred to as a "bilayer membrane." Walls with more than two layers, up to any number of layers, are also within the scope of the present invention.

In one embodiment, the inner surface of the outer layer of the micelle is defined by an interface between the dihydrocarbylmalonate groups and an apolar material contained within the micelle.

In another embodiment, the micelle further comprises an inner layer having an inner surface and an outer surface, the inner layer comprising a plurality of substituted fullerenes as described above, wherein the inner surface of the outer layer and the outer surface of the inner layer are defined by an interface between the dihydrocarbylmalonate groups of the outer layer and the dihydrocarbylmalonate groups of the inner layer, and the inner surface of the inner layer is defined by an interface between the polar extended malonate groups and an aqueous solvent contained within the micelle.

An aqueous solvent is any composition comprising at least about 50 M water. Other components of an aqueous solvent can include, but are not limited to, buffers, salts, adjuvants, preservatives, acids, or bases, among others.

The micelle may be referred to herein as a "buckysome."

The micelle can be formed by any techniques known for the formation of micelles from amphiphilic molecules, such as agitation of aqueous solutions or suspensions thereof. In one embodiment, the micelle can be formed by adjusting the pH of an aqueous solution comprising the substituted fullerene. More discussion of the formation of micelles from amphiphilic fullerenes is given by Hirsch et al., U.S. patent application Ser. No. 10/367,646, filed Feb. 14, 2003.

In one embodiment, the present invention relates to a method of ameliorating an oxidative stress disease, comprising:

administering to a mammal an effective amount of a composition comprising a substituted fullerene, as described above, and a pharmaceutically-acceptable carrier. An "effective amount" of the substituted fullerene is an amount sufficient to ameliorate a disease.

By "ameliorating" a disease is meant improving the condition of a subject suffering or at risk of suffering from the disease. Ameliorating can comprise one or more of the following: a reduction in the severity of a symptom of the disease, a reduction in the extent of a symptom of the disease, a reduction in the number of symptoms of the disease, a reduction in the number of disease agents, a reduction in the spread of a symptom of the disease, a delay in the onset of a symptom of the disease, a delay in disease onset, or a reduction in the time between onset of the disease and remission of the disease, among others apparent to the skilled artisan having the benefit of the present disclosure. To the extent that the foregoing examples of ameliorating a disease are defined in relative terms, the proper comparison is to the disease or symptoms thereof when no composition is administered to ameliorate it and no method is performed to ameliorate it. The terms "preventing" (herein meaning "to stop a disease from onsetting") and "treating" (herein meaning "to improve the condition of a mammal suffering from a disease") are both within the scope of "ameliorating," as used herein.

In the present invention, the disease is an oxidative stress disease. An "oxidative stress disease" is a disease in which the healthy function of one or more organelles, non-organelle subcellular structures, cells, cell types, tissues, tissue types, organs, or organ systems is impaired by the action of oxidizing agents, such as free radicals, particularly radical oxygen species (ROS). The action of oxidizing agents need not be the only route by which impairment of healthy function occurs in the course of a disease for the disease to be an oxidative stress disease. In oxidative stress diseases, a number of sources of oxidizing agents are known. Exemplary sources include, but are not limited to, by-processes of metabolism, irritation by chemicals in the environment (for example, tobacco smoke), or internal challenge (for example, ischemia), among others.

Any one or more of a large number of oxidative stress diseases can be ameliorated by performance of the method.

In one embodiment, the oxidative stress disease is a central nervous system (CNS) neurodegenerative disease. Exemplary CNS neurodegenerative diseases include, but are not limited to, Parkinson's disease, Alzheimer's disease, multiple sclerosis, amyotrophic lateral sclerosis, or Huntington's disease.

In various embodiments, the oxidative stress disease is stroke, atherosclerosis, myocardial ischemia, myocardial reperfusion, or diabetes.

In one embodiment, the oxidative stress disease is a complication of diabetes. Examples of complications of diabetes include, but are not limited to, heart attack, stroke, circulatory impairment, retinopathy, blindness, kidney disease, pancreas disease, neuropathy, gum disease, and skin conditions, among others.

In various embodiments, the oxidative stress disease is circulatory impairment, retinopathy, blindness, kidney disease, pancreas disease, neuropathy, gum disease, cataracts, or skin disease.

In one embodiment, the oxidative stress disease is skin damage. Exemplary causes of skin damage include, but are not limited to, flame, heat, and radiation, such as ultraviolet light (UV), among others.

In one embodiment, the oxidative stress disease is radiation damage, by which is meant damage caused by exposure to alpha particles, beta particles, or electromagnetic radiation, such as UV or gamma rays, among others.

In various embodiments, the oxidative stress disease is damage caused by tobacco use, excessive angiogenesis, or insufficient angiogenesis.

In one embodiment, the oxidative stress disease is senescence. "Senescence," as used herein, refers to one or more of a decrease in the overall health of a mammal, a decrease in the overall fitness of a mammal, or a decrease in the overall quality of life of a mammal, wherein such decrease is generally attributed to the aging process. In one embodiment, ameliorating senescence may lead to maintenance of a particular level of systemic well-being to a later point in the mammal's life. In one embodiment, ameliorating senescence may lead to at least a partial increase in the expected lifespan of the mammal.

Methods of enhancing the overall health and longevity of humans and their companions has been a very active area of research. Given the conserved nature of cellular or developmental processes across metazoans, a number of model organisms have been employed to study senescence, including a nematode, *Caenorhabditis elegans*, and a fruit fly, *Drosophila melanogaster*.

For example, the genetic analysis of *C. elegans* has revealed several genes involved in lifespan determination. Mutations in Daf-2 (an insulin receptor) and Clk-1 ("Clock 1", a gene affecting many aspects of developmental and behavioral timing) have been shown to extend the lifespan of *C. elegans* adults. However, Clk-1 mutants have a higher mortality rate in early life. The Clk-1 longevity phenotype is abolished by mutations in the gene encoding catalase, which is involved in superoxide/free radical metabolism. Additionally, elimination of coenzyme Q in *C. elegans* diet has been shown to extend lifespan. These observations suggest reactive oxygen species are involved in senescence in *C. elegans*.

In *Drosophila*, superoxide dismutase (SOD) and catalase overexpression increased the lifespan by 35%. Mutations in the Methuselah gene ("Mth") have been shown to increase lifespan by 20%. The function of Mth, a G-protein coupled receptor, is not known, but mutants have shown an increased resistance to paraquat (a superoxide radical injury inducing agent). These observations suggest reactive oxygen species are involved in senescence in *Drosophila*.

Dugan et al., Publ. Patent Appl. US 2003/0162837, reported the oral administration of C3 to mice (at about 0.5 mg/kg/day) led to about a 20% increase in mean survival relative to controls (28.7+/−3.3 months vs. 23.5+/−5.5 months, p=0.033), thus suggesting an antioxidant compound was capable of ameliorating senescence.

Hearing loss refers to a state wherein the minimum audible threshold (in dB) of a sound of a particular frequency to a mammal is increased relative to an initial state.

Collateral damage of chemotherapy refers to injuries suffered by healthy tissues of a mammal upon exposure to cytotoxic drugs. Generally, chemotherapy is used in treating certain cancers, but this is not a limitation of the present invention.

Mucositis refers to a fungal infection of a mucous membrane. Fungal infections of mucous membranes are most common among immunocompromised individuals, such as people suffering from HIV infection or certain cancers or undergoing immunosuppressant therapy to combat rejection of transplanted organs, among others. However, fungal infections of the mucous membranes of any mammal are within the scope of "mucositis," as the term is used herein.

The composition and the substituted fullerene and the pharmaceutically-acceptable carrier comprised therein, can be as described above.

The compositions can be made up in any conventional form known in the art of pharmaceutical compounding. Exemplary forms include, but are not limited to, a solid form for oral administration such as tablets, capsules, pills, powders, granules, and the like. In one embodiment, for oral dosage, the composition is in the form of a tablet or a capsule of hard or soft gelatin, methylcellulose, or another suitable material easily dissolved in the digestive tract.

Typical preparations for intravenous administration would be sterile aqueous solutions including water/buffered solutions. Intravenous vehicles include fluid, nutrient and electrolyte replenishers. Preservatives and other additives may also be present.

In one embodiment, when the substituted fullerene is provided as a component of a micelle, the carrier can be water or a buffered solution.

In the administering step, the composition can be introduced into the mammal by any appropriate technique. An appropriate technique can vary based on the mammal, the oxidative stress disease, and the components of the composition, among other parameters apparent to the skilled artisan having the benefit of the present disclosure. Administration can be systemic, that is, the composition is not directly delivered to a tissue, tissue type, organ, or organ system the function of which is impaired by an oxidative stress disease, or it can be localized, that is, the composition is directly delivered to a tissue, tissue type, organ, or organ system the function of which is impaired by an oxidative stress disease. The route of administration can be varied, depending on the composition and the disease, among other parameters, as a matter of routine experimentation by the skilled artisan having the benefit of the present disclosure. Exemplary routes of administration include transdermal, subcutaneous, intravenous, intraarterial, intramuscular, intrathecal, intraperitoneal, oral, rectal, and nasal, among others. In one embodiment, the route of administration is oral or intravenous.

Fullerenes generally have toxicological properties similar to those of carbon, and substituted fullerenes are generally not expected to possess toxic activities. For example, repeated transdermal administration of fullerenes in benzene for up to 24 weeks (dose=200 µg/day) to mice did not result in either benign or malignant skin tumor formation (Nelson et al., *Toxicology & Indus. Health* (1993) 9(4):623-630). Further, no effect on either DNA synthesis or ornithine decarboxylase activity in dermal cells was observed over a 72-hr time course after treatment. Zakharenko et al., *Doklady Akademii Nauk.* (1994) 335(2):261-262, have shown that $C_{60}$ did not produce chromosomal damage at relatively high doses.

Though not to be bound by theory, it appears the substituted fullerene can ameliorate an oxidative stress disease by a reaction between the fullerene core and the oxidizing agent, resulting in an oxidizing agent product with lower oxidizing potential than the oxidizing agent. "Oxidizing potential" is used herein to refer to the maximum number of oxidizing reactions an agent can perform on biological molecules.

The mammal which is the subject of the method can be any mammal which can suffer an oxidative stress disease. An exemplary mammal is *Homo sapiens*, although other mammals possessing economic or esthetic utility (e.g., livestock such as cattle, sheep, or horses, among others; e.g., pets such as dogs and cats, among others; e.g., research animals such as mice, rats, or monkeys, among others) can be the subject of the method. Any one or more of the mammal, the person performing the method, or the person authorizing the performance of the method to the mammalian subject, can, but none need, be aware that the mammal suffers or can suffer an oxidative stress disease.

An effective amount of the substituted fullerene is one sufficient to affect an amelioration of the disease. The effective amount can vary depending on the identity of the substituted fullerene, or the disease, among others. In one embodiment, the effective amount is such that the dosage of the substituted fullerene to the subject is from about 1 µg/kg body weight/day to about 100 g/kg body weight/day. In a further embodiment, the effective amount is such that the dosage of the substituted fullerene to the subject is from about 1 mg/kg body weight/day to about 1 g/kg body weight/day.

Compositions for bolus intravenous administration may contain from about 1 µg/mL to 10 mg/mL (10,000 mg/liter) of the substituted fullerene. Compositions for drip intravenous administration preferably contain from about 50 mg/liter to about 500 mg/liter of the substituted fullerene.

In one embodiment, compositions for oral dosage are in the form of capsules or tablets containing from 50 mg to 500 mg of the substituted fullerene.

For ameliorating a chronic disease, the method can be performed one or more times per day for an indefinite period. For ameliorating an acute disease, such as stroke or myocardial ischemia, among others, the method can be performed one or more times for a brief period following the onset of the acute insult. Alternative durations of method performance are a matter of routine experimentation for the skilled artisan having the benefit of the present disclosure.

When the substituted fullerene is a component of a micelle, the method can further comprise administering a drug, wherein the drug is a discrete molecule, known for use as a medicament, which can be transported by the micelle. The drug can be dissolved in an aqueous solvent in the micelle interior, if the drug is hydrophilic. If the drug is hydrophobic, it can be a component of a hydrophobic micelle interior, if the inner wall of the innermost layer of the micelle is defined by an interface between dihydocarbylmalonate groups and the drug or other hydrophobic molecules. Alternatively, a hydrophobic drug can be dispersed in an emulsion or suspension in an aqueous solvent in the micelle interior, such as by use of a surfactant or emulsifier. In another embodiment, the drug, whether hydrophobic or hydrophilic, can be dispersed in a hydrophobic or hydrophilic, respectively, region within the micelle wall, if any.

The drug can be an antioxidant, or can have another function against an oxidative stress disease. Alternatively, a micelle containing the drug can be administered to treat a non-oxidative stress disease, wherein the drug is considered effective against the disease.

The use of vesicles comprising amphiphilic fullerenes to transport drugs or other therapeutic molecules in the amelioration of diseases is generally discussed by Hirsch et al., U.S. patent application Ser. No. 10/367,646, filed Feb. 14, 2003.

In one embodiment, the present invention relates to a method of ameliorating damage to tissues for transplantation, ameliorating spoilage of food, inhibiting microbes, or reducing free radical levels in tobacco, comprising:

contacting the tissues for transplantation, the food, the microbes, or the tobacco with an effective amount of a composition comprising a substituted fullerene and a pharmaceutically-acceptable or comestibly-acceptable carrier, as described above. An "effective amount" of the substituted fullerene is an amount sufficient to ameliorate the damage, ameliorate the spoilage, inhibit the microbes, or reduce the free radical levels, as applicable.

By "ameliorating" damage to tissues for transplantation is meant reducing oxidative damage to stored tissues. The stored tissues can be derived from cadavers, from living donors, or from tissues which may be grown, at present or in the future, by in vitro techniques. The stored tissues can be derived from humans or other animals, such as cattle or swine, among others, and can, but need not be, stored against implantation in a human or another animal. Examples of such tissues include, but are not limited to, whole blood, blood fractions, valves from the circulatory system, vessels and vessel portions from the circulatory system, hearts, lungs, corneas, kidneys, and livers, among others.

By "ameliorating" spoilage of food is meant at least one of reducing oxidative damage to stored food or extending the shelf-life of stored food, among others apparent to the skilled artisan having the benefit of the present disclosure. "Food" refers to any product which both (a) possesses nutritive value to humans or animals having economic, esthetic, or research value to humans and (b) is suitable for oral ingestion into the gastrointestinal tract.

By "inhibiting" microbes is meant at least one of reducing the number of microbes in a substrate susceptible to microbial culture, reducing the rate of growth of a microbe population in such a substrate, reducing the maximum population of a microbe population in such a substrate, or increasing the number of microbes required to establish a microbial culture in such a substrate, among others apparent to the skilled artisan having the benefit of the present disclosure. A "microbe" is any organism, virus, prion, or other biological molecule or collection of biological molecules capable of duplicating themselves or being duplicated under specific in vitro or in vivo conditions suitable for such duplication, wherein the organism or the like has a maximum dimension of 100 microns or less. Examples of microbes include various invertebrates, fungi, bacteria, cyanobacteria, archebacteria, viruses, and prions, among others.

By "reducing" free radical levels in tobacco is meant reducing the overall oxidizing potential of a tobacco composition. A "tobacco composition" is any compound containing nicotine, such as more than about 0.1 wt % nicotine. Typically, but not necessarily, the tobacco composition contains biological product of a plant of genus Nicotiana. Exemplary tobacco compositions include, but are not limited to, Nicotiana leaf (including fresh, dried, processed, whole, or comminuted leaf, among others), cigarette filler, cigar filler, pipe tobacco, chewing tobacco, snuff, maceration products of any of the foregoing, and combustion products of any of the foregoing, among others.

To the extent that the foregoing examples of ameliorating, inhibiting, or reducing are defined in relative terms, the proper comparison is to the condition obtaining when no composition is administered to the tissues for transplantation, food, microbes, or tobacco composition to ameliorate, etc. and no method is performed to ameliorate, etc.

The composition, and the substituted fullerene and the carrier comprised therein, can be as described above. The carrier can be a pharmaceutically-acceptable carrier or a comestibly-acceptable carrier.

In the contacting step, the tissue for transplantation, food, microbe, or tobacco composition can be contacted with the composition containing the substituted fullerene. The technique for contacting can be varied depending on the item to be contacted and the composition containing the substituted fullerene, among other parameters, as a matter of routine experimentation for the skilled artisan having the benefit of the present disclosure.

In one embodiment, wherein the item to be contacted is a tissue for transplantation and the composition is a liquid, the composition can be poured over or injected into the tissue, or the like.

In one embodiment, wherein the item to be contacted is a solid food and the composition is a solid, the composition can be dispersed in the food or contained in a sachet located in the food or affixed to an interior surface of a container containing the food.

In one embodiment, wherein the item to be contacted is a liquid food and the composition is a solid, the composition can be dissolved or suspended in the food or contained in a sachet located in the food or affixed to an interior surface of a container containing the food.

In one embodiment, wherein the item to be contacted is a liquid food and the composition is a liquid, the composition can be dissolved or mixed in the food or contained in a sachet located in the food or affixed to an interior surface of a container containing the food.

In one embodiment, wherein the item to be contacted is a microbe located on a substrate (such as a surface for which microbial inhibition is desired) and the composition is a liquid, the composition can be sprayed, poured, or the like onto the substrate.

In one embodiment, wherein the item to be contacted is a tobacco composition, and the substituted fullerene composition is a solid, the composition can be mixed into the tobacco composition or impregnated into a cigarette filter.

In one embodiment, wherein the item to be contacted is a tobacco composition, and the substituted fullerene composition is a liquid, the composition can be sprayed onto the tobacco composition or into a cigarette filter.

The following examples are included to demonstrate particular embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the embodiments which are disclosed and still obtain a like or similar result without departing from the spirit and scope of the invention.

EXAMPLE 1

A variety of new amphiphilic hexakisadducts of $C_{60}$ involving mixed octahedral [5:1]- and [3:3]-addition patterns were synthesized and characterized. The [5:1]-adducts 3 and 13 contain five pairs of didodecyl- or diethylmalonates as non-polar addends and as polar part an extended bismalonate involving C14- and ethylene glycol chains and two biotin termini. Amphiphilic [3:3]-hexakisadducts were prepared using the e,e,e-trisadduct 18 containing an cyclo-[3]-octyl-malonate addend as precursor molecule. As polar groups malonates with carboxy-, amino- or peptide termini were used. The charge on the termini which can range form zero up to sixfold positive or sixfold negative can be built up by protonation or deprotonation. In their fully charged form all amphiphilic [3:3]-hexakisadducts are very soluble in water. First investigations on the aggregation properties of amphiphilic [3:3]-hexakisadducts carried out by cryo-transmission-electron-microscopy (cryo-TEM) and pulse gradient spin echo (PGSE) NMR spectroscopy revealed pH-dependent formation of micelles or liposomes.

Introduction

Figure 11:
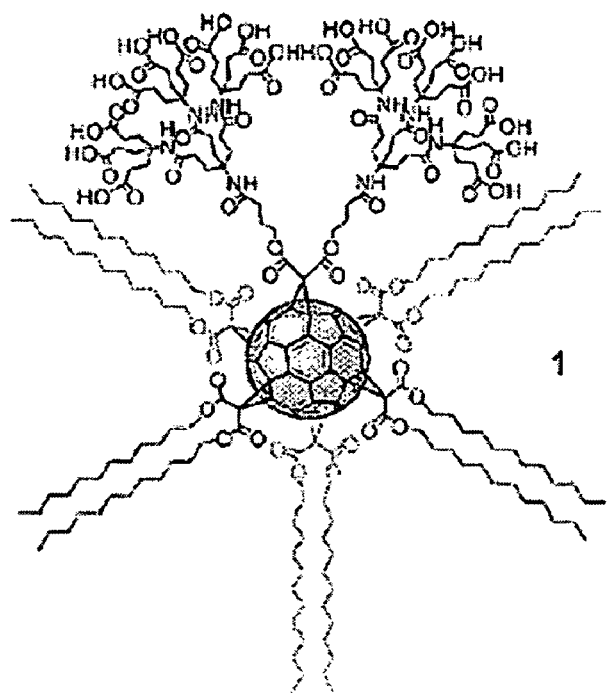
FIG. 11. Representations of compounds 1 and 2, as described in Example 1.
Figure 11:
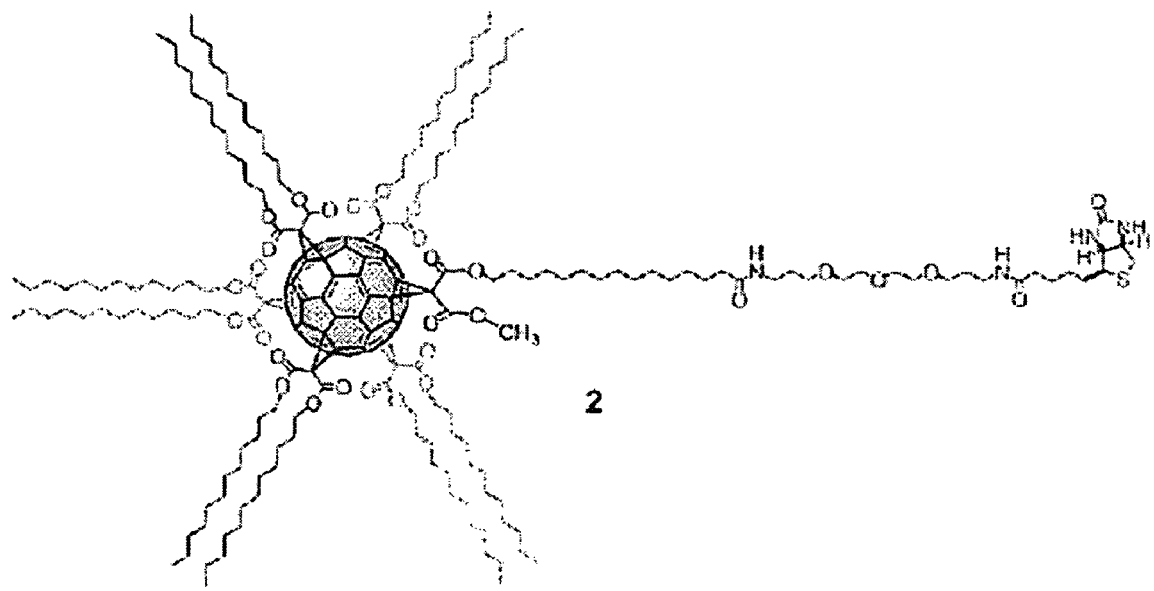

Two comparative examples, 1[1,2] and 2,[3,4,5] of amphiphlic [5:1]-hexakisadducts of $C_{60}$ involving an octahedral addition pattern were prepared previously.[6] (FIG. 11). The remarkably facile access to these stereochemically defined multiple adducts required control over the regioselectivity of the subsequent additions to [6,6]-bonds in equatorial sites. This was achieved with the template mediation strategy introduced previously[7] using 9,10-dimethylanthracene (DMA) as reversible binding precursor addends.

The globular amphiphile 1 readily dissolves in water at physiological pH, forming unilamellar vesicles (buckysomes) with diameters typically between 100 and 400 nm, and has a very small critical micelle concentration (CMC).[1] Stable mono layers of 1 on the air water interface were prepared by the Langmuir-Blodgett (LB) technique.[2] Thanks to the presence of 18 carboxylic groups which can be deprotonated successively, electrostatic interactions between the globular amphiphiles can be modified systematically making them interesting vehicles for the delivery of non-polar drug molecules. Amphifullerene 1 is expected to offer several advantages over conventional lipid based drug delivery systems.[8]. First, a higher loading capacity for lipophilic guest molecules located in between the bilayers can be expected since the radially arranged alkyl chains prevent dense packing within the unloaded vesicle. Secondly, the aggregation properties of the buckysomes can easily be modulated by pH variation. Thirdly, the presence of 18 carboxylic groups of 1 enables further functionalization such as targeting with labels or antibodies without loosing the aggregation properties.

The biofunctional amphifullerene 2 can intercalate into a DPPC bilayer and serve as a transmembrane anchor for proteins located outside the membrane.[3-5] The biotin anchor in 2 is able to bind proteins such as avidin and streptavidin. As a consequence the possibility of biocompatibilization of liposomes is provided. The amphiphilic behavior of 2 was demonstrated by LB-investigations.[5]

Since the investigation of the supramolecular properties of these first examples of amphiphilic hexakisadducts of $C_{60}$ was very encouraging, a whole range of amphifullerenes[9] were synthesized by systematically changing the nature of the hydrophilic and lipophilic addends and the nature of the hexaaddition pattern itself. In this contribution the syntheses of three new types of amphifullerenes involving [5:1]- and [3:3]-addition patterns carrying neutral as well as cationic and anionic polar groups are introduced. These new amphifullerenes are now available for the systematic investigation of their aggregation- and encapsulation properties.

Results and Discussion

Biotinated [5:1]-Amphifullerenes

A second generation biotinated [5:1]-amphiphile was synthesized, which is characterized by the following structural properties: i) one of the malonate addends should carry two biotin groups instead of one attached to spacer units that are long enough to protrude through a lecithin layer. It was expected that compared to 2 the amphiphilic character is more pronounced and that the ability to form micelles or vesicles is increased; ii) non-polar building blocks $C_{18}$-alkyl chains containing butadiyne units instead of saturated $C_{12}$-chains should be used allowing for subsequent 1,4-addition-type polymerization in the same way as reported for comparable lipofullerenes[10] In contrast to the polymerization of these lipofullerenes, where the formation of perfectly spherical polymer beads and destroyed lipid vesicles were found,[10] now polymerization inside the intact bilayer membrane is conceivable.

All these structural features are represented in the target molecule 3. The synthesis of 3 is shown in FIG. 1. The new biotin linker 7 involving an extended polar part as compared to 2 was obtained by COI-activated coupling[11] of hydroxypentadecanoic acid 5, derived from commercially available pentadecanolid 4, with the N-Boc-protected glycol 6. Subsequently, the corresponding malonate 8 was synthesized. Cyclopropanation[12] of 8 with $C_{60}$ led to the methanofullerene 9. The synthesis of bis-10,12-octadecadiynyl malonate 11 was achieved by coupling of the corresponding alcohol 10 with malonyl chloride.[13] The mixed [5:1]hexakisadduct 12 with a $C_{2v}$-symmetrical octahedral addition pattern[6] was obtained by exhaustive DMA mediated cyclopropanation[6,7,14] of 9 with malonate 11. Subsequently, the two Boc-protecting groups were removed with TFA/$CH_2Cl_2$. The final coupling with CDI-activated D(+)-biotin resulted in the target molecule 3.

Figure 6:
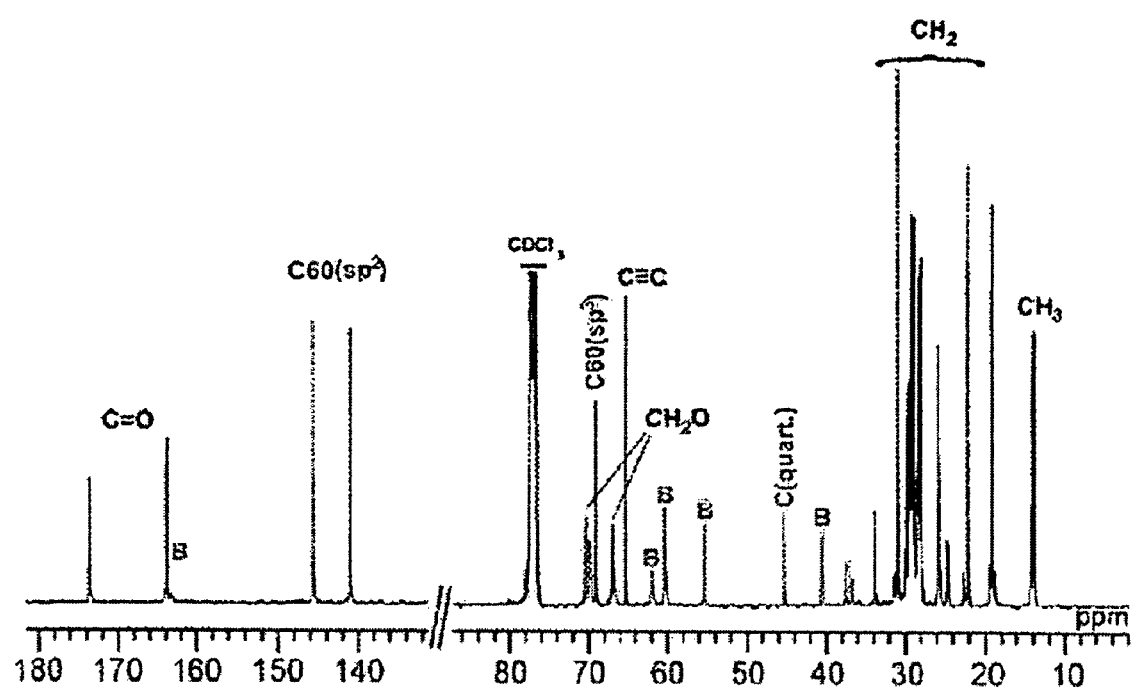
FIG. 6. $^{13}$C NMR spectrum (100.5 MHz, RT, $CDCl_3$) of hexakisadduct 3. The resonances marked in red belong to the C-atoms of the ether moiety of the spacer, B=biotin.

All reaction intermediates and products were fully characterized by means of $^1H$- and $^{13}C$-NMR-, and IR- or UV/Vis-spectroscopy as well as by mass spectrometry. The $^{13}C$ NMR spectrum of 3 nicely shows the expected signals for the terminal biotin groups and the two resonances of the $C_{60}$ $sp^2$-carbons, clearly demonstrating local $T_h$ symmetry around the fullerene nucleus (FIG. 6).

Figure 7:
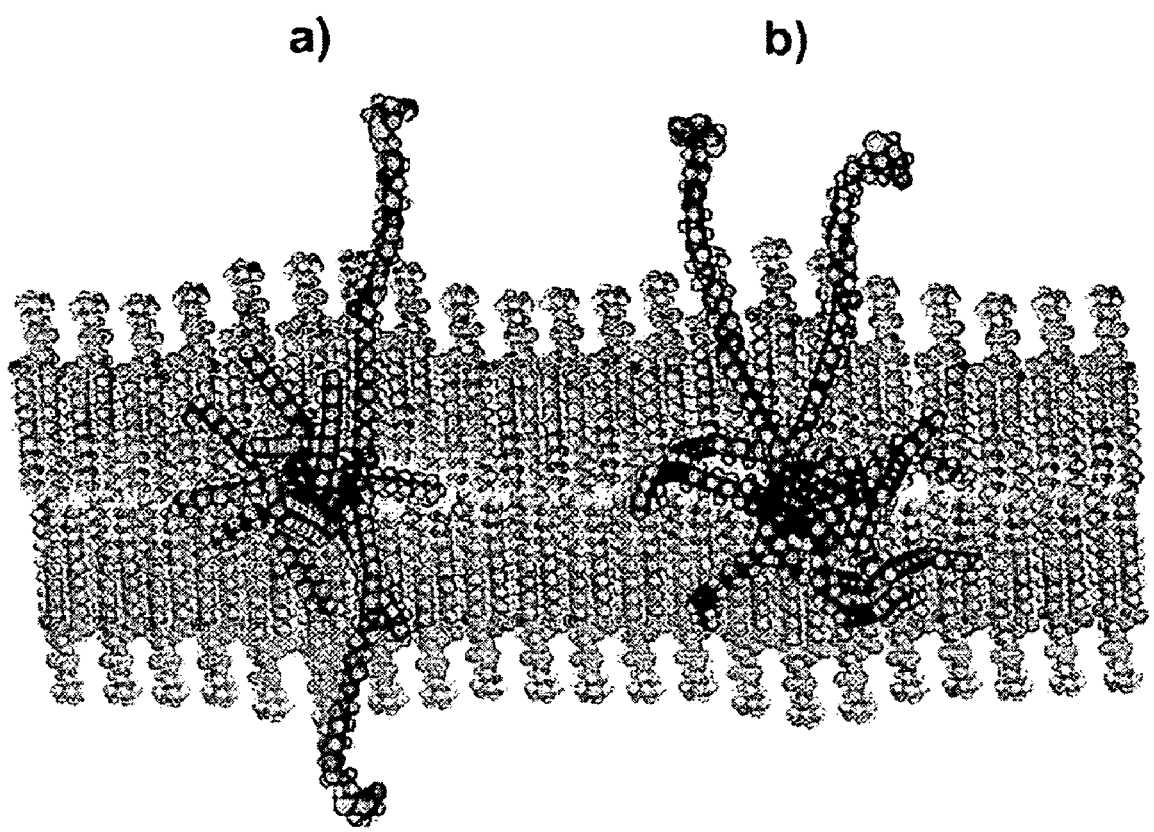
FIG. 7. CPK model of a DPPC lipid bilayer with amphifullerene 3 in trans- (left) and cis-orientation (right) of its biotinated transmembrane side chains, obtained from semiempirical PM3 geometry optimization (HyperChem, 6.01).

The interaction of the bifunctional amphifullerene 3 with lipid membranes as well as polymerization reactions within the corresponding composites are currently under investigation. Due to a trans-orientation of the two biotinated transmembrane side chains of amphifullerene 3 a bolaamphiphilic character can be expected. Two characteristic low energy orientations (a and b in FIG. 7) of the amphiphilic side chains were obtained by semiempirical calculations. The possible intercalation into a DPPC lipid membrane segment is shown in FIG. 7. After intercalation of 3 into the membrane, the biotins may act as transmembrane anchors and molecular recognition signals and the ten polymerizable malonate chains could allow photo-polymerization.[15]

Figure 2:
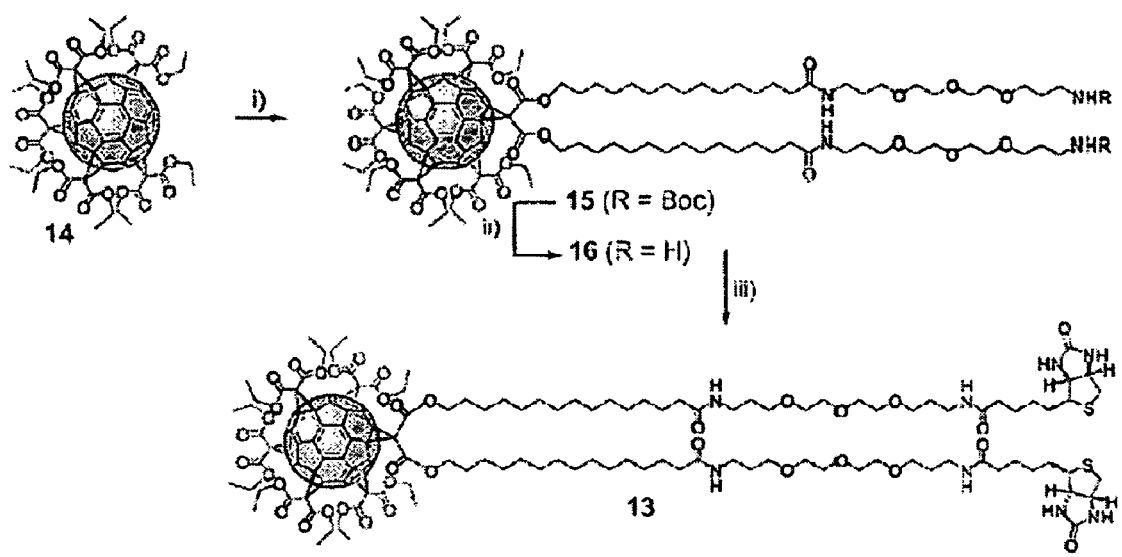
FIG. 2. Synthesis of amphiphilic bis-amino hexakisadduct 16 and its biotinated derivative 13 (i: malonate 8, $CBr_4$, DBU; ii: TFA, $CH_2Cl_2$; iii: CDI, D-(+)-biotin).

Concerning the solubility and aggregation properties in water hexakisadduct 3 did not meet the expectations. Acceptable solubility was only found in organic solvents like $CHCl_3$, $CH_2Cl_2$ and DMF. In water 3 is only soluble in the presence of a co-solvent like methanol. Thus self-aggregation behavior of 3 has not been investigated. To increase the polar character and to improve the water-solubility of such a bis-biotinated derivative, the [5:1]-hexakisadduct 13 with five ethyl malonate addends instead of the five octadecadiynyl malonates was synthesized (FIG. 2). To overcome the general problem of separating the desired hexakisadducts from other adducts formed simultaneously upon the exhaustive cyclopropanation step the sequence of addition steps was reversed in this case. For this purpose the cherry-red $C_{2v}$-symmetrical [5:0]-pentakisadduct 14[14] was prepared and used as starting material. The subsequent cyclopropanation reaction with the Boc-protected spacer malonate 8 to complete the $C_{2v}$-symmetrical octahedral addition pattern afforded the bright-yellow N-Boc-protected [5:1]-hexakisadduct 15 in 63% yield after FC and HPLC purification. After cleavage of the Boc-protecting groups with TFA/$CH_2Cl_2$ the bis-amino amphifullerene 16 was obtained in quantitative yield. The final coupling of two (+)biotin moieties via CDI activation to the amino termini resulted in the formation of the target molecule 13.

All reaction intermediates and products were fully characterized by means of $^1H$- and $^{13}C$-NMR-, and IR- or UV/Vis-spectroscopy as well as by mass spectrometry. Again, for the short chain bis-amino amphifullerene 16 and its biotinated derivative 13 appreciable solubility was only found in organic solvents like e.g. $CHCl_3$ and $CH_2Cl_2$. Compared to their corresponding octadecadiynyl analogues 12 and 3, an enhanced solubility in methanol was observed.

Water Soluble [3:3] Amphifullerenes

Figure 3:
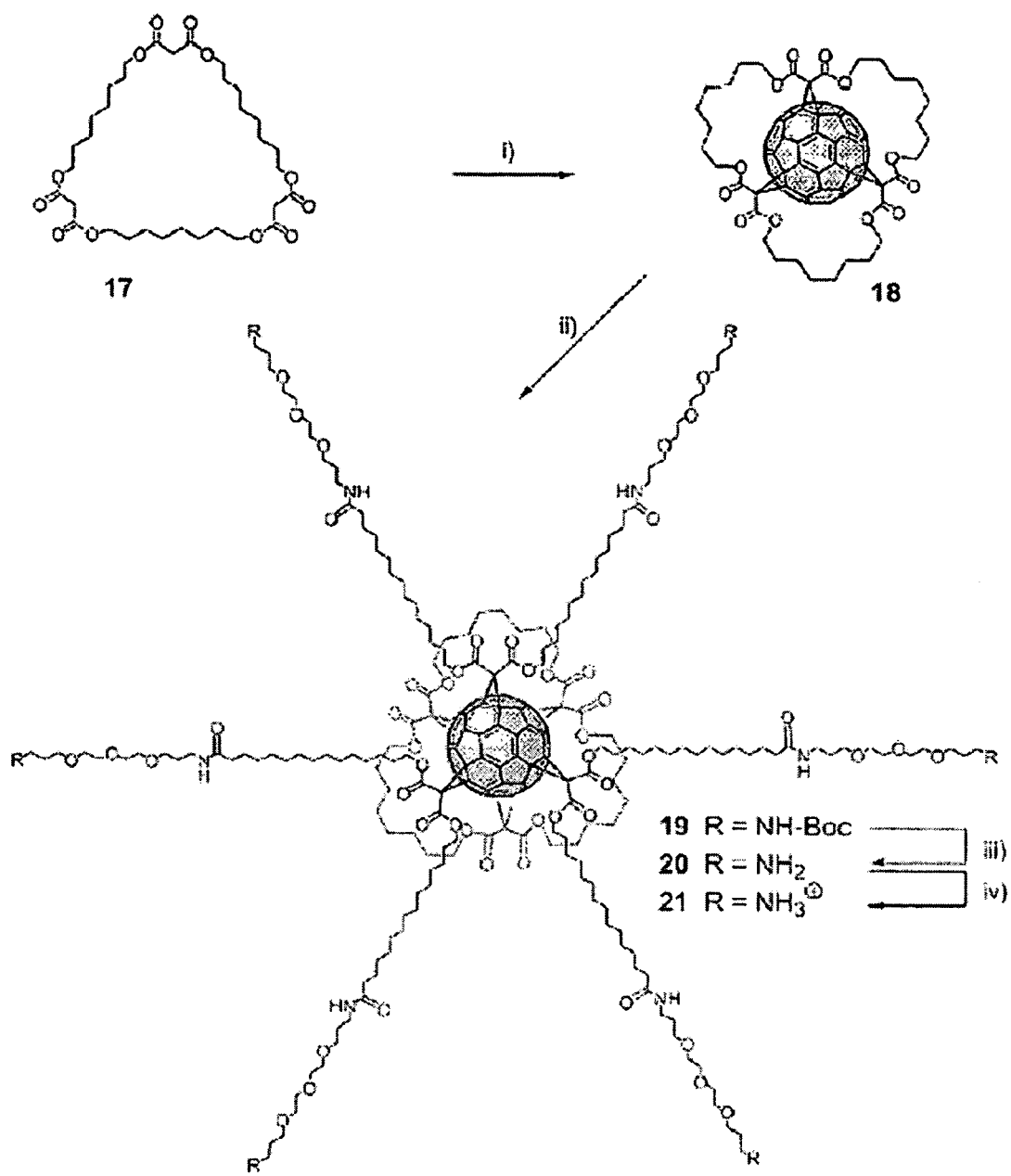
FIG. 3. Synthesis of the amphiphilic [3:3]-hexakisadduct 20 with a $C_3$-symmetrical addition pattern (i: 1.5 eq $C_{60}$, $CBr_4$, DBU; ii:DMA, malonate 8, $CBr_4$, DBU; iii: TFA, $CH_2Cl_2$; vi: $H_3O^+$).

The water-insoluble amphifullerenes 3 and 13 exhibited demixing properties and were shown to be inappropriate to form self-assemblies in water, probably because of an insufficient low amount of polar moieties. For an improvement of the amphiphilic character either larger polar addends are necessary as exemplified with the dendrofullerene 1 or a more balanced ratio of polar and non-polar addends can be considered. For this purpose [3:3]-hexakisadducts containing three pairs of non-dendritic polar chains were chosen as target systems. In order to guarantee an easy access to amphiphlic [3:3]-hexakisadducts in satisfactory yields macrocyclic cyclo-[3]-octylmalonate 17[16] was used for the initial addition to $C_{60}$ (FIG. 3). Multiple adducts of $C_{60}$ with specific addition patterns are accessible in good yields with remarkable and in many cases complete regioselectivity in one synthesis step when flexible cyclo-[n]-malonates are used as addends, as was recently reported.[16] The high regio-selectivities are a result of the nearly balanced distribution of strain energy within the flexible alkyl chains of the cyclo-[n]-malonates. For example, the e,e,e-trisadduct 18 (FIG. 3) in which the cyclic malonate is attached to three adjacent octahedral [6,6]-binding sites can be obtained in a very pronounced regioselectivity and an isolated yield of 64% yield after HPLC purification upon reaction of $C_{60}$ with 17. In the context of amphiphilic fullerenes the trismalonate addend in 18 comprising three $C_{12}$ chains serves as the non-polar building part of the amphiphile. The remaining octahedral binding sites within 18 are free for the addition of three polar malonates. Very favorable for this purpose is the fact that the completion of an octahedral addition pattern proceeds in very good regioselectivities both with and without use of the template mediation strategy.[6] Both cationic or anionic end groups are possible to support the water-solubility and to enable pH-dependent aggregation.

Cationic Water Soluble [3:3]-Amphifullerenes

As a first example of a cationic [3:3]-amphifullerene the synthesis of compound 20 was carried out. The compound 20 can be reversibly protonated to give 21 (FIG. 3). To provide the lipophilic e,e,e-trisadduct 18 with polar moieties the octahedral addition pattern was completed by DMA-templated cyclopropanation[7] with an excess of the spacer malonate 8. The Boc-protected $C_3$-symmetrical [3:3]-hexakisadduct 19 was obtained in 55% yield after HPLC separation. The cleavage of the Boc-protection groups was achieved with TFA. The resulting amphifullerene 20 can subsequently be protonated to give the target molecule 21 (FIG. 3). All reaction intermediates and products were fully characterized by $^1H$ and $^{13}C$ NMR-, and IR- or UV/Vis-spectroscopy as well as by mass spectrometry.

Figure 8:
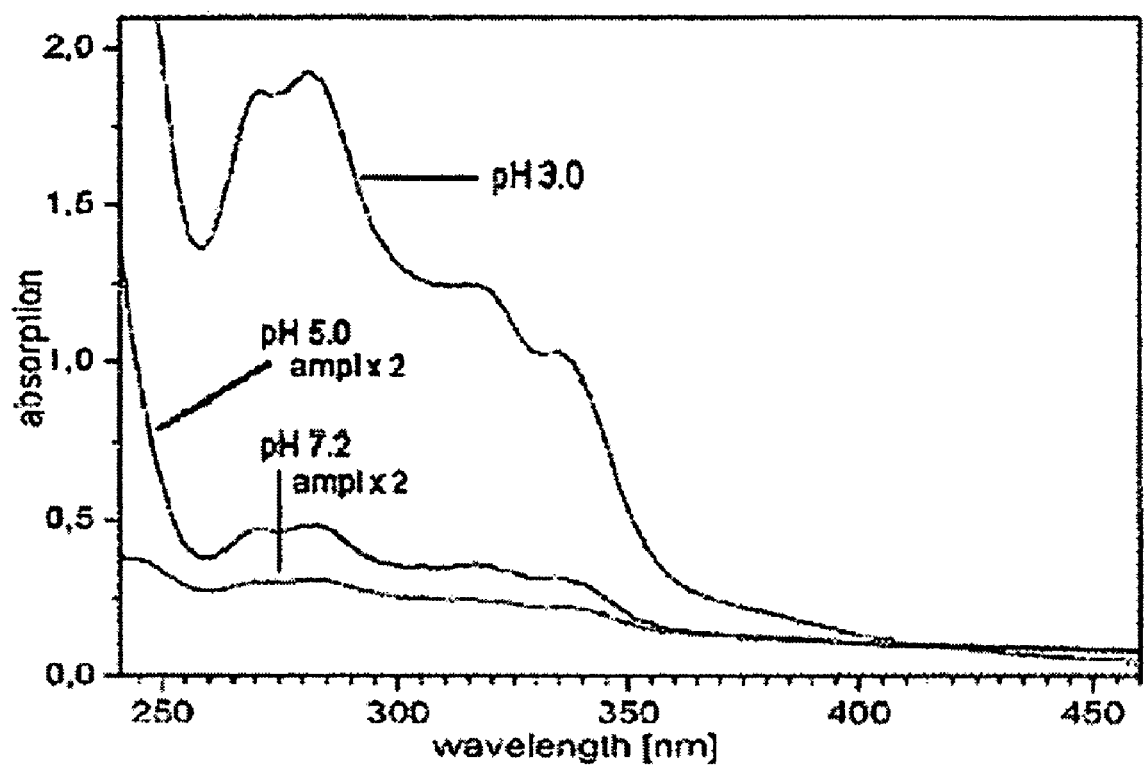
FIG. 8. UV/Vis spectra of aqueous solutions of hexakisadduct 20 at different pH values (Shimadzu UV-3102 PC).

The pH-dependent water-solubility of 20 was demonstrated by UV/Vis spectroscopic investigations. At neutral pH (buffered) and in weakly acidic solution a very low solubility of 20 was achieved. The saturated aqueous solutions were almost colorless because of the low concentration and the UV/Vis hexakisadduct bands very weak because of low solubility (FIG. 8). Upon lowering the pH value to pH=5 an increase of water solubility takes place causing a slight increase of the absorption. Finally, at a pH of 3 where all amino groups are completely protonated to give the cationic amphiphile 21 the whole material was transferred into a yellow solution. Now all absorption bands characteristic for a hexaskisadduct with an octahedral addition pattern exhibited high intensity.

Figure 9:
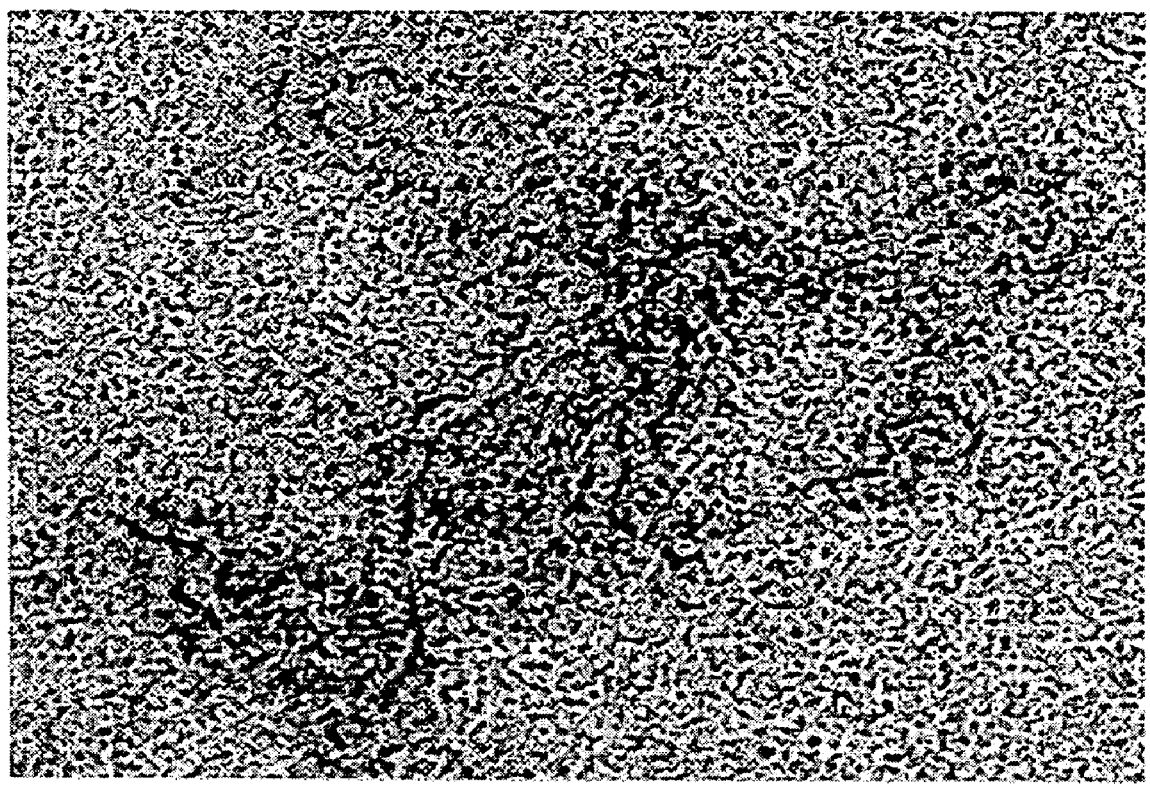
FIG. 9. Cryo-transmission electron micrograph of micellar structures formed by the self-assembly of 20 in basic aqueous solution at pH 9-10 (diameter about 70 Å).

Preliminary cryo-TEM investigations on the aggregation properties of 20 revealed the formation of thin aggregates in basic solutions at pH 9-10. Similar to carbon nanotubes, the self-assemblies showed diameters of about 70 Å and are very long (FIG. 9). The diameters are comparable with those of micelles formed from structurally related dendritic polycarboxylic fullerene derivatives.[1] At neutral and acidic pH no aggregates were observed by TEM. This is possibly due to electrostatic repulsion between individual highly charged molecules and the fact that the addends carrying the amino termini are very long and can wrap around the whole molecule and shield the apolar moieties from the water phase (monomolecular micelles).

Figure 12:
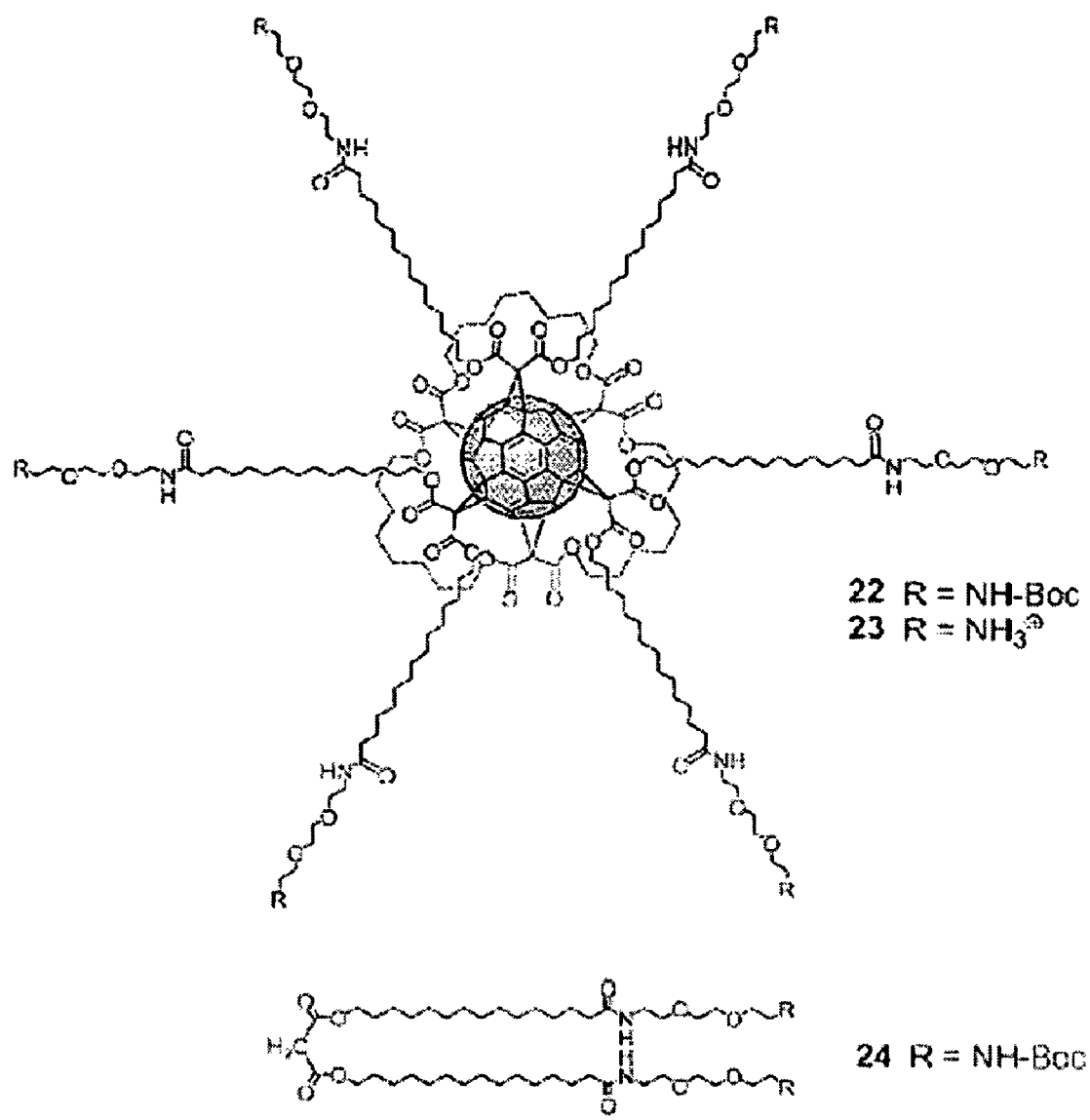
FIG. 12. Representations of compounds 22, 23, and 24, as described in Example 1.

Using the same synthetic pathway the Boc-protected hexakisadduct 22 and the sixfold protonated amphifullerene 23 with shorter hydrophilic malonate branches were prepared by reaction of eee-trisadduct 18 with an excess of malonate 24. (FIG. 12) The isolated yield of 22 after chromatographic purification was 55%. The cleavage of the protection groups was achieved with TFA and the protonated amphifullerene 23 was isolated as yellow solid in quantitative yield. All reaction intermediates and products were fully characterized by $^1H$- and $^{13}C$-NMR-, and IR- or UV/Vis-spectroscopy as well as by mass spectrometry.

Figure 15:
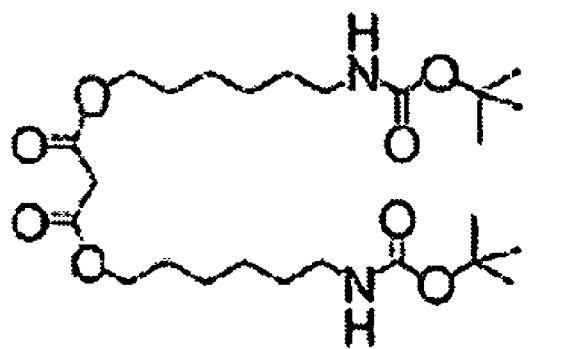
FIG. 15. Representations of compounds 33, 34, 35, and 36, as described in Example 1.
Figure 15:
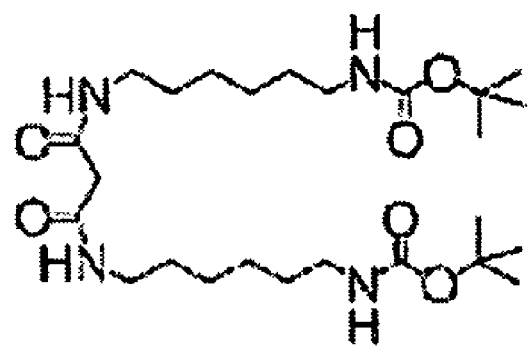
Figure 15:
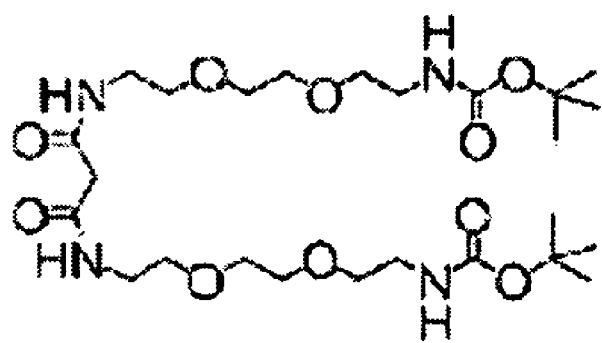
Figure 15:
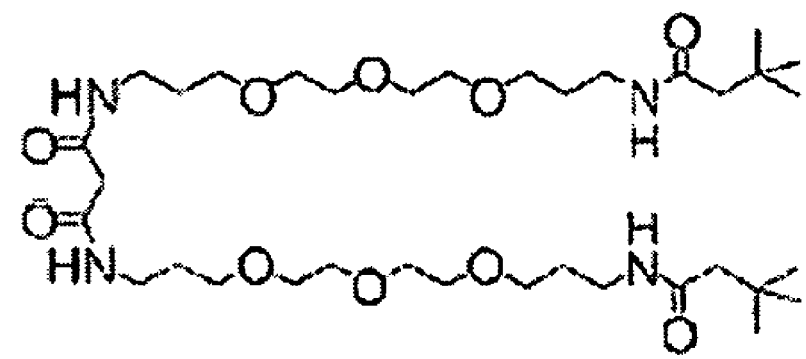

In a similar way a number of related amphiphilic mixed [3:3]-hexakisadducts 25-32 were synthesized by cyclopropanation of e,e,e-trisadduct 18 with a variety of malonate and malonamide addends 33-36 containing either alkyl- or oligoethylene glycol chains (FIG. 15). Compared to the previous example all these chains are considerably shorter and match in size with the non-polar cyclo-[3]-octylmalonate part of the resulting amphiphiles. The N-Boc-protected malonate 33 was obtained in 72% yield by condensation of malonic acid with an excess of commercially available N-Boc-protected 6-aminohexan-1-ol in the presence of DMAP and DCC. The corresponding conversion of the mono-N-protected α,ω-diamines hexamethylene diamine, 3,6-dioxa-1,8-octane diamine and 4,7,10-trioxa-1,13-tridecane diamine with malonic acid applying the same reaction conditions afforded the Boc-protected malonamides 34, 35 and 36, respectively, in comparable yields.

Figure 13:
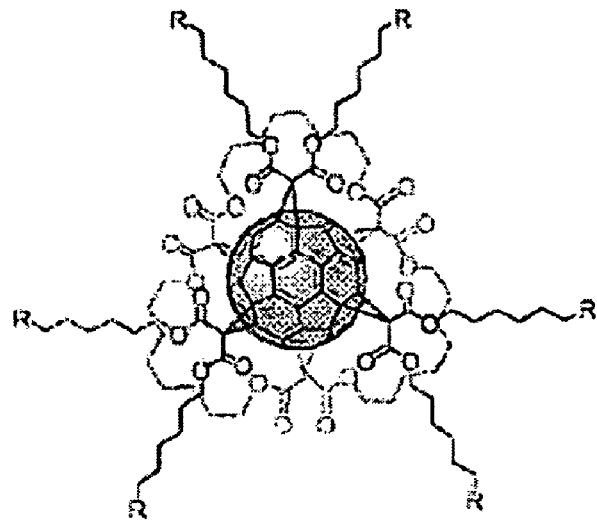
FIG. 13. Representations of compounds 25, 26, 29, and 30, as described in Example 1.
Figure 13:
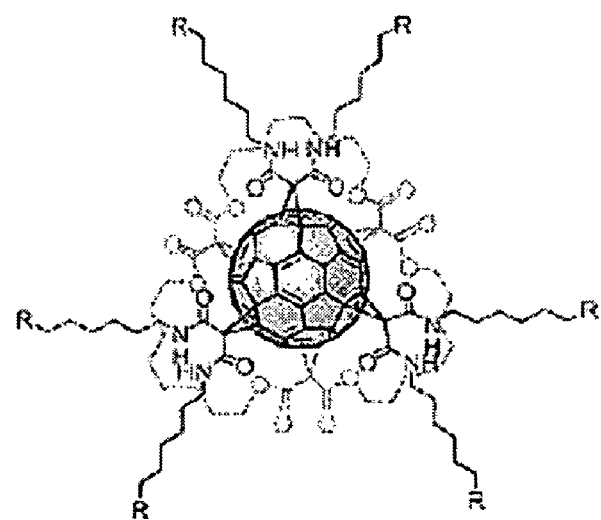
Figure 14:
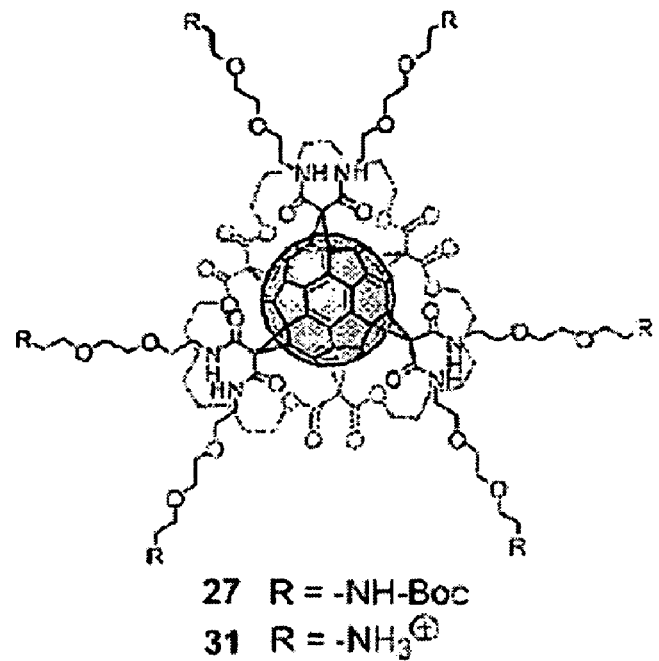
FIG. 14. Representations of compounds 27, 28, 31, and 32, as described in Example 1.
Figure 14:
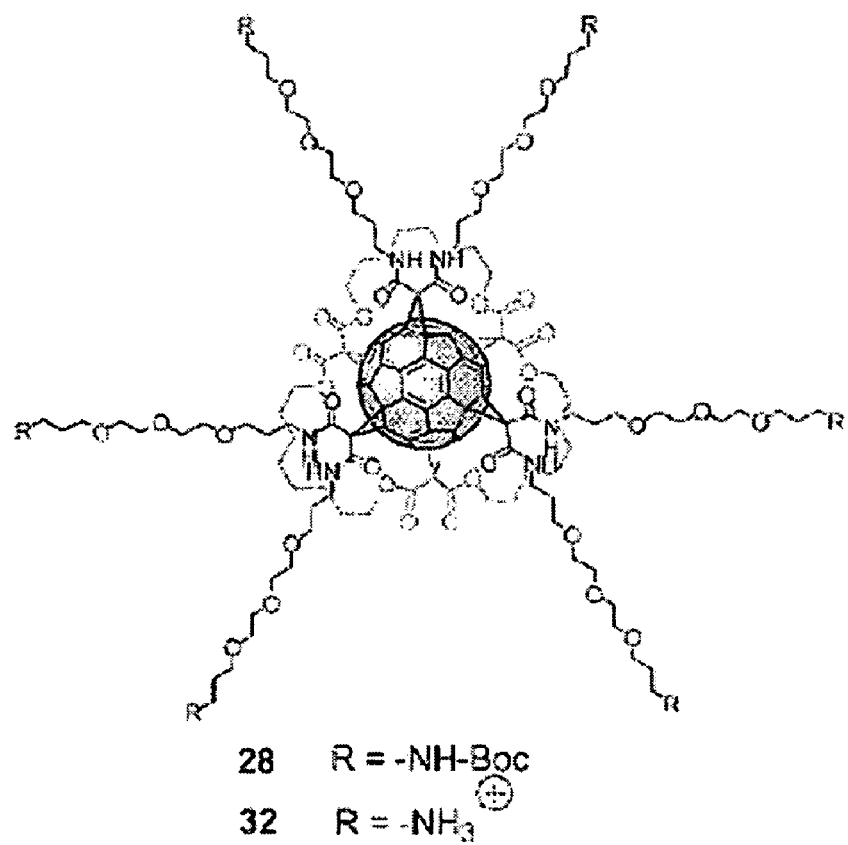

The subsequent cyclopropanation of 18 with an excess of the malonyl derivatives 33-36 in the presence of DMA, $CB_{r4}$ and DBU[12] yielded the N-Boc-protected mixed [3:3]hexakisadducts 25-28 in 50, 28, 45 and 49% yield, respectively, after chromatographic purification. The protecting groups were removed with TFA in $CH_2Cl_2$ and the hexaammonium trifluoroacetates 29-32 isolated as yellow solids in quantitative yield. (FIGS. 13-14)

The malonate and malonamide spacers as well as the N-protected [3:3]-hexakisadducts and the corresponding hexaammonium trifluoroacetates were fully characterized. The FAB mass spectra of the Boc-protected [3:3]-hexakisadducts 25, 26, 27, and 28 revealed in all cases the $M^+$ molecular ions and the $[M-6 Boc]^+$ fragment signals. The fullerene part in the $sp^2$-region of the $^{13}C$ NMR spectra of all new hexakisadducts 25-32 consists of 16 resonances grouped in two characteristic sets of signals[6] for the fullerene $sp^2$-C atoms at δ=141 and 145. This clearly reflects the expected $C_3$-symmetry within an octahedral addition pattern. The UV/Vis spectra of 25-32 show the characteristic features of octahedral malonate adducts of $C_{60}$.[6] Microscopic studies on self-assembling properties and aggregation behavior of the synthesized compounds are currently under way. Pulse-field gradient nuclear magnetic resonance (PGSE) provides a powerful tool for measuring translational motion in solution and as a consequence to determine molecular and particle dimensions.[17] From these measurements, particle sizes in $D_2O$ solution of 11.0 and 3.5 nm diameter were obtained for the hexammonium triflates 30 and 31, respectively.

Anionic [3:3]-Mixed Hexaadduct Amphifullerene 37

Figure 4:
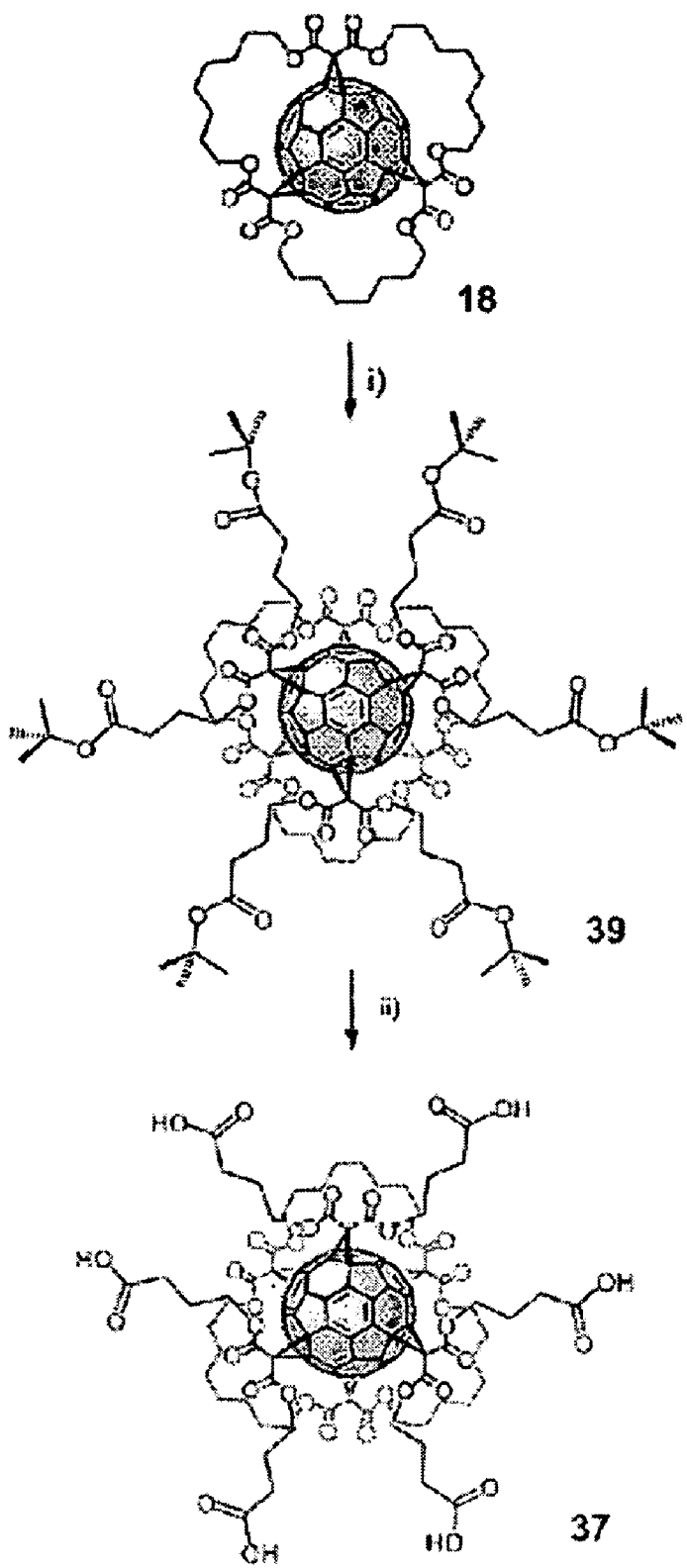
FIG. 4. Synthesis of the amphiphilic [3:3]-hexakisadduct 37 (i: DMA, malonate 38, $CBr_4$, DBU; ii: TFA, $CH_2Cl_2$).

Extending this concept of mixed [3:3]-hexakisadducts containing an cyclo-[3]-octylmalonate addend as lipophilic moiety, the amphifullerene 37 was synthesized, which after deprotonation of its carboxylic termini can easily be transferred into an anionic amphiphile. The synthesis of 37 is depicted in FIG. 4. For the introduction of the corresponding hydrophilic addends the malonate 38 was allowed to react with trisadduct 18 by means of the DMA-template mediation technique[7] to give precursor hexakisadduct 39. Only very little of tetra- and pentakisadducts were formed as side products. The separation of these lower adducts was achieved by FC and resulted in analytically pure 39 in 64.7% yield. The cleavage of the protecting tert-butyl ester groups with TFA in dichloromethane afforded the water-soluble hexaacid-hexakisadduct 37 in quantitative yield. Complete structural characterization of the reaction products was carried out by $^1$H and $^{13}$C NMR-, and IR- or UV/Vis spectroscopy as well as by mass spectrometry.

Figure 10:
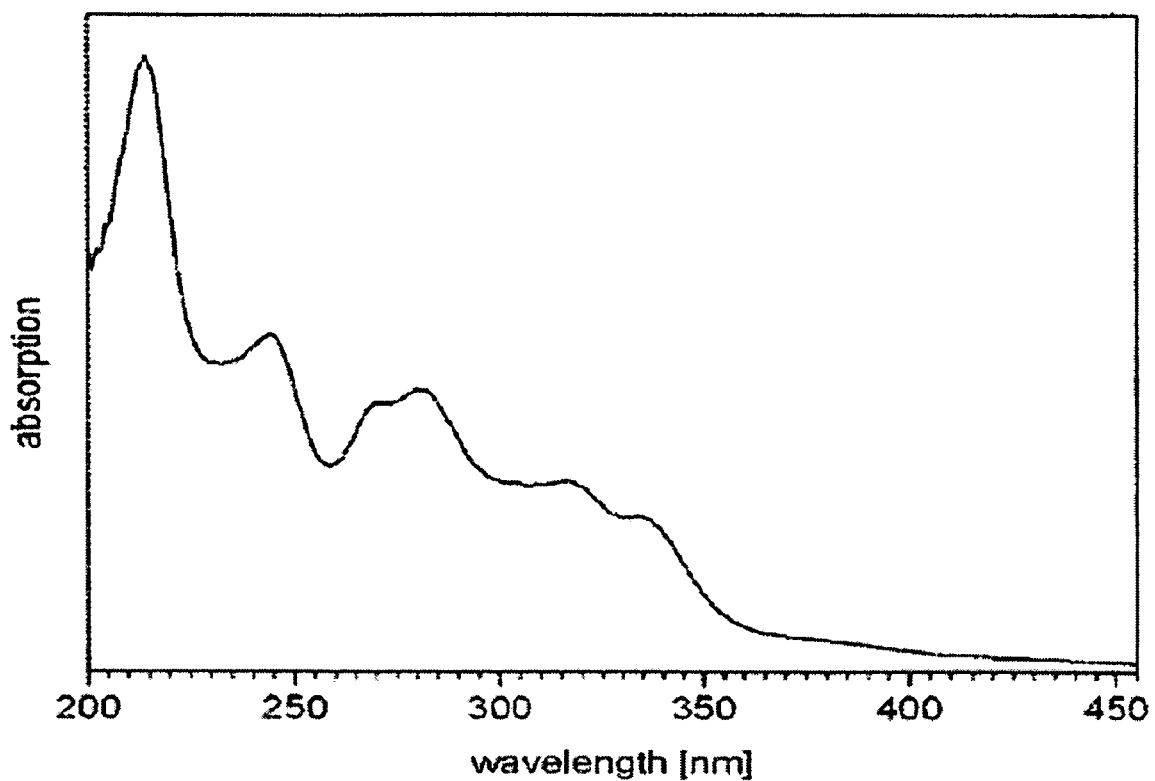
FIG. 10. The UV/Vis spectrum of 34 in phosphate buffered $H_2O$ at pH 7.2 (Shimadzu UV-3102 PC).

The UV/Vis spectrum of 37 was measured in phosphate buffered $H_2O$ at pH 7.2 and is shown in FIG. 10. The use of water as solvent allows for the detection of all absorption bands characteristic for octahedral hexakismalonate of $C_{60}$[6] including the high energy absorption at 210 nm. This absorption is usually obscured if an organic solvent is used.

In phosphate buffer at a pH value of 7.2 the solubility of the hexaacid 37 was determined to be 2.1 mg/mL. For comparison, the solubility under the same conditions of dendrofullerene hexakisadduct 1 which has a considerably higher molecular weight is 2.5 mg/mL.[18] The yellow solution of 37 at neutral pH appeared opalescent, indicating the formation of aggregates. Cryo-TEM investigations are in progress to elucidate the structure of these aggregates.

[3:3]-Amphifullerenes with Short Peptide Sequences

Figure 5:
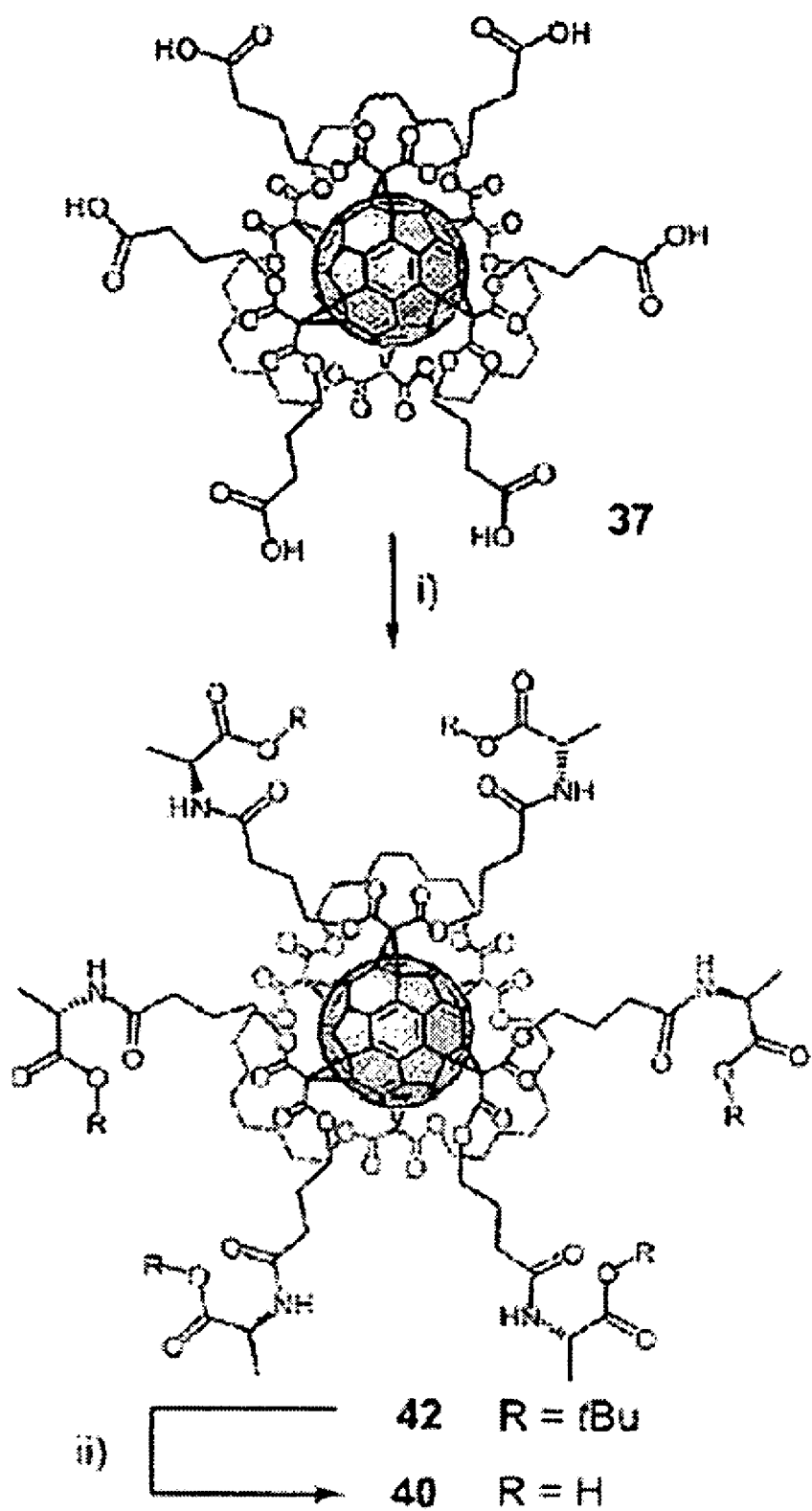
FIG. 5. Synthesis of the amphiphilic [3:3]-hexakisadduct 40 (i: DCC, NHS, L-alanine tert-butyl ester 41, THF abs, 14 h; ii: TFA, $CH_2Cl_2$). Only one of the possible diastereomers is represented.

The hexaacid 37 does not only represent an example of a water-soluble amphifullerene whose amount of negative charges and therefore its aggregation properties can be switched by changing the pH, it is also susceptible for further functionalization. For example, the coupling of the carboxy termini with peptides or other biomolecules is conceivable. As a consequence, not only the supramolecular behavior of the corresponding amphifullerenes can be further influenced but also additional molecular recognition phenomena as well as a biocompatibilization of micelles or liposomes can be introduced. As a first example the synthesis of the sixfold L-alanine decorated [3:3]-amphifullerene 40 was carried out. For this purpose, hexaacid 37 was first treated with enantiomerically pure L-alanine tert-butyl ester 41 in the presence of DCC and N-hydroxy succinimide (NHS) to afford the coupling product 42 in 62% yield after FC purification ($SiO_2$, $CH_2Cl_2$:MeOH=97:3) (FIG. 5). The tert-butyl protecting groups were removed with TFA in dichloromethane and the hexa-L-alanine amphifullerene 40 was obtained almost quantitatively as a dark yellow solid. Compounds 40 and its tert-butyl protected precursor 42 were fully characterized by IR-, UV/Vis-, $^1$H and $^{13}$C NMR spectroscopy and FAB mass spectrometry. Because of the chirality of the amino acid as well as the inherent chirality of mixed [3:3]-hexakisadducts of $C_{60}$ the formation of mixtures of diastereomers is expected. As a consequence all NMR signals should in principle split into at least two sets of signals. However, in no case multiple signals for diastereomeric splitting could be observed. This is probably due to the fact that the chiral centers within the polar addends are located in a fairly remote position relative to the chiral fullerene core. Also separation of the diastereomers using DC and HPLC was not possible. The deprotected amphifullerene 40 is very soluble in THF, DMSO and water at pH=7.2 and completely insoluble in organic solvents such as $CH_2Cl_2$ and $CHCl_3$.

Figure 16:
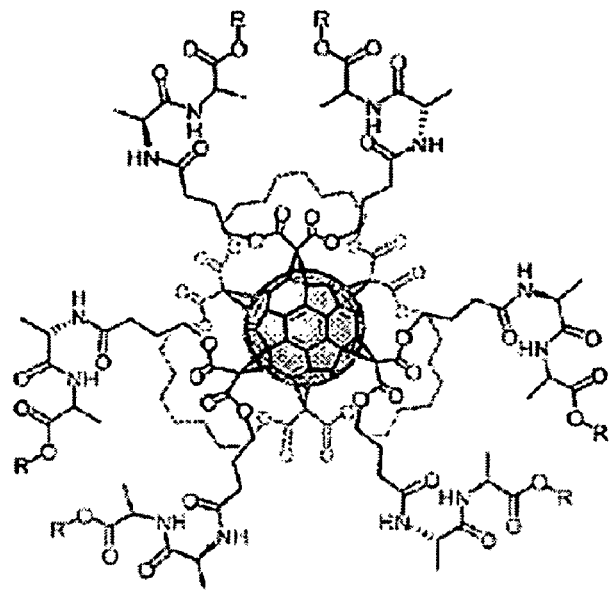
FIG. 16. Representations of compounds 45, 46, 47, and 48, as described in Example 1.
Figure 16:
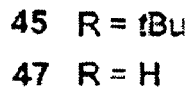
Figure 16:
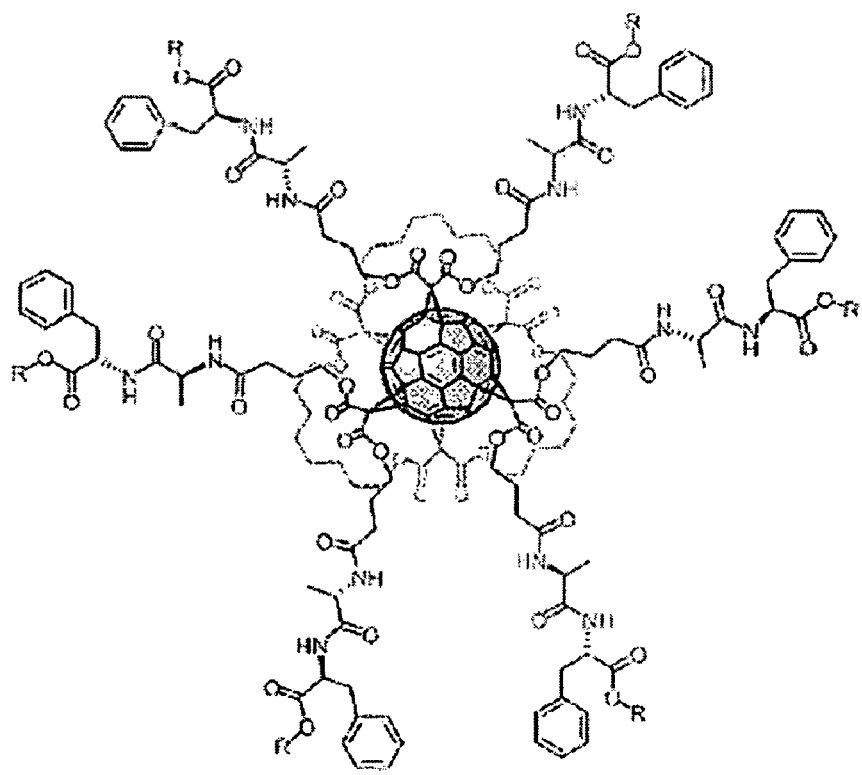
Figure 16:
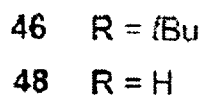
Figure 17:
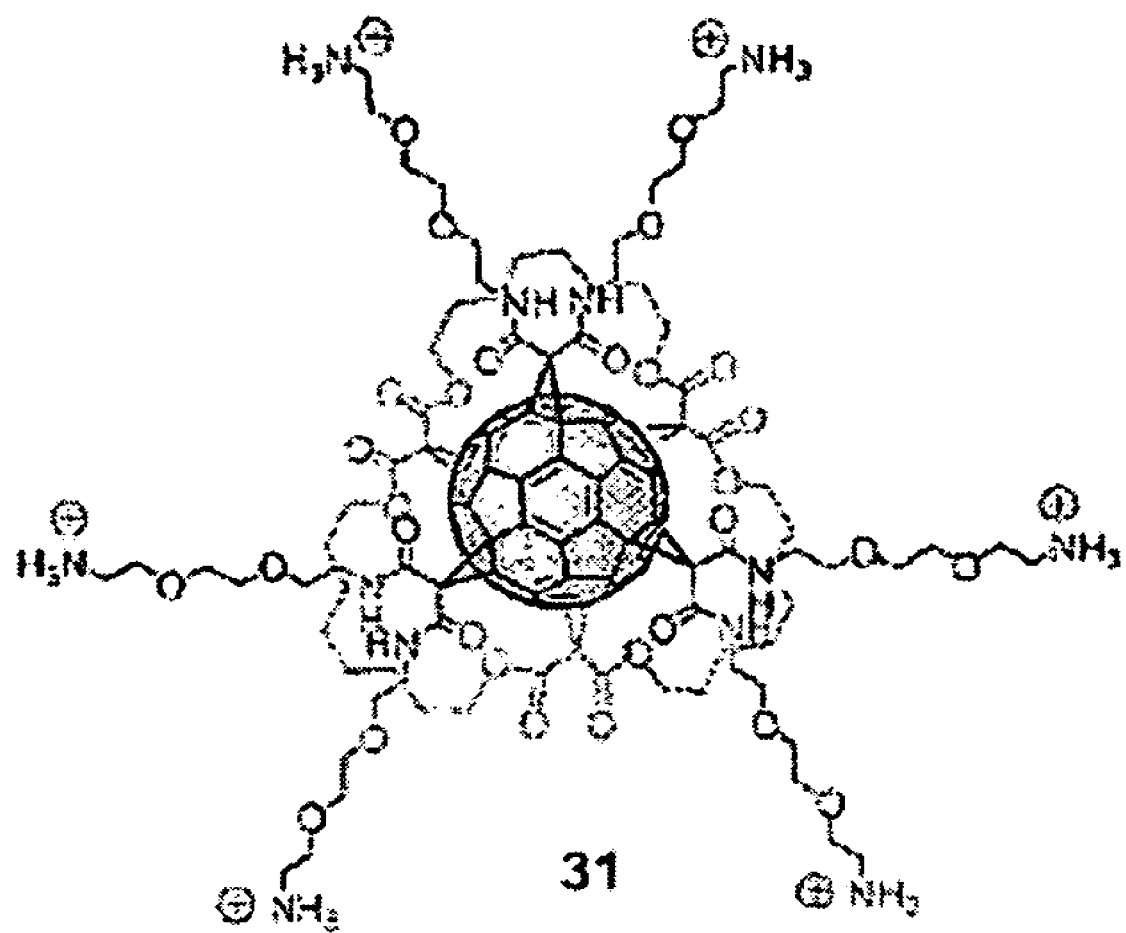
FIG. 17. Representation of compounds 31, as described in Example 1.
Figure 18:
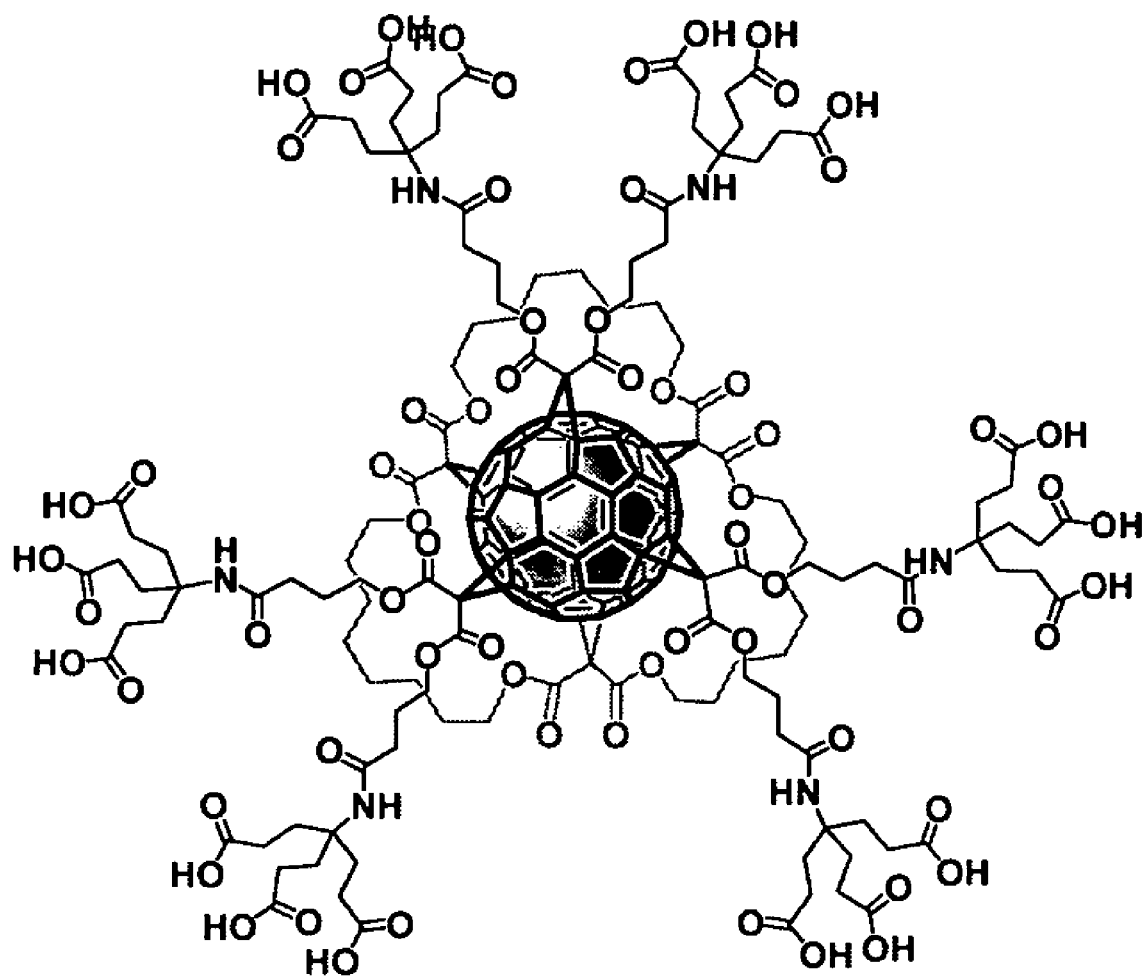
FIG. 18. Representation of a [3:3]-hexakisadduct fullerene of the present invention.
Figure 19:
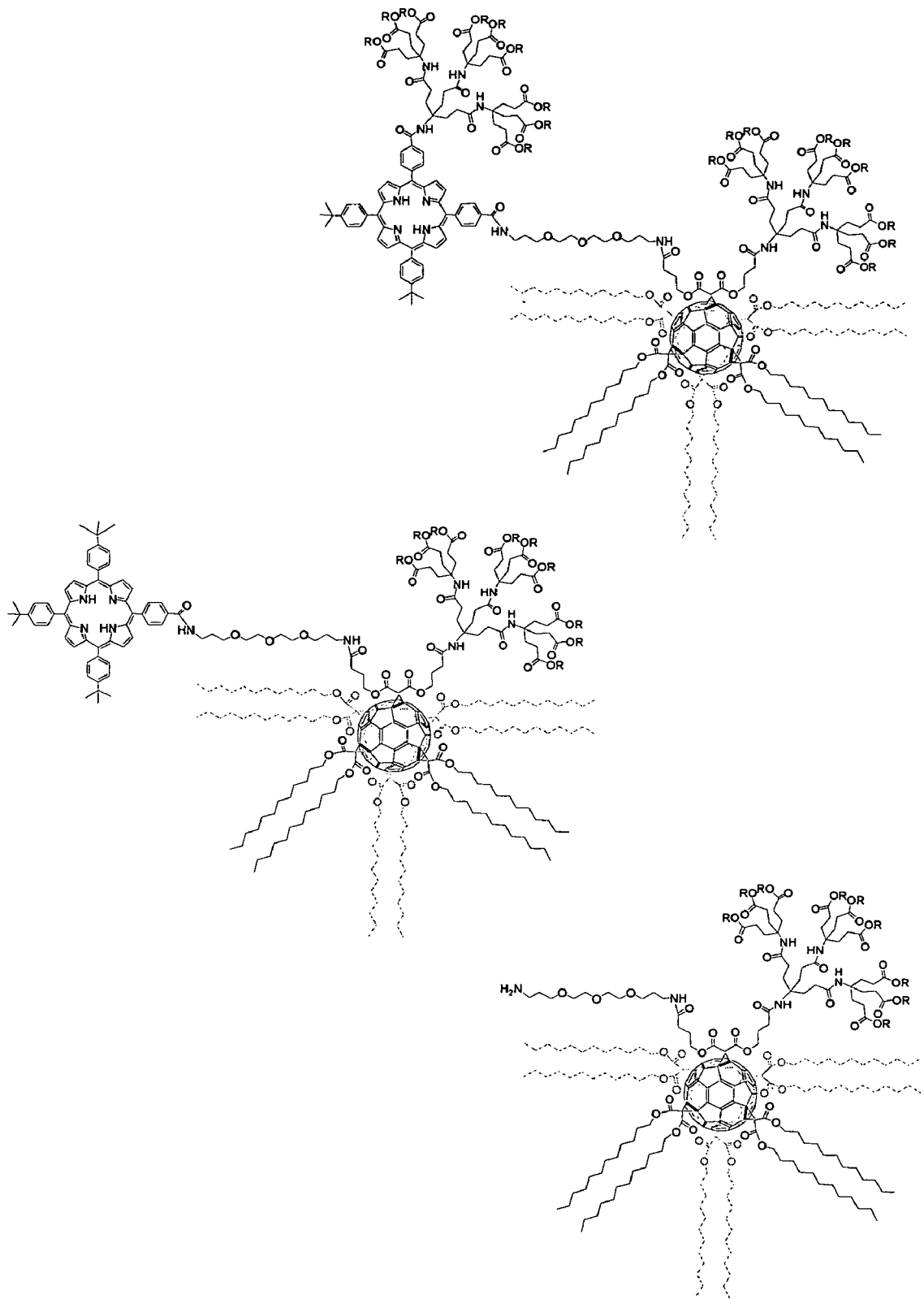
FIG. 19. Representation of three [5:1]-hexakisadduct fullerenes of the present invention.

The corresponding coupling of 37 with L-N-(L-alanyl)-alanin-tert-butyl ester 43 and L-N-(L-alanyl)-phenylalanin-tert-butyl ester 44 afforded the tert-butyl protected hexakisdipeptides 45 and 46 in 64% and 48% yield, respectively. After deprotection with TFA/$CH_2Cl_2$ at RT the $C_3$-symmetrical amphifullerenes 47 and 48 were obtained as mixture of diastereomers in quantitative yields. (FIG. 16)

The characterization of the protected dipeptide hexakisadduct precursors 45 and 46 as well as the free dipeptide hexakisadducts 47 and 48 succeeded by IR-, UV-, $^1$H and $^{13}$C NMR and by FAB mass spectroscopy. The deprotected peptidoamphifullerenes 47 and 48 exhibited a solubility behavior related to that of 40.

Conclusion and Outlook

The synthesis of a series of mixed amphiphilic hexakisadducts of $C_{60}$ with an octahedral addition pattern is now described. The new [5:1]-hexakisadduct 3 involving five nonpolar long chain malonate addends and one polar addend with two biotin termini is insoluble in water. As a consequence it cannot be used for the investigation of superstructures in aqueous solution. However, it represents an attractive building block for a potential co-surfactant aided assembly to mixed micelles or liposomes. The spacer carrying the biotin termini was designed in a way that it can protrude through a layer of assembled lipid molecules such as DPPC. This in principle makes it available for targeting of micelles and liposomes via avidin mediated binding of label molecules. This is believed to be the first report of the synthesis of amphiphilic [3:3]-hexakisadducts of $C_{60}$. The key for the very facile access to these aesthetically pleasing molecules is the easy synthesis of the e,e,e-trisadduct 18, which can be prepared in one step from the highly regioselective addition of cyclo-[3]-octylmalonate 17. The remaining three octahedral sites are available for the attachment of three ionic or neutral polar addends. As termini carboxy, amino and peptide moieties were used. This allows for the introduction of a tunable number of positive or negative charges within the polar groups by pH-variation. In a few cases preliminary investigations on the self-assembly using cryo-TEM and PGSE-NMR have been carried out. It has been shown that the solubility and self-assembly properties depend on the number of ionic charges and therefore on the pH value. These are very favourable opportunities for the controlled encapsulation and release of non-polar guest molecules making such amphiphilic fullerenes interesting candidates for drug delivery systems. Extensive investigations on the aggregation and inclusion properties of amphiphilic [3:3]-hexakisadducts of $C_{60}$ are currently under way.

Experimental Section

General Remarks:

Chemicals: $C_{60}$ was obtained from Hoechst AG/Aventis and separated from higher fullerenes by a plug filtration.[19,20] All analytical-reagent grade solvents were purified by distillation. Dry solvents were prepared using customary literature procedures.[21]

Thin Layer Chromatography (TLC): Riedel-de-Haën silica gel $F_{254}$. and Merck silica gel 60 $F_{254}$. Detection: UV lamp, $H_3[P(Mo_3O_{10})_4]$/$Ce(SO_4)_2$/$H_2SO_4$/$H_2O$ bath, $KMnO_4$/$H_2O$ and iodine chamber.

Flash Chromatography (FC): ICN Silica 32-63, 60 Å; typical parameters for column diameter, loading, optimum eluant mixtures, eluant flow rate etc. were selected from the literature.[22]

High Performance Liquid Chromatography (HPLC): Shimadzu Liquid Chromatograph LC-10AT with System Controller SCL-10AVP, Preparative Liquid Chromatographs LC-8A, Diode Array Detector, Auto Injector, Refractive Index Detector and UV/Vis Detector, Selection Valve and Fraction Collector. Analytical Columns: Nucleosil 5 μm, 200×4 mm, Macherey-Nagel; Gromsil 100 Si, NP1, 5 μm, 200×4 mm; Rexchrom Buckyclutcher 10×250 mm, Regis; and Nucleogel GFC 500-5, Macherey-Nagel. Preparative Columns: Nucleosil 5 μm, 250×21 mm, Macherey-Nagel; Grom-Sil 100 Si, NP1, 5 μm, 250×20 mm; Nucleogel GFC 500-10, Macherey-Nagel; Buckyclutcher 250×21 mm.

NMR Spectra: JEOL JNM EX 400 and JEOL JNM GX 400 ($^1$H: 400 MHz, $^{13}$C: 100.5 MHz), Bruker AVANCE 300 ($^1$H: 300 MHz, $^{13}$C: 75.4 MHz), Bruker AVANCE 400 ($^1$H: 400 MHz, $^{13}$C: 100.5 MHz). The chemical shifts are given in [ppm] relative to SiMe$_4$ (TMS). The resonance multiplicities are indicated as s (singlet), d (doublet), t (triplet), q (quartet) and m (multiplet), broad resonances as br.

UV/Vis Spectra: Shimadzu UV-3102 PC, UV-VIS-NIR Scanning Spectrophotometer; absorption maxima $\lambda_{max}$ are given in [nm].

IR Spectra: Broker FT-IR Vector 22, KBr pellets or thin film (NaCl plates), ν values in cm$^{-1}$.

Mass Spectra: Micromass Zabspec, FAB (LSIMS) mode (3-nitrobenzylalcohol) and ESI mode; Varian MAT 311A EI mode.

Freeze Fracture Transmission Electron Microscopy: Freeze fracturing and replication were performed with a Balzers BAF 400 Freeze-etch device. The replicas were examined in a Zeiss EM 902 transmission electron microscope using 80 kV accelerating voltage.[23]

15-Hydroxypentadecanoic Acid (5): Pentadecanolide 4 (2.56 g, 10.7 mmol) was dissolved in 25 mL ethanol at 50° C. An aqueous 1 M NaOH solution (11.75 mL, 11.80 mmol) was added and stirred at 50° C., until TLC control (SiO$_2$, CH$_2$Cl$_2$: ethyl acetate=95:5; $R_{f(5)}$=0.28) showed the complete hydrolysis of the lactone. The ethanol was evaporated and the remaining alkaline solution washed with CH$_2$Cl$_2$. After neutralization with 1 M HCl the product was digested in CH$_2$Cl$_2$, the aqueous layer removed and the solvent CH$_2$Cl$_2$ evaporated off. Drying in vacuo gave 2.64 g (96%) of a white powder.—$^1$H NMR (400 MHz, RT, CDCl$_3$): δ=5.99 (br, 2H) (in DMSO-d$_6$ at 4.34 and 11.97, resp.), 3.64 (t, $^3$J=6.6 Hz, 2H), 2.33 (t, $^3$J=7.40 Hz, 2H), 1.53-1.67 (m, 4H), 1.22-1.40 (m, 20H).—$^{13}$C NMR (100.5 MHz, RT, CDCl$_3$): δ=178.9 (1C), 63.1 (1C), 34.0 (1C), 32.8 (1C), 29.5, 29.5, 29.4, 29.3, 29.1, 29.0 (9C), 25.7 (1C), 24.7 (1C).—IR (KBr): ν=3455, 3305, 2918, 2850, 2616, 1712, 1472, 1406, 1294, 1269, 1248, 1226, 1204, 1186, 1059, 1021, 926, 719, 596, 494 cm$^{-1}$.

Monoprotected 1-N-Boc-1,13-Diamino-4,7,10-trioxatridecane (6): Bis-(3-aminopropyl)diethyleneglycol (26.85 g, 26.7 mL, 122 mmol) was dissolved in 1,4-dioxane (50 mL) and a 30 mL solution of 4.37 g Boc-anhydride (23.5 mmol) in dioxane added dropwise within 5 h at room temperature.[24] The mixture was stirred for additional 5 h and then evaporated. The resulting yellowish oil was digested in water (50 mL) and extracted four times with CH$_2$Cl$_2$ (50 mL each). The organic phases were pooled and washed four times with saturated NaCl solution (30 mL each). The extraction procedure and the subsequent washing were repeated. The resulting organic solution was dried over MgSO$_4$, which subsequently was filtered off to give an almost colorless oil after evaporation and drying in vacuo (6.70 g, 89% rel. to BocO$_2$). TLC control (SiO$_2$, CH$_2$Cl$_2$:EtOH=9:1) indicated only traces of doubly protected diamine ($R_f$=0.95) and no starting material.—$^1$H NMR (400 MHz, RT, CDCl$_3$): δ=5.12 (br, 1H), 3.64-3.60, 3.60-3.55, 3.55-3.49 (3m, 12H), 3.20 (dt, $^3$J$_1$=$^3$J$_2$=6.1 Hz, 2H), 2.81 ("dt", $^3$J$_1$=6.7 Hz, $^3$J$_2$=1.7 Hz, 2H), 2.06 (br, 2H), 1.78-1.69 (m, 4H), 1.41 (s, 9H).—$^{13}$C NMR (100.5 MHz, RT, CDCl$_3$): δ=155.80 (1C), 78.40 (1C), 70.32, 70.28, 69.93, 69.90, 69.15 (6C), 39.31 (1C), 38.14 (1C), 33.05 (1C), 29.36 (1C), 28.17 (3C).—IR (Film/KBr): ν=3362, 2930, 2868, 1708, 1524, 1456, 1391, 1365, 1252, 1173, 1113, 1043, 944, 865 cm$^{-1}$.—MS (EI, 40° C.): m/z=320 [M]$^+$, 247, 177, 164, 146, 102, 89, 74, 57, 44.

13-N-Boc-13-Amino-4,7,10-trioxatridecyl 15-Hydroxypentadecanoylamide (7): 440 mg (1.70 mmol) hydroxyacid 5 was dissolved in 25 mL dry DMF and 290 mg (1.79 mmol) CDI added under N$_2$-protection at RT. The imidazolide formation was completed after several minutes. A solution of 545 mg (1.70 mmol) of amine 6 in 5 mL dry CH$_2$Cl$_2$ was prepared, and the imidazolide solution was added via a dry syringe/septum under nitrogen. The combined solutions were stirred for 2 h, washed with saturated aqueous NaCl solution (three times 5 mL each) and dried over MgSO$_4$. Purification by FC on silica (CH$_2$Cl$_2$:EtOH=95:5) gave 675 mg 7 as a white solid (yield 70%).—$^1$H NMR (400 MHz, RT, CDCl$_3$): δ=6.25, 4.98 (2br, 2H), 3.66-3.48 (m, 14H), 3.34 (dt, 2H), 3.20 (dt, 2H), 2.12 (t, $^3$J=7.7 Hz), 1.98 (br, 1H), 1.74 (m, 4H) 1.64-1.49 (m, 4H), 1.41 (s, 9H), 1.36-1.18 (m, 20H).—$^{13}$C NMR (100.5 MHz, RT, CDCl$_3$): δ=173.1 (1C), 156.0 (1C), 78.9 (1C), 70.5, 70.1, 70.1, 69.5 (6C), 62.9 (1C), 38.4, 37.8 (2C), 36.8 (1C), 32.7 (1C), 29.6, 29.5, 29.5, 29.4, 29.3, 29.3, 28.9 (9C), 28.4 (3C), 25.7, 25.7 (2C).—IR (Film/KBr): ν=3321, 3064, 2921, 2850, 1686, 1636, 1535, 1471, 1421, 1366, 1277, 1250, 1179, 1139, 1061, 997, 867, 783, 721, 632, 578 cm$^{-1}$.—MS (FAB): m/z=693 [M+Cs]$^+$, 583 [M+Na]$^+$, 561 [M]$^+$, 461 [M-Boc]$^+$, 298.

Bis(29-N-Boc-29-Amino-16-aza-20,23,26-trioxa-15-oxononacosyl) Malonate (8): 104 mg (1 mmol) of malonic acid and 1.23 g (2.2 mmol) of alcohol 7 were dissolved in dry CH$_2$Cl$_2$ under N$_2$ protection and the solution cooled in an ice bath. 41.0 mg (0.20 mmol) DMAP (10 mol %) and 454 mg (2.20 mmol) DCC were added subsequently. After stirring under N$_2$-protection for 15 min at 0° C. and 2 h at RT, TLC control showed complete conversion of the starting material. Dicyclohexyl urea formed during the reaction precipitated and was filtered off. Traces of urea were subsequently removed by repeated precipitation from ethyl acetate. After evaporation of the solvent and purification by FC on silica (CH$_2$Cl$_2$:EtOH=94:6) 714 mg of a white solid was obtained (yield 60%).—$^1$H NMR (400 MHz, RT, CDCl$_3$): δ=6.22, 4.97 (2br, 4H), 4.11 (t, $^3$J=6.8 Hz, 4H), 3.66-3.48 (3m, 12H), 3.34 (s, 2H), 3.33 (dt, 4H), 3.20 (dt, 4H), 2.11 (t, $^3$J=7.6 Hz, 4H), 1.74 (m, 4H), 1.60 (m, 4H), 1.41 (s, 18H), 1.35-1.19 (m, 40H).—$^{13}$C NMR (100.5 MHz, RT, CDCl$_3$): δ=172.9 (2C), 166.4 (2C), 155.8 (2C), 78.9 (2C), 70.5, 70.5, 70.2, 70.1, 70.1, 69.5 (12C), 65.6 (2C), 41.7 (1C), 38.6, 37.9 (4C), 36.9 (2C), 29.7, 29.7, 29.6, 29.6, 29.5, 29.4, 29.3, 29.1 (20C), 28.5 (6C), 25.9, 25.8 (4C).—IR (Film/KBr): ν=3312, 3082, 2919, 2851, 1747, 1719, 1685, 1640, 1543, 1468, 1390, 1366, 1347, 1251, 1182, 1127, 1021, 997, 867, 720, 694, 603 cm$^{-1}$.—MS (FAB): m/z=1322 [M+Cs]$^+$, 1212 [M+Na]$^+$, 1190 [M]$^+$, 1190, 990, 443.

1,2-{Bis-(14-[3-{2-(2-[N-Boc-Aminopropoxy]-ethoxy)-ethoxy}-propyl]-carbamoyl-tetradecyloxycarbonyl)-methano}-1,2-dihydro[60]fullerene (9): 255 mg (0.35 mmol) C$_{60}$ were dissolved in 150 mL dry toluene under vigorous stirring. Subsequently 64.0 mg (0.193 mmol) CBr$_4$ and 208 mg (0.175 mmol) malonate 8 were added. Afterwards 29.3 mg (0.193 mmol) DBU were dissolved in toluene and added dropwise over a period of 1 h at RT. After 2 h additional stirring and TLC control, the reaction mixture was separated by FC on silica with toluene. The unreacted C$_{60}$ was eluted first (toluene:EtOH=9:1, $R_{f(9)}$=0.25), and 137 mg of a brown solid 9 (yield 41%) were obtained after drying in high vacuum.—$^1$H NMR (400 MHz, RT, CDCl$_3$): δ=6.38, 4.94 (2br, 2H), 4.48 (t, $^3$J=6.6 Hz, 4H), 3.66-3.49 (3m, 24H), 3.35

(dt, 4H), 3.21 (dt, 4H), 2.15 (t, $^3J$=7.7 Hz, 4H), 1.88-1.70 (2m, 12H), 1.65-1.55 (m, 4H), 1.43 (s, 18H), 1.38-1.16 (m, 20H).—$^{13}$C NMR (100.5 MHz, RT, CDCl$_3$): δ=173.3 (2C), 163.6 (2C), 156.0 (2C), 145.3, 145.2, 145.1, 144.8, 144.6, 144.6, 144.5, 143.8, 143.0, 142.9, 142.2, 141.9, 140.9, 138.9 (58C, C$_{60}$ sp$^2$), 79.0 (2C), 71.6 (2C), 70.5, 70.5, 70.2, 70.1, 70.0, 69.5 (12C), 67.5 (2C), 52.4 (1C), 38.6, 37.9 (4C), 36.7 (2C), 29.6, 29.6, 29.6, 29.4, 29.4, 29.2, 28.9, 28.6 (14C), 28.4 (6C), 26.0, 25.8 (4C).—IR (KBr): ν=3319, 2921, 2851, 1747, 1714, 1686, 1637, 1540, 1471, 1383, 1366, 1254, 1175, 1118, 798, 526 cm$^{-1}$.—UV/Vis (CH$_2$Cl$_2$): λ$_{max}$=256, 320, 425.—MS (FAB): m/z=1907 [M]$^+$, 1807, 1709, 1652, 720.

1,2-{Bis-(14-[3-{2-(2-[N-Boc-Aminopropoxy]-ethoxy)-ethoxy}-propyl]-carbamoyl-tetradecyloxycarbonyl)-methano}-18,36:22,23:27,45:31,32:55,60-pentakis-{di(10,12-octadecadiynyloxycarbonyl)-methano}-1,2:18,36:22,23:27,45:31,32:55,60-dihydro[60]fullerene (12): Similar to the preparation of C$_{60}$ hexakisadducts,$^{[6,7,14]}$ 53.0 mg (34 µmol, 1 eq) mono adduct 9 was dissolved in dry and degassed toluene under nitrogen protection. A tenfold excess (70.0 mg, 10 eq) of DMA was added to the solution and stirred for 2 h at ambient temperature. 65.0 mg (10 eq) of the diyne-malonate 11$^{[13]}$ and 113 mg (10 eq) of CBr$_4$ were subsequently added. After a few minutes stirring to allow complete dissolution, 102 µL (20 eq) DBU, diluted in 10 mL dry toluene, was added dropwise over a period of 1 h. The reaction mixture was stirred under nitrogen until TLC control remained unchanged (1-3 d). The separation from DMA and side products succeeded by FC (silica, CH$_2$Cl$_2$:EtOH=95:5). A subsequent purification by HPLC (nucleosil, CH$_2$Cl$_2$:EtOH=96:4) gave 12 as a yellow solid (34.0 mg, 21%).—$^1$H NMR (400 MHz, RT, CDCl$_3$): δ=6.62, 4.96 (2br, 4H), 4.23 (t, $^3J$=6.7 Hz, 24H), 3.68-3.50 (3m, 24H), 3.37 (m, 4H), 3.21 (m, 4H), 2.23 (t, $^3J$=6.9 Hz, 44H), 1.84-1.58 (m, 36H), 1.56-1.46 (tt, 40H), 1.43 (s, 18H), 1.41-1.20 (m, 180H), 0.89 (t, $^3J$=6.7 Hz, 30H).—$^{13}$C NMR (100.5 MHz, RT, CDCl$_3$): δ=173.7 (2C), 163.8 (12C), 156.1 (2C), 145.7, 141.1 (48C, C$_{60}$ sp$^2$), 79.0 (2C), 77.5, 77.4 (20C), 70.5, 70.2, 70.1, 70.0, 69.5, 69.0 (24C), 66.9 (12C), 65.3, 65.2 (20C), 45.3 (6C), 38.9, 38.1 (4C), 36.6 (2C), 31.0, 29.7, 29.6, 29.5, 29.4, 29.4, 29.2, 29.0, 28.8, 28.4, 28.4, 28.0 (108C), 25.8 (12C, 6.36), 22.1 (10C), 19.2, 19.1 (20C), 13.9 (10C).—IR (Film/KBr): ν=3416, 2929, 2856, 2258, 2153, 1746, 1652, 1466, 1365, 1264, 1218, 1123, 1082, 716, 530 cm$^{-1}$.—UV/Vis (CH$_2$Cl$_2$): λ$_{max}$=271, 280, 316 (sh), 333 (sh).—MS (FAB): m/z=4862 [M]$^+$, 4761, 4659, 720.

1,2-{Bis-(14-[3-{2-(2-[N-Biotinyl-aminopropoxy]-ethoxy)-ethoxy}-propyl]-carbamoyltetradecyloxycarbonyl)-methano}-18,36:22,23:27,45:31,32:55,60-pentakis-{di(10,12-octadecadiynyloxycarbonyl)-methano}-1,2:18,36:22,23:27,45:31,32:55,60-dihydro[60]fullerene (3): 15.6 mg (65 µmol) of D-(+)-biotin 10 were dissolved in 2 mL dry DMF and 6 eq [6.20 mg, 38.5 µmol] DCI added under nitrogen at RT. After several minutes a solution of 1 eq of the hexakisadduct 12 (31.0 mg, 6.4 µmol, 1 eq.) in mL dry DMF was prepared and the biotin-imidazolide reaction mixture added under nitrogen via a syringe/septum. The reaction mixture was stirred for 2 h at RT and subsequently washed three times with 5 mL saturated aqueous NaCl solution each. Purification by FC on silica (CH$_2$Cl$_2$:EtOH=9:1) and HPLC gave 3 as a yellow wax-like solid (yield: 27.0 mg, 82%).—$^1$H NMR (400 MHz, RT, CDCl$_3$): δ=6.68, 6.61, 5.45, 5.30 (4br, 8H), 4.52 (m, 2H), 4.32 (m, 2H), 4.23 (t, $^3J$=6.6 Hz, 24), 3.66-3.50 (3m, 24H), 3.32 (m, 4H), 3.15 (m, 4H), 2.91 (dd, 3J1=4.8 Hz, 3J2=12.8 Hz, exoH), 2.75 (d, 3J=12.9 Hz, endo-H), 2.32 (t, 3J=7.4 Hz), 2.24 (t, 3J=7.0 Hz), 2.16 (m), 1.81-1.56 (m), 1.56-1.43 (m), 1.41-1.20 (m), 0.89 (t, 3J=7.1 Hz).—$^{13}$C NMR (100.5 MHz, RT, CDCl$_3$): δ=173.6 (4C), 163.8 (12C), 163.5 (2C), 145.7, 141.1 (48C, C60-sp2), 77.5, 77.4 (20C), 70.3, 69.9, 69.7, 69.6, 69.0 (24C), 66.9 (12C), 65.2 (20C), 62.0 (2C), 60.4 (2C), 55.3 (2C), 45.3 (6C), 40.5 (2C), 37.4, 36.8 (4C), 36.1 (2C), 33.8, 31.0 (14C), 29.7, 29.4, 29.2, 29.0, 28.8, 28.4, 28.4, 28.3, 28.0 (98C), 25.8, 24.7 (14C), 22.1 (10C), 19.2, 19.1 (20C), 13.9 (10C).—IR (Film/KBr): ν=3272, 3153, 3086, 2927, 2855, 2258, 2156, 1743, 1695, 1652, 1558, 1464, 1378, 1262, 1214, 1080, 1037, 801, 761, 715, 634 cm$^{-1}$.—UV/Vis (CH$_2$Cl$_2$): λ$_{max}$=270, 281, 317 (sh), 333 (sh).

N-Boc-Protected [5:1]-Hexakisadduct 1,2-{Bis-(14-[3-{2-(2-[N-Boc-Aminopropoxy]ethoxy)-ethoxy}-propyl]-carbamoyl-tetradecyloxycarbonyl)-methano}-18,36:22,23:27, 45:31,32:55,60-pentakis-{ethyloxycarbonyl)-methano}-1,2: 18,36:22,23:27,45:31,32:55,60-dihydro[60]fullerene (15) and Diaminoamphifullerene [5:1]-Hexakisadduct 1,2-{Bis-(14-[3-{2-(2-[Aminopropoxy]-ethoxy)-ethoxy}-propyl]carbamoyl-tetradecyloxycarbonyl)-methano}-18,36:22,23:27, 45:31,32:55,60-pentakis-{ethyloxycarbonyl)-methano}-1,2: 18,36:22,23:27,45:31,32:55,60-dihydro[60]fullerene (16): The synthesis of [5:0] pentakisadduct 14 was performed according to a literature protocol.$^{[12]}$ 32.6 mg (21.6 µmol, 1.0 eq) of 14 were dissolved in 15 mL dry toluene. 16.0 mg (48.2 µmol, 2.2 eq) CBr$_4$ and 56.4 mg (48.2 µmol, 2.2 eq) malonate 8, dissolved in toluene each, were added. 10 µL (3.1 eq) of DBU, diluted in 1 mL of toluene, were added dropwise over a period of 1 h to the stirred solution at RT. After additional stirring for 2 h and TLC control 36.7 mg (63%) [5:1]-hexakisadduct 15 was obtained as bright yellow solid after purification by HPLC (nucleosil, toluene:EtOH=92:8). The cleavage of the Boc protecting groups of 15 (32.0 mg, 11.9 µmol) was achieved in TFA/CH$_2$Cl$_2$ (5 mL/5 mL) in 30 min reaction time. Subsequently, the solvents were evaporated and the deprotected hexakisadduct 16 was digested in CH$_2$Cl$_2$ and washed with saturated NaHCO$_3$. The separated organic phase was dried over MgSO$_4$ to give 30.3 mg (89%) of diaminoamphiphile 16.

15: $^1$H NMR (400 MHz, RT, CDCl$_3$): δ=6.24, 4.97 (2br, 4H), 4.32 (q, $^3J$=7.1 Hz, 20H), 4.23 (t, $^3J$=6.8 Hz, 4H), 3.66-3.50 (3m, 24H), 3.34 (dt, 4H), 3.21 (dt, 4H), 2.13 (t, $^3J$=7.6 Hz, 4H), 1.80-1.54 (3m, 16H) 1.42 (s, 18H), 1.32 (t, $^3J$=7.1 Hz, 30H) 1.28-1.21 (m, 40H).—$^{13}$C NMR (100.5 MHz, RT, CDCl$_3$): δ=173.1 (2C), 163.9, 163.8 (12C), 156.0 (2C), 145.7, 141.1 (48C, C$_{60}$ sp$^2$), 78.9 (2C), 70.5, 70.2, 70.1, 70.0, 69.5, 69.1, 69.0 (24C), 67.0 (2C), 62.8 (10C), 45.3 (6C), 38.5, 37.8 (4C), 36.8 (2C), 29.7, 29.7, 29.6, 29.6, 29.5, 29.4, 29.4, 29.2, 29.0 (24C), 28.4 (6C), 25.8 (4C), 14.0 (10C).—UV/Vis (CH$_2$Cl$_2$): λ$_{max}$=244, 272, 281, 316, 334.—MS (FAB): m/z=2698 [M]$^+$, 2599 [M-Boc]$^+$, 2498 [M2Boc]$^+$, 1510, 1352, 1194, 1036, 720 [C$_{60}$]$^+$.

16: $^1$H NMR (400 MHz, RT, CDCl$_3$): δ=6.54 (br, 2H, 19), 4.33 (q, $^3J$=7.1 Hz, 20H), 4.24 (t, $^3J$=6.7 Hz, 4H), 3.67-3.51 (3m, 24H), 3.33 (dt, 4H), 2.85 (t, $^3J$=6.6 Hz, 4H), 2.14 (t, 4H), 1.98 (br, 4H), 1.82-1.52 (3m, 16H), 1.32 (t, $^3J$=7.1 Hz, 30H) 1.28-1.20 (m, 40H).—$^{13}$C NMR (100.5 MHz, RT, CDCl$_3$): δ=173.7 (2C), 164.3, 164.2 (12C), 146.2, 141.5 (48C, C$_{60}$ sp$^2$), 70.9, 70.8, 70.5, 70.3, 70.1, 69.5, 69.4 (24C), 67.4 (2C), 63.2 (10C), 45.7 (6C), 40.1, 38.0 (4C), 37.2 (2C), 30.1, 30.0, 29.9, 29.8, 29.7, 29.4 (24C), 28.8 (6C), 26.3 (4C), 14.4 (10C).

Biotinated [5:1]-Hexakisadduct 1,2-{Bis-(14-[3-{2-(2-[N-Biotinyl-aminopropoxy]ethoxy)-ethoxy}-propyl]-carbamoyl-tetradecyloxycarbonyl)-methano}-18,36:22,23:27, 45:31,32:55,60-pentakis-{ethyloxycarbonyl)-methano}1,2: 18,36:22,23:27,45:31,32:55,60-dihydro-[60]fullerene (13): An excess of D-(+)-biotin (58.0 mg, 0.24 mmol) was activated with CDI (38.5 mg, 0.24 mmol) in dry DMF (2 mL).

After stirring for 30 min, the coupling was performed in dry CH$_2$Cl$_2$ by adding the activated biotin to the solution of 16. FC on silica (CH$_2$Cl$_2$:EtOH=85:15) and HPLC (CH$_2$Cl$_2$:EtOH=92:8) gave 20.3 mg (60%) of 13 as a yellow solid.—$^1$H NMR (400 MHz, RT, CDCl$_3$): δ=6.41, 5.12, 4.87 (3br, 8H), 4.51 (m, 2H), 4.32 ('q', $^3$J=7.1 Hz, 22H), 4.23 (t, $^3$J=6.8 Hz), 3.70-3.42 (3m, 24H), 3.30 (m, 4H), 3.17 (m, 4H), 2.92 (dd, $^3$J$_1$=4.9 Hz, $^3$J$_2$=12.9 Hz, exo), 2.73 (d, $^3$J=12.6 Hz, endo), 2.32 (t, 4H), 2.14 (t, $^3$J=7.6 Hz, 4H), 1.90-1.53 (m, 24H), 1.45 (m, 4H), 1.32 (t, $^3$J=7.1 Hz, 30H), 1.29-1.21 (m, 40H).—$^{13}$C NMR (100.5 MHz, RT, CDCl$_3$): δ=173.5, 173.4, 163.9, 163.8, 162.8, 145.7, 141.1, 70.6, 70.3, 70.3, 70.1, 70.1, 69.8, 69.5, 69.1, 69.0, 67.0, 62.8, 61.8, 60.3, 60.0, 55.2, 45.3, 40.5, 40.1, 37.4, 36.8, 33.8, 29.7, 29.6, 29.4, 29.4, 29.2, 29.1, 28.4, 28.4, 28.2, 28.2, 25.8, 24.7, 14.0.—UV/Vis (CH$_2$Cl$_2$): λ$_{max}$=244, 270, 281, 316, 334.

N-Boc-Protected [3:3]-Hexakisadduct (19) and Hexaaminoamphiphile (20): e,e,e-Trisadduct 18 (59.0 mg, 43.5 µmol)[16,19] was dissolved in dry toluene and treated with an excess of DMA (54.0 mg, 260 µmol). After stirring for 2 h at RT, 310 mg malonate 8 (260 µmol) and 87.0 mg (260 µmol) CBr$_4$ were added subsequently and the reaction mixture was stirred for some minutes to allow complete dissolution. 79.0 mg (520 µmol, 78 µL) of DBU, diluted in 5 mL dry toluene, were added dropwise over 1 h and the solution stirred at RT and under N$_2$ protection for one more day. Purification by FC on silica (CH$_2$Cl$_2$:EtOH=95:5 to 9:1; R$_{f(19)}$=0.2 at 95:5) gave 19 as a yellow solid (118 mg, 55% yield). The cleavage of the Boc protection groups was performed in CH$_2$Cl$_2$ (5 mL) with TFA (3 mL) to result in a yellow clear solid 20 in almost quantitative yield.

19: $^1$H NMR (400 MHz, RT, CDCl$_3$): δ=6.27, 4.99 (2br, 12H), 4.67 (m, 6H), 4.30-4.10 (2m, 15H), 4.00 (m, 3H), 3.67-3.50 (3m, 72H), 3.35 (dt, 12H), 3.22 (dt, 12H), 2.14 (t, $^3$J=7.7 Hz, 12H), 1.84-1.43 (3m, 63H), 1.43 (s, 54H), 1.39-1.21 (m, 120H), 1.17 (m, 18H), 0.82 (m, 3H).—$^{13}$C NMR (100.5 MHz, RT, CDCl$_3$): δ=173.1 (6C), 163.8, 163.7, 163.6, 163.1 (12C), 156.0 (6C), 146.4, 145.9, 145.6, 145.6, 145.3, 144.9, 144.8, 142.0, 141.8, 141.8, 140.9, 140.8, 140.7, 140.6 (48C, C$_{60}$ sp$^2$), 78.9 (6C), 70.5, 70.2, 70.1, 70.0, 69.5, 69.2., 69.1 (48C), 67.0, 66.9 (12C), 46.7, 45.6 (6C), 38.5, 37.7 (12C), 36.8 (6C), 29.7, 29.7, 29.7, 29.6, 29.5, 29.4, 29.3, 29.0, 29.0 (90C), 28.4 (18C), 25.8 (12C).—UV/Vis (CH$_2$Cl$_2$): λ$_{max}$=244, 271, 282, 315, 334.—MS (FAB): m/z=4943 [M+Na]$^+$, 4920 [M]$^+$, 4820, 4621, 4316, 4096, 720.

20: $^1$H NMR (400 MHz, RT, CDCl$_3$): δ=4.64 (m, 6H), 4.32-4.07 (2m, 15H), 4.01 (m, 3H), 3.73-3.47 (3m, 72H), 3.31 (dt, 12H), 3.17 (dt, 12H), 2.55 (very broad, 18H), 2.21 (m, 12H), 2.02, 1.84-1.44 (4m, 63H), 1.41-1.21 (m, 120H), 1.18 (m, 18H), 0.87 (m, 3H).—IR (KBr): ν=3417, 3302, 3084, 2926, 2855, 1747, 1682, 1645, 1551, 1465, 1434, 1384, 1354, 1264, 1204, 1131, 1084, 874, 833, 800, 759, 721, 670, 528 cm$^{-1}$.—UV/Vis (H$_2$O/pH 7.2): λ$_{max}$=214, 244, 271, 280, 316, 334.—MS (FAB): m/z=4320 [M]$^+$, 3332 [M-diaminomalonate]$^+$, 2349 [M-2 diaminomalonates]$^+$, 720 [C$_{60}$]$^+$.

Bis-(24-N-Boc-24-Amino-16-aza-19,22-dioxa-15-oxotetracosyl Malonate (24): According to the procedure for the synthesis of 6 an excess of 18.0 g (122 mmol) bis-(2-aminoethyl)ethylenglycol was mono-Boc-protected with 4.37 g Boc-anhydride in dioxane. Analogously to the preparation of 7, the resulting Boc-derivative is condensed with an equimolar amount of hydroxyacid 5 in the presence of CDI in DMF/CH$_2$Cl$_2$. 2.00 g (4.09 mmol) of the freshly prepared amidoalcohol and 192.2 mg (1.85 mmol) malonic acid in the presence of 70 mg (0.537 mmol) DMAP and 0.84 g (4.09 mmol) DCC were reacted as it is described for the synthesis of 8. After FC chromatographic purification (SiO$_2$, EtOAc:EtOH=95:5), the malonate 24 was isolated in 48% yield.—$^1$H NMR (400 MHz, RT, CDCl$_3$): δ=6.00 (br, 2H), 4.99 (br, 2H), 4.09 (t, $^3$J=6.7 Hz, 4H), 3.55 (m, 8H), 3.51 (m, 8H), 3.42 (dt, 4H), 3.33 (s, 2H), 3.29 (dt, 4H), 2.14 (t, $^3$J=7.4 Hz, 4H), 1.60 (m, 8H), 1.41 (s, 18H), 1.22 (m, 40H).—$^{13}$C NMR (100.5 MHz, RT, CDCl$_3$): δ=173.26 (2C), 166.68 (2C), 155.95 (2C), 79.34 (2C), 70.17, 69.99 (8C), 65.65 (2C), 41.66 (1C), 40.29, 39.09 (4C), 36.72 (2C), 29.60, 29.54, 29.48, 29.37, 29.30, 29.18, 29.05, 28.43 (20C), 28.37 (6C), 25.75 (4C):—MS (FAB): m/z=1069 [M+Na]$^+$, 1046 [M]$^+$, 945 [M-Boc]$^+$, 845 [M-2 Boc]$^+$.

N-Boc-Protected [3:3]-Hexakisadduct (22) and Sixfold Protonated Hexaaminoamphifullerene (23): e,e,e-Trisadduct 18 (75.0 mg, 55.2 µmol) was dissolved in 25 mL dry CH$_2$Cl$_2$ and treated with an excess of DMA (68.35 mg, 0.331 mmol). After stirring for 2 h at RT, 310 mg malonate 24 (346.7 mg, 0.331 mmol) and 111.25 mg (0.331 mmol) CBr$_4$ were added subsequently and the reaction mixture was stirred for some minutes to allow complete dissolution. 100.5 mg (0.663 mmol, 99 µL) of DBU, diluted in 15 mL dry CH$_2$Cl$_2$, was added dropwise over 1 h. The solution was stirred at RT and under N$_2$ protection for one more day. Purification by FC on silica (CH$_2$Cl$_2$:EtOH=95:5 to 9:1; R$_f$(22)=0.2 at 95:5) gave a yellow solid 22 (95.0 mg, 55% yield). The cleavage of the Boc protection groups was performed in CH$_2$Cl$_2$ (5 mL) with TFA (3 mL) to result in a yellow clear solid 23 in almost quantitative yield.

22: $^1$H NMR (400 MHz, RT, CDCl$_3$): δ=6.98 (br, 6H), 5.00 (br, 6H), 4.65 (m, 6H), 4.22 (m, 12H), 4.14 (m, 3H), 3.98 (m, 3H), 3.63-3.50 (m, 48H), 3.43 (dt, 12H), 3.29 (m, 12H), 2.15 (t, $^3$J=7.6 Hz, 12H), 2.00-1.51 (m, 39H), 1.41 (s, 54H), 1.35-1.21 (m, 120H), 1.14 (m, 18H), 0.82 (m, 3H).—$^{13}$C NMR (100.5 MHz, RT, CDCl$_3$): δ=173.27 (6C), 163.83, 163.69, 163.64, 163.15 (12C), 155.96 (6C), 146.39, 145.89, 145.66, 145.60, 145.31, 144.89, 144.84, 141.97, 141.85, 141.78. 140.96, 140.81, 140.69, 140.65 (48C, C$_{60}$ sp$^2$), 79.32 (6C), 70.22, 70.00, 69.25, 69.21, 69.11 (24C+4C C$_{60}$ sp$^3$), 67.03, 66.92, 66.23 (12C), 46.66, 45.63 (6C), 40.30, 39.10 (12C), 36.70 (6C), 29.96, 29.70, 29.66, 29.57, 29.50, 29.42, 29.36, 29.26, 29.17, 28.77 (78C), 28.38 (18C), 26.33, 25.81, 25.75, 25.60 (12C).—MS (FAB): m/z=4510 [M+Na]$^+$, 4487 [M]$^+$, 4388 [M-Boc]$^+$, 3885 [M-6 Boc]$^+$.—UV/Vis (CH$_2$Cl$_2$): λ$_{max}$=243, 271, 281, 316, 334.—IR (KBr): ν=3423, 2926, 2854, 1747, 1716, 1652, 1541, 1457, 1385, 1366, 1263, 1218, 1171, 1101, 804, 757, 715, 540, 528, 457 cm$^{-1}$.

23: $^1$H NMR (400 MHz, RT, CDCl$_3$): δ=8.00 (m, 6H), 4.64 (m, 6H), 4.28 (m, 12H), 4.10 (m, 3H), 4.03 (m, 3H), 3.72-3.51 (3m, 48H), 3.30 (dt, 12H), 3.11 (m, 12H), 2.18 (t, $^3$J=7.5 Hz), 1.88-1.45 (m, 39H), 1.40-1.23 (m, 120H), 1.20 (m, 18H), 0.89 (m, 3H).—$^{13}$C NMR (100.5 MHz, RT, CDCl$_3$): δ=176.51, 176.41 (6C), 164.84, 164.82, 164.52, 163.95 (12C), 147.17, 147.09, 146.76, 146.59, 146.30, 145.80, 143.51, 143.40, 143.06, 142.98, 142.56, 142.46, 142.19 (48C, C$_{60}$ sp$^2$), 71.32, 71.25, 70.84, 70.78, 70.65, 69.54 (24C+4C C$_{60}$ sp$^3$), 68.28, 67.87, 67.33, 66.44 (12C), 47.71 (6C), 40.62, 40.24, 40.12 (12C), 37.12, 37.07 (6C), 30.89, 30.84, 30.76, 30.71, 30.67, 30.58, 30.56, 30.41, 30.26, 30.10, 30.03, 29.71, 29.65, 29.54, 29.15 (78C), 27.14, 27.04, 26.99, 26.91 (12C).—MS (FAB): m/z=1944 [M]$^{2+}$, 3887 [M]$^+$, 3910 [M+Na]$^+$.—UV/Vis (H$_2$O, pH 7.2): λ$_{max}$=246.5, 272, 284, 321, 339.5.—IR (KBr): ν=3423, 2925, 2854, 1747, 1682, 1648, 1543, 1465, 1431, 1384, 1354, 1264, 1206, 1133, 836, 801, 722, 528 cm$^{-1}$.

Bis(N-Boc-6-Aminohexyl) Malonate (33): 104 mg (1.00 mmol) malonic acid was reacted with 477.5 mg (2.20 mmol, 1.1 eq) N-Boc-protected 6-aminohexan-1-ol in the presence of DMAP and DCC according to the preparation of malonate 8. 167 mg of 33 were isolated (72% yield) as a colorless oil.—$^1$H NMR (400 MHz, RT, CDCl$_3$): δ=4.59 (br, 2H), 4.09 (t, $^3$J=6.8 Hz, 4H), 3.32 (s, 2H), 3.06 (m, 4H), 1.59 (q, $^3$J=7.0 Hz), 1.50-1.39 (m, 4H), 1.39 (s, 18H), 1.25-1.34 (m, 8H).—$^{13}$C NMR (100.5 MHz, RT, CDCl$_3$): δ=166.62 (2C), 155.95 (2C), 78.98 (2C), 65.40 (2C), 41.56 (1C), 40.38 (2C), 33.81 (2C), 29.89 (2C), 28.36 (6C), 26.30, 25.43 (4C).—MS (FAB): m/z=503 [M$^+$], 403 [M$^+$-Boc], 347 [M$^+$-Boc-tBu], 303 [M$^+$-2 Boc].

Bis(N-Boc-6-Aminohexyl) Malonamide (34), Bis(N-Boc-8-Amino-3,6-dioxaoctyl) Malonamide (35) and Bis(N-Boc-13-Amino-4,7,10-trioxatridecyl) Malonamide (36): Similar to the synthesis of 8, by condensation of 1.0 eq (104 mg, 1 mmol) malonic acid with 1.1 eq. (2.20 mmol) of N-Boc-hexamethylene diamine, N-Boc-8-amino-3,6-dioxaocty-lamine and N-Boc-4,7,10-trioxatridecylamine, respectively, in the presence of DMAP and DCC. Yields 34: 61%, 35: 67%, 36: 58%.

34: $^1$H NMR (300 MHz, RT, CDCl$_3$): δ=6.97 (br, 2H), 4.54 (br, 2H), 3.22 (q, $^3$J=6.9 Hz, 4H), 3.13 (s, 2H), 3.01 (q, $^3$J=6.8 Hz, 4H), 1.54-1.42 (m, 8H), 1.42 (s, 18H), 1.36-1.27 (m, 8H).—$^{13}$C NMR (75 MHz, RT, CDCl$_3$): δ=169.34 (2C), 158.12 (2C), 81.15 (2C), 45.07, 42.26 (4C), 41.36 (1C), 32.01, 31.21 (4C), 30.48 (6C), 28.30, 28.16 (4C).—MS (FAB): m/z=501 [M$^+$], 401 [M$^+$-Boc], 345 [M$^+$-Boc-tBu], 301 [M$^+$-2 Boc].

35: $^1$H NMR (400 MHz, RT, CDCl$_3$): δ=7.34 (br, 2H), 5.26 (br, 2H), 3.57 (m, 8H), 3.52 (t, $^3$J=5.1 Hz, 8H), 3.43 (m, 4H), 3.27 (m, 4H), 1.40 (s, 18H).—$^{13}$C NMR (100.5 MHz, RT, CDCl$_3$): δ=167.19 (2C), 155.93 (2C), 79.24 (2C), 70.29, 70.18 (8C), 42.76 (1C), 40.49 (2C), 39.41 (2C), 28.48 (6C).—MS (FAB): m/z=565 [M$^+$], 465 [M$^+$-Boc], 365 [M$^+$-2 Boc].

36: $^1$H NMR (300 MHz, RT, CDCl$_3$): δ=7.39 (br, 2H), 5.02 (br, 2H), 3.65-3.47 (m, 12H), 3.33 (q, $^3$J=6.1 Hz, 4H), 3.18 (q, $^3$J=6.1 Hz, 4H), 3.09 (s, 2H), 1.82-1.66 (m, 8H), 1.40 (s, 18H).—$^{13}$C NMR (75 MHz, RT, CDCl$_3$): δ=167.73 (2C), 156.47 (2C), 79.27 (2C), 70.94, 70.91, 70.58, 70.11, 69.91 (12C), 43.17 (1C), 38.87 (2C), 38.13 (2C), 30.02 (2C), 29.22 (2C), 28.85 (6C).—MS (FAB): m/z=709 [M$^+$], 610 [M$^+$-Boc], 510 [M$^+$-2 Boc].

N-Boc-Protected Bis(6-Aminohexyl) Malonate [3:3]-Hexakisadduct (25): Under the same reaction conditions as given for the preparation of hexakisadduct 19 by reacting 100 mg (73.6 μmol, 1.0 eq) e,e,e-trisadduct 18 with an excess of 91.1 mg (0.442 mmol, 6.0 eq) DMA and 221.8 mg (0.442 mmol, 6.0 eq) N-protected aminohexyl malonate 33 in the presence of 146.6 mg (0.442 mmol, 6.0 eq) CBr$_4$, dissolved in 40 ml CH$_2$Cl$_2$, and 134.6 mg (132.2 μl, 0.884 mmol, 12.0 eq) DBU in 15 mL CH$_2$Cl$_2$ and stirring for 2 d. After liquid chromatographic purification (CH$_2$Cl$_2$:EtOAc=93:7) 106 mg (50% yield) of 25 were isolated.—$^1$H NMR (400 MHz, RT, CDCl$_3$): δ=4.74 (br, 6H), 4.63 (m, 6H), 4.25 (m, 12H), 4.12 (m, 3H), 3.98 (m 3H), 3.05 (m, 12H), 1.69-1.40 (3m, 39H), 1.40 (s, 54H), 1.31 (m, 24H), 1.16 (m, 18H), 0.85 (m, 3H).—$^{13}$C NMR (100.5 MHz, RT, CDCl$_3$): δ=163.81, 163.73, 163.55, 163.13 (12C), 155.98 (6C), 146.23, 145.74, 145.68, 145.21, 144.89, 144.85, 142.03, 141.82, 141.75, 141.64, 140.85, 140.72 (48C, C$_{60}$ sp$^2$), 78.87 (6C), 69.22, 69.18, 69.11 (12C), 67.00, 66.86, 66.79, 66.27 (12C), 46.66, 45.66 (6C), 40.46 (6C), 29.89, 29.17, 28.78, 28.73, 28.30, 26.40, 26.34, 25.59, 25.54 (42C), 28.40 (6C).—MS (FAB): m/z=2859 [M]$^+$, 2802 [M t-bu]$^+$, 2759 [M-boc]$^+$, 2704 [M-Boc-tBu]$^+$, 2560, [M-3 Boc]$^+$, 2459 [M-4 Boc]$^+$, 2359 [M-5 Boc]$^+$, 2259 [M-6 Boc]$^+$.—UV/Vis (H$_2$O pH 7.2): λ$_{max}$=245, 273 (sh), 282 (sh), 320, 336.—IR (KBr): ν=3422, 2930, 2857, 1746, 1716, 1634, 1517, 1458, 1385, 1366, 1385, 1366, 1263, 1218, 1170, 1080, 759, 714, 540, 528 cm$^{-1}$.

Hexaammonium Trifluoroacetate Amphifullerene (29): The cleavage of the Boc protection groups of 100 mg 25 in CH$_2$Cl$_2$ (5 mL) with TF A (3 mL) resulted in the hexaammonium trifluoroacetate salt 29 as a yellow clear solid in quantitative yield.—$^1$H NMR (300 MHz, RT, CD$_3$OH): δ=7.85 (br, 18H), 4.69 (m, 6H), 4.35 (m, 12H), 4.14 (m, 3H), 4.02 (m, 3H), 2.92 (t, $^3$J=6.7 Hz, 12H), 1.95-1.51 (3m, 39H), 1.35 (m, 24H), 1.34-1.11 (m, 18H), 0.83 (m, 3H).—$^{13}$C NMR (75 MHz, RT, CD$_3$OH): δ=165.29, 165.23, 164.69, 164.47 (12C), 147.71, 147.50, 147.25, 146.82, 146.76, 146.50, 146.29, 144.09, 143.91, 143.33, 143.22, 142.99, 142.84, 142.66 (48C, C$_{60}$ sp$^2$), 71.29, 71.26, 71.21, 70.99 (12C, C$_{60}$ sp$^3$), 68.87, 68.61, 67.81 (12C), 48.25 (6C), 41.05 (6C), 31.20, 30.85, 30.57, 30.41, 29.85, 29.82, 28.90, 28.87, 28.01, 27.43, 27.38, 27.34, 27.00, 26.95 (42C).—MS (FAB): m/z=720 [C$_{60}$]$^+$, 1131 [M]$^{2+}$, 2259 [M]$^+$, 2281 [M+Na]$^+$.—UV/Vis (H$_2$O pH 7.2): λ$_{max}$=214.5, 245.5, 271, 282.5, 319, 337.—IR (KBr): ν=3443, 30.95, 2935, 2859, 1745, 1681, 1539, 1463, 1433, 1385, 1355, 1264, 1206, 1136, 1082, 993, 838, 801, 759, 723, 669, 540, 527 cm$^{-1}$.

N-Boc-Protected Bis(6-aminohexyl) Malonamide [3:3]-Hexakisadduct (26): By the same procedure as for 25, from 100 mg (73.6 μmol, 1.0 eq) e,e,e-trisadduct 18, 91.1 mg (0.442 mmol, 6.0 eq) DMA, 221.3 mg (0.442 mmol, 6 eq) bis(N-Boc-6-aminohexyl) malonamide 34, 146.6 mg (0.442 mmol, 6.0 eq) CBr$_4$ and 134.6 mg (132.2 μL, 0.884 mmol, 12 eq) DBU in CH$_2$Cl$_2$ after chromatographic purification (toluene:EtOAc=70:30) 135 mg (28% yield) of 26 was obtained.—$^1$H NMR (400 MHz, RT, CDCl$_3$): δ=6.92 (br, 3H), 6.60 (br, 3H), 4.92 (br, 3H), 4.75 (br, 3H), 4.61 (m, 6H), 4.13 (m, 3H), 3.99 (m, 3H), 3.45-3.10 (m, 12H), 3.05-3.20 (m, 12H), 3.01 (m, 12H), 1.70-1.40 (4m (3H+6H+24H+6H), 1.39 (s, 54H), 1.26 (m, 24H), 1.15 (m, 18H), 0.84 (m, 3H).— $^{13}$C NMR (100.5 MHz, RT, CDCl$_3$): δ=163.54, 163.07 (12C), 156.08, 155.99 (6C), 145.51, 145.17, 144.70, 144.48, 144.14, 142.27, 142.06, 141.76, 140.96, 140.82 (48C, C$_{60}$ sp$^2$), 78.84 (6C), 71.14, 70.97, 69.48 (12C), 66.99, 66.38 (6C), 52.25 (3C), 46.86 (3C), 40.49, 40.28 (12C), 29.86, 29.63, 29.31, 29.18, 28.81, 26.57, 26.44, 26.35, 25.58 (42C), 28.44, 28.42 (6C).—MS (FAB): m/z=2852 [M]$^+$, 2753 [M-Boc]$^+$, 2697 [M-Boc-tBu]$^+$, 2653 [M-2 Boc]$^+$, 2553 [M-3 Boc]$^+$, 2453 [M-4 Boc]$^+$, 2353 [M-5 Boc]$^+$, 2252 [M-6 Boc]$^+$, 720 [C$_{60}$]$^+$.—UV/Vis (CH$_2$Cl$_2$): λ$_{max}$=244, 273.5 (sh), 282.5 (sh), 320, 337.IR (KBr): ν=3418, 2931, 2857, 1747, 1632, 1523, 1548, 1392, 1366, 1261, 1223, 1172, 1138, 1106, 1075, 865, 802, 752, 710, 539, 524.

Hexaammonium Trifluoroacetate Amphiphile (30): From 100 mg of Boc-26 by deprotection with excess of TFA in CH$_2$Cl$_2$ 75.1 mg (95% yield) of the stable hexaammonium trifluoroacetate 30 was obtained.—$^1$H NMR (400 MHz, RT, CD$_3$OD): δ=8.83 (m, 3H) 8.72 (m, 3H), 7.82 (br, 18H), 4.80 (m, 3H), 4.64 (m, 3H), 4.15 (m, 3H), 4.01 (m, 3H), 3.38-3.20 (m, 12H), 2.89 (m, 12H), 1.83-1.45 (3m, 39H) 1.36 (m, 24H), 1.20 (m, 18H), 0.89 (m, 3H).—$^{13}$C NMR (100.5 MHz, RT, CD$_3$OD): δ=165.06, 164.83, 164.60, 164.21 (12C), 146.84, 146.75, 146.25, 145.97, 145.85, 145.50, 144.70, 144.51, 144.25, 143.94, 143.71, 143.58, 143.28, 142, 13, 142.05 (48C, C$_{60}$ sp$^2$), 73.52, 72.88, 71.12, 71.10 (12C), 68.35, 67.44 (6C), 54.87 (3C), 48.65 (3C), 41.00, 40.94, 40.75, 40.70 (12C), 30.66, 30.56, 30.33, 30.30, 29.87, 28.63, 28.53, 27.67, 27.57, 27.37, 27.02, 26.95 (42C).—MS (FAB): m/z=2253 [M]$^+$, 1440 [C$_{60}$-Dimer]$^+$, 720 [C$_{60}$]$^+$.—UV/Vis (H$_2$O)/pH 7.2): λ$_{max}$=215, 242.5 (sh), 272 (sh), 281 (sh), 317.5, 336.—IR(KBr): ν=3424, 2935, 2859, 1744, 1678, 1541, 1460, 1385, 1275, 1204, 1179, 1135, 836, 800, 722, 539, 522 cm$^{-1}$.

N-Boc-Protected Di(N-Boc-8-amino-3,6-dioxaoctyl) Malonamide [3:3]-Hexakisadduct (27): From 100 mg (73.6 µmol, 1.0 eq) e,e,e-trisadduct 18, 91.1 mg (0.442 mmol, 6.0 eq) DMA, 249.5 mg (0.442 mmol, 6 eq) bis(N-Boc-8-amino-3,6-dioxaoctyl) malonamide 35, 146.6 mg (0.442 mmol, 6.0 eq) $CBr_4$ and 134.6 mg (132.2 µL, 0.884 mmol, 12 eq) DBU in $CH_2Cl_2$ after chromatographic purification [LC: ($CH_2Cl_2$:EtOH=95:5), HPLC (toluene:MeOH=93:7)] 100 mg (45% yield) of 27 was obtained.—$^1$H NMR (400 MHz, RT, $CDCl_3$): δ=7.40 (br, 6H), 5.29 (br, 3H), 5.17 (br, 3H), 4.59 (m, 6H), 4.13 (m, 3H), 3.98 (m, 3H), 3.51 (m, 60H), 3.27 (m, 12H), 1.75-1.45 (3m, 15H), 1.40 (s, 54H), 1.20 (m, 18H), 0.90 (m, 3H).—$^{13}$C NMR (100.5 MHz, RT, $CDCl_3$): δ=163.74, 163.13, 163.03, 162.97 (12C), 156.07, 156.03 (6C), 145.50, 145.34, 145.11, 144.83, 144.56, 144.35, 144.21, 141.88, 141.76, 141.00, 140.88 (48C, $C_{60}$ $sp^2$), 79.08 (6C), 71.16, 70.72 (6C), 70.33, 70.16, 70.13, 69.47, 69.44 (30C), 66.96, 66.48 (6C), 51.89 (3C), 46.79 (3C), 40.29 (12C), 29.27, 29.06, 28.80, 28.59, 26.44, 25.61 (12C), 28.44 (6C).—MS (FAB): m/z=3068 [$M^+$+Na], 2946 [$M^+$-Boc], 2889 [M-Boc-tBu]$^+$, 2845 [$M^+$-2 Boc], 2745 [$M^+$-3 Boc], 2645 [$M^+$-4 Boc], 2545 [$M^+$-5 Boc], 2445 [$M^+$-6 Boc].—UV/Vis ($CH_2Cl_2$): $\lambda_{max}$=243.5, 273 (sh), 284 (sh), 320.5, 336.5.—IR (KBr): N=3420, 2926, 2857, 1746, 1694, 1521, 1456, 1385, 1367, 1258, 1172, 1105, 710, 524 $cm^{-1}$.

Hexaammonium Trifluoroacetate Amphiphile (31): From 100 mg of Boc-27 by deprotection with an excess of TFA in $CH_2Cl_2$ 76.25 mg (95% yield) of the hexaammonium trifluoroacetate 31 was obtained.—$^1$H NMR (400 MHz, RT, $CD_3OD$): δ=4.78, 4.60 (2m, 6H), 4.14 (m, 3H), 3.99 (m, 3H), 3.86 (m), 3.73-3.40 (2m, 60H), 3.15 (m, 12H), 1.80-1.20 (4m, 33H), 0.90 (m, 3H).—$^{13}$C NMR (100.5 MHz, RT, $CD_3OD$): δ=165.03, 164.82, 164.56, 164.01 (12C), 146.81, 146.40, 145.92, 145.78, 145.61, 145.55, 145.02, 144.17, 143.97, 143.85, 143.61, 143.49, 143.28, 142.09, 142.02 (48C, $C_{60}$-$sp^2$), 73.15, 72.69 (6C), 71.50, 71.45, 71.37, 71.00, 70.66, 70.31 (30C), 68.25, 67.90 (6C), 54.37 (3C), 44.58 (3C), 41.18, 40.65 (12C), 30.65, 30.54, 30.24, 29.81, 27.67, 26.93 (12C).—MS (FAB): m/z=2467 [M+Na]$^+$, 2445 [M]$^+$, 1440, 720 [$C_{60}$]$^+$.—UV/Vis ($H_2O$ pH 7.2): $\lambda_{max}$=214, 244 (sh), 272 (sh), 283 (sh), 319, 335.5.—IR (KBr): N=3442, 2927, 2857, 1742, 1682, 1541, 1458, 1432, 1385, 1275, 1206, 1180, 1132, 837, 802, 723, 539, 522 $cm^{-1}$.

N-Boc-Protected Bis(N-Boc-13-Amino-4,7,10-trioxatridecyl) Malonamide [3:3]-Hexakisadduct (28): From 100 mg (73.6 µmol, 1.0 eq) e,e,e-trisadduct 18, 91.1 mg (0.442 mmol, 6.0 eq) DMA, 313.4 mg (0.442 mmol, 6 eq) bis(N-Boc-13-amino-4,7,10-trioxatrideeyl) malonamide 36, 146.6 mg (0.442 mmol, 6.0 eq) $CBr_4$ and 134.6 mg (132.2 µL, 0.884 mmol, 12 eq) DBU and 3 d stirring, after chromatographic purification [LC: (EtOAc:EtOH=92:8), HPLC: (toluene:MeOH=91:9)] 121.9 mg (49% yield) of 28 was obtained.—$^1$H NMR (400 MHz, RT, $CDCl_3$): δ=7.50-6.90 (2br, 6H), 5.00 (m, 6H), 4.59 (m, 6H), 4.10 (m, 3H), 3.97 (m, 3H), 3.70-3.35 (m, 84H), 3.17 (m, 12H), 1.80-1.40 (m, 39H), 1.40 (s, 54H), 1.17 (m, 18H), 0.85 (m, 3H).—$^{13}$C NMR (100.5 MHz, RT, $CDCl_3$): δ=164.45, 163.66, 163.03, 162.92 (12C), 156.02 (6C), 145.49, 145.31, 145.07, 144.80, 144.66, 144.58, 144.38, 144.14, 142.26, 141.73, 141.00, 140.81 (48C, $C_{60}$ $sp^2$), 78.81 (12C), 71.37, 71.15 (6C), 70.86, 70.47, 70.35, 70.25, 70.17, 69.76, 69.49, 69.01, 68.75 (42C), 66.81, 66.27 (6C), 52.33 (3C), 46.78 (3C), 39.21, 38.49, 38.23, 38.02 (12C), 29.61, 29.21, 20.00, 28.79, 28.73, 26.42, 25.54 (30C), 28.44 (6C).—MS (FAB): m/z=3381 [M]$^+$, 3323 [M-tBu]$^+$, 3277 [M-Boc]$^+$, 3177 [M-2 Boc]$^+$, 3077 [M-3 Boc]$^+$, 2977 [M-4 Boc]$^+$, 2877 [M-5 Boc]$^+$.—UV/Vis ($CH_2Cl_2$): $\lambda_{max}$=244, 270.5, 281, 318, 336.

Hexaammonium Trifluoroacetate Amphiphile (32): From 100 mg of N-Boc-28 by deprotection with excess of TFA in $CH_2Cl_2$, 85.0 mg (94% yield) of the trifluoroacetate 32 was obtained.—$^1$H-NMR (400 MHz, RT, $CDCl_3$): δ=9.18 (m, 3H), 9.07 (m, 3H), 7.79 (m, 18H), 4.55 (m, 6H), 4.15 (m, 3H), 3.97 (m, 3H), 3.70-3.25 (m, 72H+12H), 3.03 (m, 12H), 1.97-1.47 (3m, 3H+12H+6H+12H+6H), 1.20 (m, 18H), 0.88 (m, 3H).—$^{13}$C-NMR (100.5 MHz, RT, $CDCl_3$): δ=163.96, 163.90, 163.84, 163.06 (12C), 145.47, 145.28, 144.91, 144.69, 144.47, 144.26, 144.03, 143.41, 142.90, 142.60, 142.50, 142.43, 142.16, 141.64, 140.94, 140.88 (48C, $C_{60}$ $sp^2$), 71.69, 71.55 (6C), 70.31, 70.24, 70.02, 69.90, 69.80, 69.66, 69.55, 69.46, 69.41, 68.35, 68.13, 67.96 (42C), 67.00, 66.56 (8C), 53.21 (3C), 46.92 (3C), 39.90, 39.74 (6C), 37.21, 37.15 (6C), 29.67, 29.28, 29.24, 28.91, 28.79, 28.43, 26.31, 26.10, 25.69 (30C).—MS-(FAB): m/z=2878 [M$^+$], 2371, 1440, 720 [$C_{60}^+$].—UV/Vis ($H_2O$ pH 7.2): $\lambda_{max}$=214.5, 245.5, 271, 282.5, 319, 337.—IR (KBr): ν=3442, 2926, 1741, 1682, 1558, 1541, 1523, 1458, 1434, 1385, 1275, 1206, 1179, 1131, 837, 802, 723, 538, 522 $cm^{-1}$.

L-Alanine tert-Butyl Ester [3+3]-Hexakisadduct (42) and L-Alanine [3+3]-Hexakisadduct (40): 351.9 mg (0.161 mmol, 1 eq) hexaacid 37, 361.3 mg (1.99 mmol, 12 eq) L-alanine tert-butyl ester 41 hydrochloride, 270 µL $Et_3N$ and 223.2 mg (12 eq) N-hydroxysuccinimide [NHS] were dissolved in a mixture of 50 mL dry THF and 20 mL of dry DMF and the resulting solution was cooled to 0° C. 371.8 mg (12 eq) DCC in 15 mL of dry THF were slowly added and the mixture stirred for 3 d at RT. The dicyclohexyl urea formed was filtered off and the filtrate concentrated in vacuo. The remaining residue was dissolved in 100 mL EtOAc and washed with 10% aqueous citric acid, 0.5N aqueous $KHCO_3$ solution and brine. The organic layer was dried over anhydrous $MgSO_4$ and the EtOAc was removed in vacuo. Flash chromatography ($SiO_2$, $CH_2Cl_2$:MeOH=97:3) afforded 307.5 mg (73% yield) 42 as a dark yellow solid. The cleavage of the tert-butyl groups of the [3+3]-hexakisadduct 42 (100 mg, 0.034 mmol) was achieved with 1.5 mL TFA in 20 mL $CH_2Cl_2$. The mixture was stirred for 8 h at RT, the solvent and TFA were removed in vacuo and the yellow solid alanino amphifullerene 40 (88.5 mg, 0.034 mmol) was obtained in quantitative yield.

42: $^1$H NMR (400 MHz, RT, $CDCl_3$): δ=6.68 (m, 6H), 4.64 (m, 6H), 4.44 (m, 6H), 4.33 (m, 12H), 4.10 (m, 3H), 3.96 (m, 3H), 2.33 (m, 12H), 2.03 (m, 12H), 1.73 (m, 3H), 1.57 (m, 6H), 1.50 (m, 12H), 1.42 (s, 54H), 1.33 (d, $^2$J=7.08 Hz, 18H), 1.13 (m, 18H), 0.78 (m, 3H).—$^{13}$C NMR (100.5 MHz, RT, $CDCl_3$): δ=172.10 (6C), 171.05 (6C), 163.48, 163.26, 162.86 (12C), 146.07, 146.0, 145.74, 145.67, 145.57, 145.52, 145.47, 144.94, 144.70, 141.96, 141.75, 141.37, 141.28, 141.22, 140.82, 140.70, 140.56, 140.51 (48C, $C_{60}$ $sp^2$), 81.64 (6C), 69.20, 69.16 (12C), 67.05, 66.32 (12C), 48.65 (6C), 46.86, 46.81, 45.51 (6C), 32.16 (6C), 29.36, 29.27, 28.89 (12C), 28.04 (18C), 26.46, 25.68 (6C), 24.32, 24.22, 24.15 (6C), 18.42 (6C).IR (KBr): ν=3406, 2976, 2933, 2857, 1743, 1677, 1655, 1526, 1458, 1384, 1369, 1263, 1218, 1153, 1079, 1017, 994, 847, 759, 714, 540, 528 $cm^{-1}$.—MS (FAB): m/z=2942 [M]$^+$, 2886 [M-tBu]$^+$, 2607 [M-6 tBu]$^+$, 720 [$C_{60}$]$^+$.—UV/Vis ($CH_2Cl_2$): $\lambda_{max}$=242, 271, 282, 317, 335.

40: $^1$H NMR (300 MHz, RT, THF-d$_8$): δ=8.41 (s br, 6H), 7.53 (m, 6H), 4.69 (m, 6H), 4.66 (m, 6H), 4.45 (t, $^3$J=6.05 Hz, 6H), 4.30 (m, 12H), 4.05 (m, 3H), 3.93 (m, 3H), 2.29 (t, $^3$J=6.10 Hz, 12H), 1.99 (m, 12H), 1.76 (m, 3H), 1.54 (m, 6H), 1.51 (m, 6H), 1.32 (d, $^2$J=7.15 Hz, 18H), 1.19 (m, 18H), 0.80 (m, 3H).—$^{13}$C NMR (75 MHz, RT, THF-d$_8$): δ=174.58 (6C), 172.26, 171.98 (6C), 164.08, 164.00, 163.76, 163.76, 163.31 (12C), 147.24, 146.85, 146.71, 146.57, 146.28, 145.88, 145.80, 145.70, 145.68, 143.08, 142.99, 142.65, 142.59, 141.97, 141.86, 141.64 (48C, C$_{60}$ sp$^2$), 70.36, 70.27 (12C), 68.21, 66.36 (12C), 48.51, 48.45 (6C), 47.94, 46.77 (6C), 32.41 (6C), 30.44, 30.21, 29.75 (12C), 27.48, 26.51 (6C), 18.23, 18.18 (6C).—IR (KBr): ν=3382, 3074, 2934, 2857, 2556, 1745, 1635, 1541, 1458, 1384, 1354, 1263, 1217, 1167, 1079, 1042, 1020, 898, 806, 754, 713, 667, 538, 527 cm$^{-1}$.—MS (FAB): m/z=2607 [M+H]$^+$, 2562 [M−CO$_2$]$^+$, 2477, 720 [C$_{60}$]$^+$.—UV/Vis (H$_2$O): λ$_{max}$=212.5, 244, 271.5, 280, 316, 337.

N-(L-Alanyl)-L-alanine Tert-butyl Ester [3+3]-hexakisadduct (45) and N-(L-Alanyl)-L-alanine [3+3]-Hexakisadduct (47): The coupling of N-(L-alanyl)-L-alanine tert-butyl ester (346.2 mg, 12 eq) with the hexaacid 37 (273.9 mg, 1 eq) was carried out according to the procedure for the synthesis of 42 by activation with DCC (12 eq) and NHS (12 eq). Purification by flash chromatography (SiO$_2$, CH$_2$Cl$_2$/MeOH 96:4) gave 326.7 mg (77%) [3+3]-hexakisadduct 45 as a dark yellow solid. The cleavage of the tert-butyl groups of the [3+3]-hexakisadduct 45 (175.1 mg, 0.052 mmol) was achieved in CH$_2$Cl$_2$ (20 mL) with TFA (1.5 mL). The mixture was stirred overnight at RT, the solvent and TFA were removed in vacuo and 157.6 mg (0.052 mmol) of the peptido amphifullerene hexakisadduct 47 was obtained as a yellow solid in quantitative yield.

45: $^1$H NMR (400 MHz, RT, CDCl$_3$): δ=7.52 (d br, 3H), 7.33 (d br, 3H), 4.67 (m, 12H), 4.36 (m, 12H), 4.13 (m, 3H), 3.98 (m, 3H), 2.66, 2.35 (m, 12H), 2.04 (m, 12H), 1.77 (m, 3H), 1.52 (m, 12H), 1.45 (s, 54H), 1.39 (d, $^2$J=7.15 Hz, 18H), 1.36 (d, $^2$J=7.05 Hz, 18H), 1.15 (m, 18H), 0.81 (m, 3H).—$^{13}$C NMR (100.5 MHz, RT, CDCl$_3$): δ=172.38, 172.27 (12C), 171.95, 171.66 (6C), 163.75, 163.51, 163.48, 163.12 (12C), 146.32, 145.78, 145.72, 145.19, 145.10, 144.92, 142.13, 141.90, 141.58, 141.39, 140.95, 140.86, 140.74, 140.57 (48C, C$_{60}$ sp$^2$), 81.73 (6C), 69.24, 69.15 (12C), 67.05, 66.31 (12C), 48.80, 48.54 (12C), 46.77, 45.31 (6C), 31.76 (6C), 29.18, 28.81 (12C), 27.94 (18C), 26.35, 25.60 (6C), 24.13, 23.96, 23.87 (6C), 18.29, 18.15, 18.09, 18.04 (12C).—IR (KBr): N=3388, 3315, 3071, 2977, 2934, 2858, 1744, 1655, 1527, 1456, 1383, 1369, 1263, 1218, 1157, 1079, 1017, 993, 847, 759, 714, 540, 528 cm$^{-1}$.—MS (FAB): m/z=3370 [M]$^+$, 3314 [M−tBu]$^+$, 3113, 720 [C$_{60}$]$^+$.—UV/Vis (CH$_2$Cl$_2$): λ$_{max}$=246, 271.5, 281.5, 317.5, 336.5.

47: $^1$H NMR (300 MHz, RT, DMSO-d$_6$): δ=8.12 (d, $^2$J=7.69 Hz, 6H), 8.03 (d, $^2$J=7.68 Hz, 6H), 4.75 (m, 6H), 4.64 (m, 6H), 4.30 (m, 12H), 4.18 (m, 6H), 3.99 (m, 6H), 2.19 (m, 12H), 1.82 (m, 6H), 1.52 (m, 9H), 1.25 (d, $^2$J=7.04 Hz, 18H), 1.17 (d, $^2$J=7.06 Hz, 18H), 1.06 (m, 18H), 0.50 (m, 3H).—$^{13}$C NMR (75 MHz, RT, DMSO-d$_6$): δ=173.95 (6C), 172.10 (6C), 170.79, 170.66 (6C), 162.63, 162.13, 161.79 (12C), 145.74, 145.67, 144.88, 144.43, 144.01, 143.96, 143.80, 141.66, 141.52, 141.46, 141.27, 140.47, 140.32, 140.13 (48C, C$_{60}$ sp$^2$), 69.04, 68.85 (12C), 66.72, 66.65, 65.76 (12C), 47.64, 47.29 (12C), 46.88, 45.57 (6C), 30.97 (6C), 29.23, 28.59, 28.12 (12C), 26.08 (12C), 24.84, 24.03 (6C), 18.10, 16.99 (12C).—IR (KBr): ν=3306, 3064, 3030, 2934, 2858, 2548, 1744, 1649, 1532, 1455, 1384, 1352, 1264, 1217, 1170, 1079, 1019, 992, 901, 810, 755, 738, 713, 701, 669, 539, 527 cm$^{-1}$.—MS (FAB): m/z=3512 [M+Na]$^+$, 3489 [M+H]$^+$, 3213, 720 [C$_{60}$]$^+$.—UV/Vis (H$_2$O): λ$_{max}$=212, 243.5, 272, 281, 318, 336.

N-(L-Alanyl)-L-phenylalanine tert-Butyl Ester [3+3]-Hexakisadduct (46) and N-(L-Alanyl)-L-phenylalanine [3+3]-Hexakisadduct (48): The coupling of N-(L-alanyl)-L-phenylalanine tert-butyl ester (459.3 mg, 12 eq) with the [3+3]-hexakisadduct hexaacid 37 (285.3 mg, 1 eq) was carried out according to the procedure for [3+3]-hexakisadduct 53 by activation with DCC (12 eq) and NHS (12 eq). Purification by flash chromatography (SiO$_2$, CH$_2$Cl$_2$:MeOH=97:3 to 96:4) gave tert-butyl protected [3+3]-hexakisadduct 46 (382.6 mg, 0.100 mmol) as a dark yellow solid (76.3% yield). The tert-butyl protecting groups of 46 (172.1 mg, 0.045 mmol) were cleaved off with THF/CH$_2$Cl$_2$ as in the cases above and the [3+3]-hexakisadduct peptidoderivative 48 was obtained as a yellow solid in quantitative yield (157.0 mg, 0.045 mmol).

46: $^1$H NMR (400 MHz, RT, CDCl$_3$): δ=7.21 and 7.14 (m, 30H+6H), 7.06 (d br, 6H), 4.68 (m, 6H), 4.60 (m, 12H), 4.28 (m, 12H), 4.12 (m, 3H), 3.96 (m, 3H), 3.03 (m, 12H), 2.28 (m, 12H), 2.00 (m, 12H), 1.77 (m, 6H), 1.53 (m, 9H), 1.35 (d, $^2$J=7.01 Hz, 18H), 1.15 (m, 18H), 0.78 (m, 3H).—$^{13}$C NMR (100.5 MHz, RT, CDCl$_3$): δ=172.28, 172.20 (12C), 171.75, 171.61, 171.54 (6C), 163.68, 163.53, 163.47, 163.44, 163.08 (12C), 146.27, 146.25, 145.81, 145.79, 145.74, 145.69, 145.16, 145.12, 144.89, 144.86, 142.12, 141.88, 141.86, 141.58, 141.52, 141.39, 141.35, 140.94, 140.92, 140.87, 140.75, 140.63, 140.61 (48C, C$_{60}$ sp$^2$), 136.12 (6C), 129.38 (12C), 128.29 (12C), 126.88 (6C), 82.10 (6C), 69.25, 69.17 (12C), 67.05, 66.39, 66.30 (12C), 48.59 (12C), 46.77, 45.36 (6C), 37.93, 37.90 (6C), 31.79, 31.76 (6C), 29.23, 29.16, 28.78, 27.89 (12C), 26.33, 25.57 (6C), 24.06, 23.95, 23.87 (6C), 18.16, 17.96 (6C).—IR (KBr): ν=3388, 3309, 3062, 3029, 2976, 2933, 2857, 1744, 1652, 1524, 1455, 1369, 1263, 1219, 1156, 1079, 1044, 1017, 992, 844, 738, 714, 702, 539, 528 cm$^{-1}$.—MS (FAB): m/z=3826 [M+H]$^+$, 3770 [M−tBu]$^+$, 3495 [M−6 tBu]$^+$, 720 [C$_{60}$]$^+$.—UV/Vis (CH$_2$Cl$_2$): λ$_{max}$=244, 270.5, 281.5, 318, 337.5.

48: $^1$H NMR (300 MHz, RT, THF-d$_8$): δ=7.61 (m, 12H), 7.18 (m, 30H), 4.68 (m, 6H), 4.52 (m, 12H), 4.25 (m, 12H), 4.06 (m, 3H), 3.92 (m, 3H), 3.13 (dd, $^2$J=12.5 Hz, $^2$J=6.30 Hz, 6H), 2.97 (dd, $^2$J=12.5 Hz, $^2$J=6.30 Hz, 6H), 2.22 (m, 12H), 1.92 (m, 12H), 1.73 (m, 6H), 1.51 (m, 9H), 1.38 (m, 3H), 1.23 (m, 36H), 0.85 (m, 3H).—$^{13}$C NMR (75 MHz, RT, THF-d$_8$): δ=173.36, 173.24, 173.06 (6C), 172.39, 172.36, 172.14 (12C), 164.08, 164.00, 163.83, 163.79, 163.34, 163.31 (12C), 147.23, 147.21, 146.92, 146.90, 146.70, 146.67, 146.59, 146.32, 146.30, 145.99, 145.92, 145.84, 145.72, 145.69, 143.11, 143.01, 142.99, 142.70, 142.62, 142.55, 142.57, 142.00, 141.91, 141.85, 141.72 (48C, C$_{60}$ sp$^2$), 138.17 (6C), 130.36 (12C), 128.96 (12C), 127.32 (6C), 70.30 (12C), 66.40 (12C), 49.27 (12C), 47.94, 46.75 (6C), 38.23 (6C), 32.35, 30.22, 29.75, 27.46, 26.54 (24C), 18.58 (6C).—IR (KBr): ν=3383, 3074, 2936, 2858, 1742, 1647, 1541, 1458, 1384, 1265, 1218, 1169, 1080, 1045, 1017, 992, 904, 810, 758, 714, 668, 540, 528 cm$^{-1}$. MS (FAB): m/z=3055 [M+Na]$^+$, 3033

[M+H]⁺, 2854, 2833, 720 [C₆₀]⁺.—UV/Vis (H₂O): $\lambda_{max}$=212.5, 244, 271.5, 282, 320, 337.

REFERENCES

[1] M. Brettreich, S. Burghardt, C. Bottcher, T. Bayerl, S. Bayerl, A. Hirsch, *Angew. Chem.* 2000, 112, 1915-1918; *Angew. Chem. Int. Ed. Engl.* 2000, 39, 1845-1848.

[2] A. P. Maierhofer, M. Brettreich, S. Burghardt, O. Vostrowsky, A. Hirsch, S. Langridge, T. M. Bayerl, *Langmuir* 2000, 16, 8884-8891.

[3] M. Braun, A. Hirsch, *Carbon* 2000, 38, 1565.

[4] M. Braun, X. Camps, O. Vostrowsky, A. Hirsch, E. Endreβ, T. M. Bayerl, O. Birkert, G. Gauglitz, *Eur. J. argo Chem.* 2000, 1173-1181.

[5] A. P. Maierhofer, M. Braun, O. Vostrowsky, A. Hirsch, S. Langridge, T. M. Bayerl, *J. Phys. Chem.* 2001, 105, 3639-3645.

[6] A. Hirsch, O. Vostrowsky, *Eur. J. Org. Chem.* 2001, 829-848.

[7] . Lamparth, C. Maichle-Moessmer, A. Hirsch, *Angew. Chem. Int. Ed. Engl.* 1995, 34, 1607-1609.

[8] X Guo, F. C. Szoka, *Acc. Chem. Res.* 2003, 36, 335-341.

[9] for examples of leading references on other types of amphiphilic fullerenes see: [9a] J.-L. Gallani, D. Felder, D. Guillon, B. Heinrich, J.-F. Nierengarten, *Langmuir* 2002, 18, 2908-2913.—[9b] D. Felder, M. G. Nava, M. Del Pilar Carreon, J.-F. Eckert, M. Luccisano, C. Schall, P. Masson, J.-L. Gallani, B. Heinrich, D. Guillon, J.-F. Nierengarten, *Helv. Chim. Acta* 2002, 85, 288-319.—[9c] J.-F. Nierengarten, J.-F. Eckert, Y. Rio, M. del Pilar Carreon, J.-L. Gallani, D. Guillon, *J. Am. Chem. Soc.* 2001, 123, 9743-9748.—[9d] G. Angelini, P. De Maria, A. Fontana, M. Pierini, M. Maggini, F. Gasparrini, G. Zappia, *Langmuir* 2001, 17, 6404-6407.—[9e] D. Felder, M. Del Pilar Carreon, J.-L. Gallani, D. Guillon, Daniel; J.-F. Nierengarten, T. Chuard, R. Deschenaux, *Helv. Chim. Acta* 2001, 84, 1119-1132.—[9f] Y. Nakamura, M. Taki, A. Asami, S. Inokuma, K. Hiratani, K. Taguchi, M. Higuchi, J. Nishimura, *Bull. Chem. Soc. Japan* 2000, 73, 1615-1619.—[9g] U. Jonas, F. Cardullo, P. Belik, F. Diederich, A. Guegel, E. Harth, A. Herrmann, L. Isaacs, K. Muellen, et al., *Chem. Eur. J.* 1995, 1, 243-251.—[9h] M. Matsumoto, H. Tachibana, R. Azumi, M. Tanaka, T. Nakamura, G. Yunome, M. Abe, S. Yamago, E. Nakamura, *Langmuir* 1995, 11, 660-665.—[9i] F. Diederich, U. Jonas, V. Gramlich, A. Herrmann, H. Ringsdorf, C. Thilgen, *Helv. Chim. Acta* 1993, 76, 2445-2453.—[9j] A. M. Cassell, C. L. Asplund, J. M. Tour, *Angew. Chem. Int. Ed. Engl.* 1999, 38, 2403-2405.—[9k] S. Zhou, C. Burger, B. Chu, M. Sawamura, N. Nagahama, M. Toganoh, U. E. Hackler, H. Isobe, E. Nakamura, *Science* (Washington, D.C., United States) 2001, 291(5510), 1944-1947.

[10] M. Hetzer, H. Clausen-Schaumann, S. Bayerl, T. M. Bayerl, X. Camps, O. Vostrowsky, A. Hirsch, *Angew. Chem.* 1999, 111, 2103-2106; *Angew. Chem. Int. Ed. Engl.* 1999, 38, 1962-1965.

[11] H. A. Staab, M. Lueking, F. H. Duerr, *Ber.* 1962, 95, 1275-1283.

[12] X. Camps, A. Hirsch, *J. Chem. Soc., Perkin Trans. 1* 1997, 1595-1596.

[13] X. Camps, Ph.D. Dissertation, *Dendrimer-Fullerenes and Lipo-Fullerenes: Synthesis, Properties and Organization*, Univ. of Erlangen-Nürnberg, 1998.

[14] I. Lamparth, A. Herzog, A. Hirsch, *Tetrahedron* 1996, 52, 5065-5075.

[15][15a] G. Wegner, *Chimia* 1974, 28, 475-484.—[15b] G. Wegner, *Z. Naturforsch. B* 1969, 24, 824-832.—[15c] K. Takeda, G. Wegner, *Makromol. Chem.* 1972, 160, 349-353.—[15d] G. Wegner, *Angew. Chem.* 1981, 93, 352-371.

[16] U. Reuther, T. Brandmüller, W. Donaubauer, F. Hampel, A. Hirsch, *Chem. Eur. J.* 2002, 8, 2261-2273.

[17] B. Buschhaus, W. Bauer, A. Hirsch, *Tetrahedron* 2003, 59, 3899-3915.

[18] M. Brettreich, Ph. D. Dissertation, *Wasserlösliche und amphiphile Fulleren-Derivate: Synthese, Aggregationsverhalten und biologische Eigenschaften*, Univ. of Erlangen-Nürnberg, 2000.

[19] U. Reuther, Ph.D. Dissertation, *Evaluation of synthetic pathways for the heterofullerene $C_{59}N$ and introduction of the first concept for a completely regioselective control of multiple adduct formation of $C_{60}$*, Univ. of Erlangen-Nürnberg,

[20] L. Isaacs, A. Wehrsig, F. Diederich, *Helv. Chim. Acta* 1993, 76, 1231.

[21] D. D. Perrin, W. L. F. Amarego, *Purification of Laboratory Chemicals*, 3rd. edition Oxford, Pergamon Press, 1988.

[22] W. C. Still, M. Kahn, A. Mitra, *J. Org. Chem.* 1978, 43, 2923-2925.

[23] B. Danner, Diploma thesis, *Derivatisierte Fullerene in Membranen*, Univ. of Würzburg, 1999.

[24] R. N. Zuckermann, E. J. Martin, D. C. Spellmeyer, G. B. Stauber, K. R. Shoemaker, J. M. Kerr, G. M. Figliozzi, D. A. Goff, M. A. Siani, R. Simon, S. C. Banville, E. G. Brown, L. Wang, L. S. Richter, W. H. Moos, *Journal of Medicinal Chemistry* 1994, 37, 2678-2685.

All of the compositions and methods disclosed and claimed herein can be made and executed without undue experimentation in light of the present disclosure. While the compositions and methods of this invention have been described in terms of particular embodiments, it will be apparent to those of skill in the art that variations may be applied to the compositions and methods and in the steps or in the sequence of steps of the methods described herein without departing from the concept, spirit and scope of the invention. All such variations apparent to those skilled in the art are deemed to be within the spirit, scope and concept of the invention as defined by the appended claims.

What is claimed is:

1. A micelle, comprising:
an outer layer having an inner surface and an outer surface, the outer layer comprising a plurality of substituted fullerenes, each substituted fullerene selected from the group consisting of 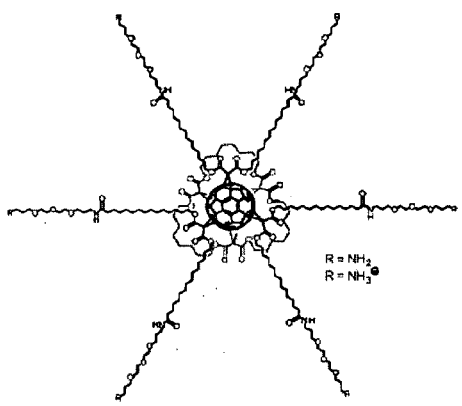 , 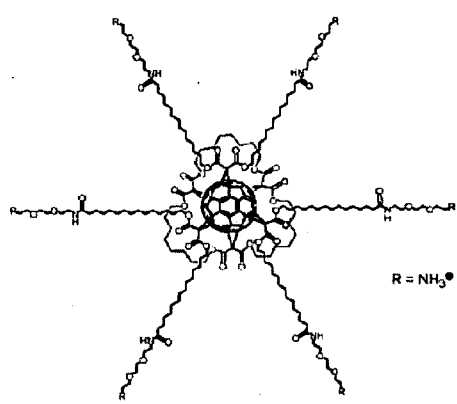 ,
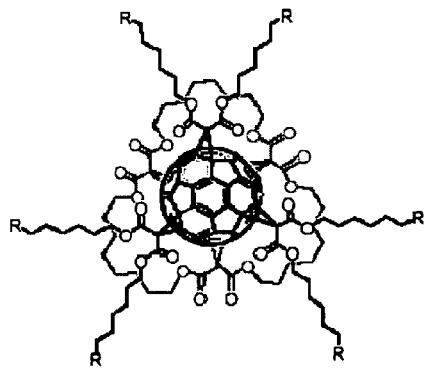
R = -NH$_3^\oplus$ ,
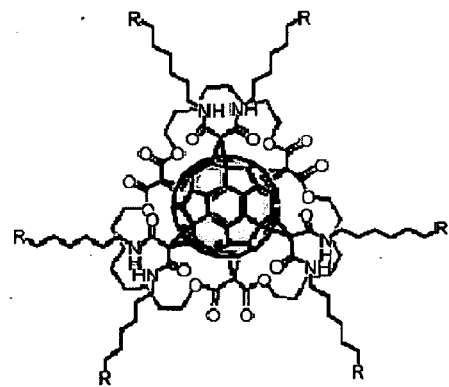
R = -NH$_3^\oplus$ ,

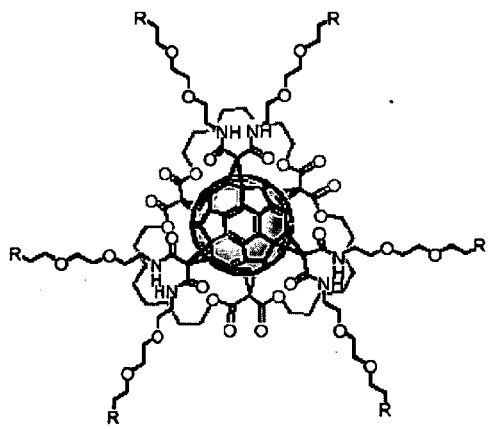
R = -NH$_3^\oplus$
,
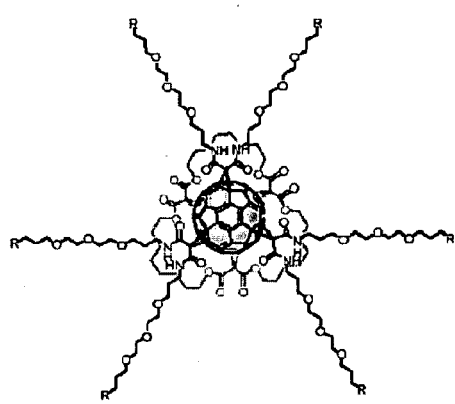
R = -NH$_3^\oplus$ ,
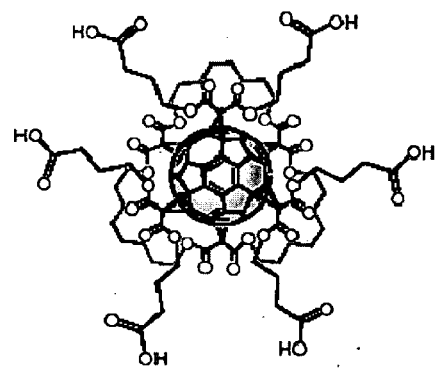
,

39
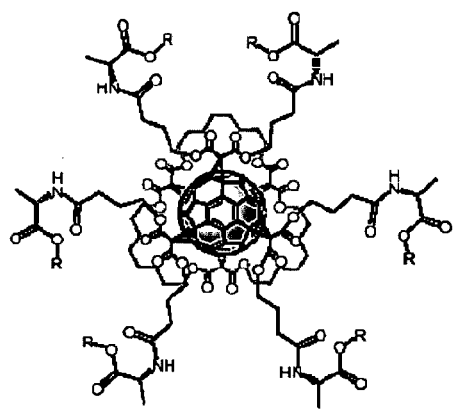
R = H
40
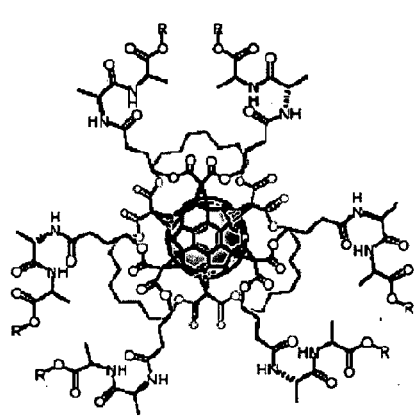
R = H
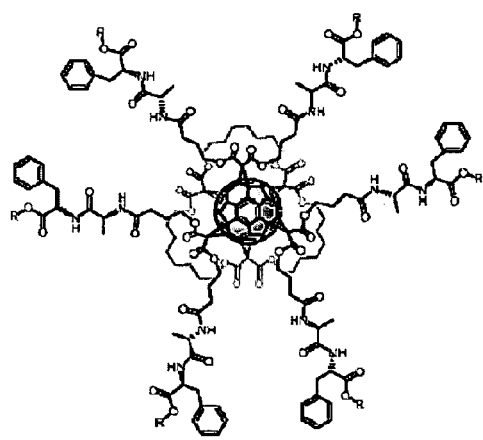
R = H
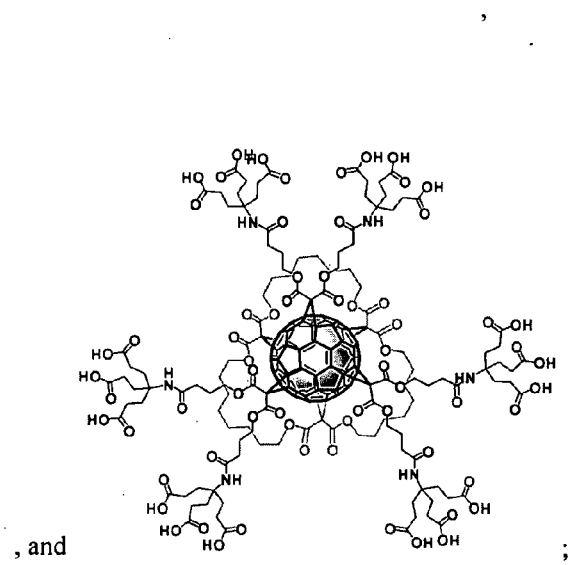
, and wherein the outer surface of the outer layer is defined by an interface between polar extended malonate groups of the compound and an aqueous solvent.

2. The micelle of claim 1, further comprising an inner layer having an inner surface and an outer surface, the inner layer comprising a plurality of substituted fullerenes, each substituted fullerene selected from the group consisting of 43
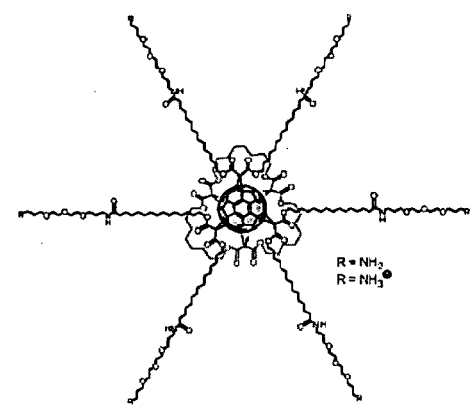
R = NH₂
R = NH₃⊕
44
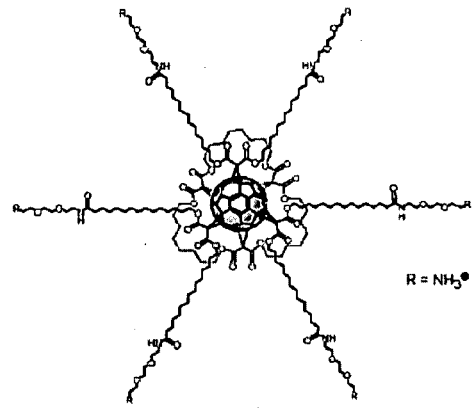
R = NH₃⊕
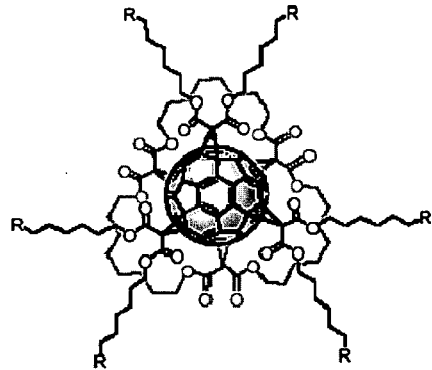
R = -NH₃⊕
,
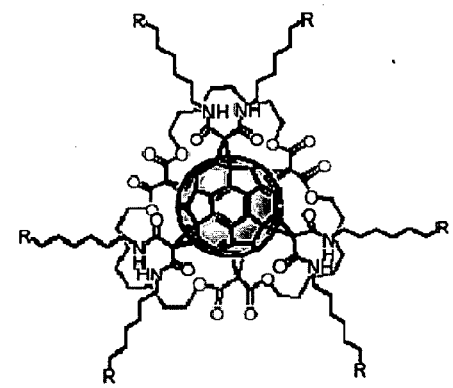
R = -NH₃⊕
,

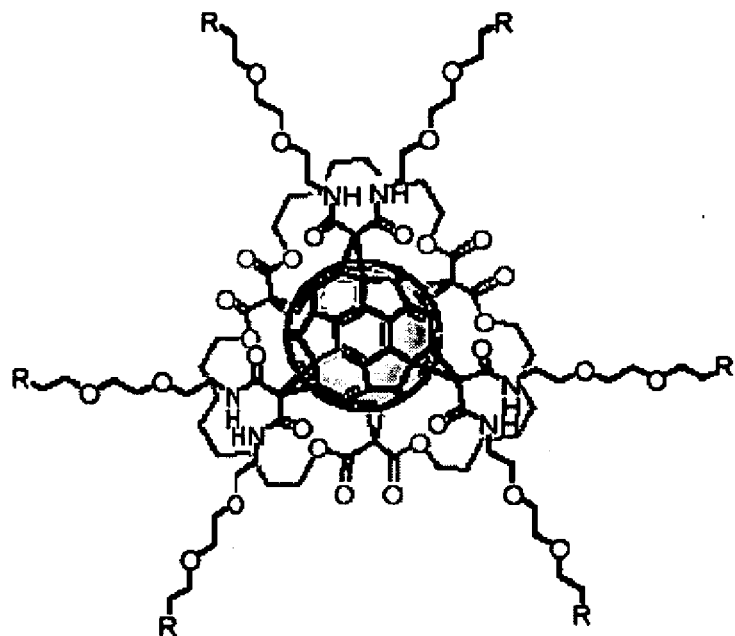
R = -NH$_3^\oplus$
,
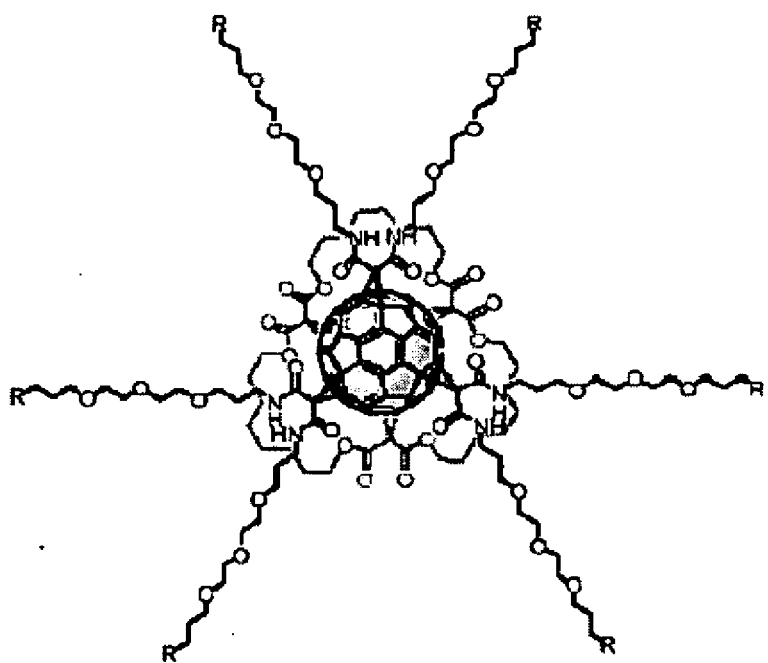
R = -NH$_3^\oplus$
,

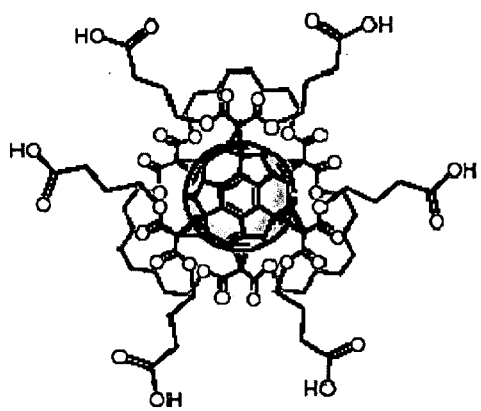
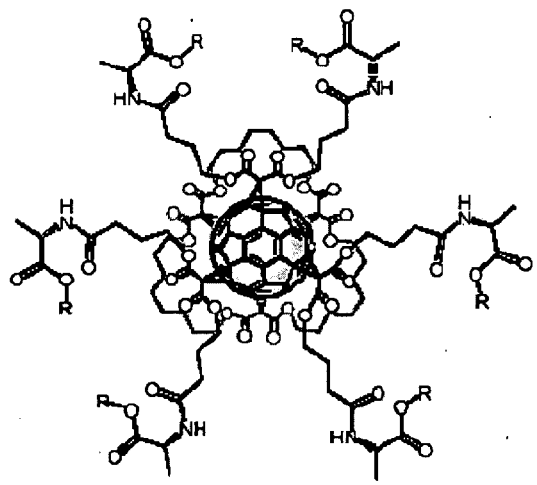
R = H
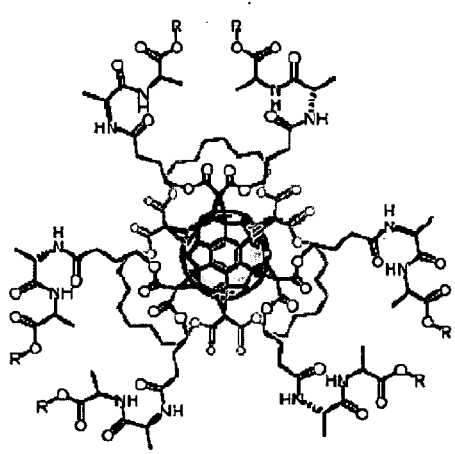
R = H
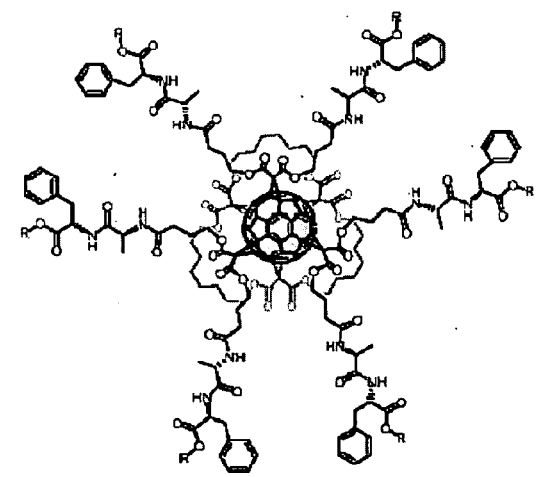
R = H and 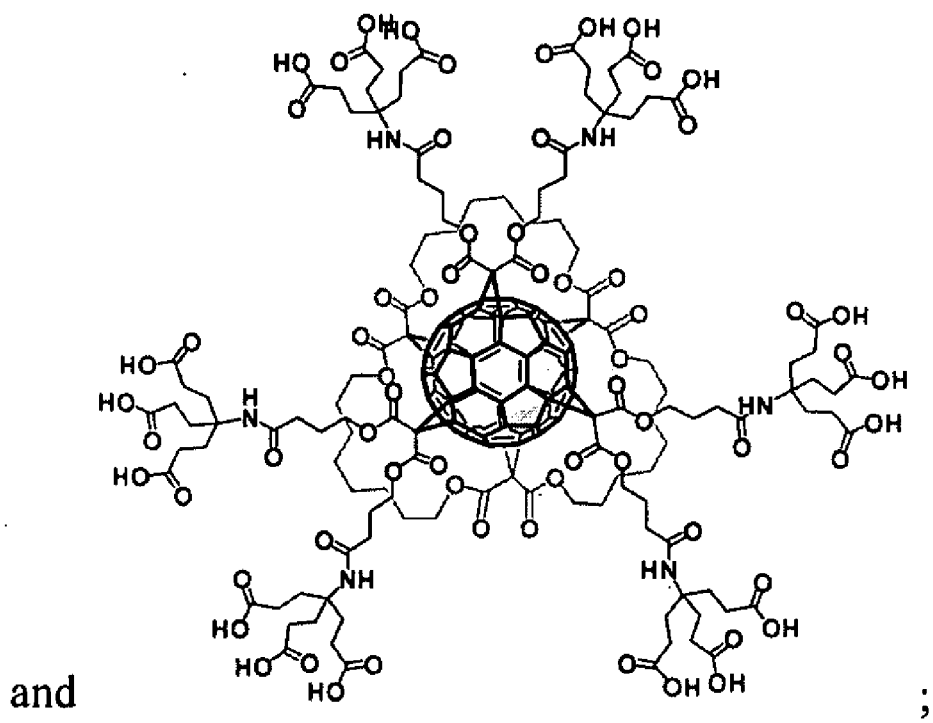 ;

wherein the inner surface of the outer layer and the outer surface of the inner layer are defined by an interface between dihydrocarbylmalonate groups of the compound in the outer layer and dihydrocarbylmalonate groups of the compound in the inner layer, and the inner surface of the inner layer is defined by an interface between polar extended malonate groups of the compound in the inner layer and an aqueous solvent contained within the micelle.

* * * * *